United States Patent
Smigielski et al.

(10) Patent No.: US 10,799,334 B2
(45) Date of Patent: Oct. 13, 2020

(54) SYSTEM, DEVICES AND METHODS FOR ANATOMICALLY CORRECT RECONSTRUCTION OF LIGAMENTS

(71) Applicant: Sports Medicine Innovations AG, Rehetobel (CH)

(72) Inventors: Robert Smigielski, Nieporet (PL); Christian Fink, Innsbruck (AT); Ralner Siebold, Walldorf (DE); Wolfgang Schwaiger, Innsbruck (AT)

(73) Assignee: Medacta International SA, Castel San Pietro (CH)

( * ) Notice: Subject to any disclaimer, the term of this patent is extended or adjusted under 35 U.S.C. 154(b) by 1395 days.

(21) Appl. No.: 14/769,565

(22) PCT Filed: Feb. 24, 2014

(86) PCT No.: PCT/IB2014/000196
§ 371 (c)(1),
(2) Date: Oct. 5, 2015

(87) PCT Pub. No.: WO2014/128551
PCT Pub. Date: Aug. 28, 2014

(65) Prior Publication Data
US 2019/0192278 A1 Jun. 27, 2019

Related U.S. Application Data

(60) Provisional application No. 61/767,816, filed on Feb. 22, 2013.

(51) Int. Cl.
*A61F 2/08* (2006.01)
*A61B 17/17* (2006.01)
*A61F 2/30* (2006.01)

(52) U.S. Cl.
CPC ........ *A61F 2/0805* (2013.01); *A61B 17/1714* (2013.01); *A61F 2/0811* (2013.01);
(Continued)

(58) Field of Classification Search
CPC ......... A61B 17/1714; A61F 2002/0841; A61F 2/0805; A61L 2430/10
See application file for complete search history.

(56) References Cited

U.S. PATENT DOCUMENTS

| 4,665,951 A | 5/1987 | Ellis |
| 5,192,322 A | 3/1993 | Koch et al. |

(Continued)

FOREIGN PATENT DOCUMENTS

| EP | 1 813 226 A1 | 8/2007 |
| FR | 2 697 151 A1 | 4/1994 |

(Continued)

OTHER PUBLICATIONS

International patent application No. PCT/IB2014/000196, International Search Report, dated Nov. 19, 2014.

(Continued)

*Primary Examiner* — David H Willse
(74) *Attorney, Agent, or Firm* — Da Vinci Partners LLC; John Moetteli

(57) ABSTRACT

A method, system and devices for the reconstruction of ribbon shaped ligaments following the anatomical native insertion sites of the ligaments in the corresponding bones is described. The reconstruction of the anterior cruciate ligament of the human knee is depicted. The system includes a device for positioning and creating bone-tunnels, the preparation of grafts and the fixation thereof. The devices intended for bone tunnel creation take into account the ribbon-shaped nature of the ligament and can be adjusted to patient specific anatomy and take into consideration the (Continued)

various typologies of the ligament insertion sites. The method and devices for graft preparation are construed to reflect the anatomy of ligaments under consideration as close as possible to native ligaments by imitating the ribbon-like nature of native ligaments. The presented fixation methods follow this principle and are intended to support the ribbon-like nature of the grafts and are intended to support in-growth of the grafts. Furthermore, accessories supporting preparation of the grafts are presented.

8 Claims, 31 Drawing Sheets

(52) U.S. Cl.
CPC . *A61F 2002/087* (2013.01); *A61F 2002/0817* (2013.01); *A61F 2002/0841* (2013.01); *A61F 2002/0852* (2013.01); *A61F 2002/0882* (2013.01); *A61F 2002/30187* (2013.01)

(56) References Cited

U.S. PATENT DOCUMENTS

| | | |
|---|---|---|
| 5,374,269 A | 12/1994 | Rosenberg |
| 6,524,317 B1 | 2/2003 | Ritchart et al. |
| 6,723,524 B1 | 4/2004 | Mermens |
| 2003/0130735 A1 | 7/2003 | Rogalski |
| 2004/0117014 A1 | 6/2004 | Bryant |
| 2005/0033301 A1 | 2/2005 | Lombardo |
| 2006/0155290 A1* | 7/2006 | Shino .............. A61B 17/1604 606/86 R |
| 2009/0234452 A1 | 9/2009 | Steiner et al. |

FOREIGN PATENT DOCUMENTS

| | | | |
|---|---|---|---|
| GB | 2 473 299 A | 3/2011 | |
| WO | WO 92/16167 A1 * | 10/1992 | ............... A61F 2/08 |
| WO | WO 98/11839 A1 | 3/1998 | |
| WO | WO 2005/079708 A1 | 9/2005 | |
| WO | WO 2012/121986 A2 | 8/2012 | |

OTHER PUBLICATIONS

Siebold et al., Resporation of the tibial ACL footprint area and geometry using the Modified Insertion Site Table, Knee Surg Sports Traumatol Arthrosc., Sep. 2012; 20(9).

Siebold et al., Tibial C-shaped insertion of the ACL without posterolateral Bundle, Chapter of ESSKA Book: ACL Reconstruction, DOI: 10.1007/978-3-642-45349-6, ESSKA 2014.

* cited by examiner

Anatomy of the knee

Tibial insertion site of the ACL (arrows)

Femoral insertion site of the ACL (arrows)

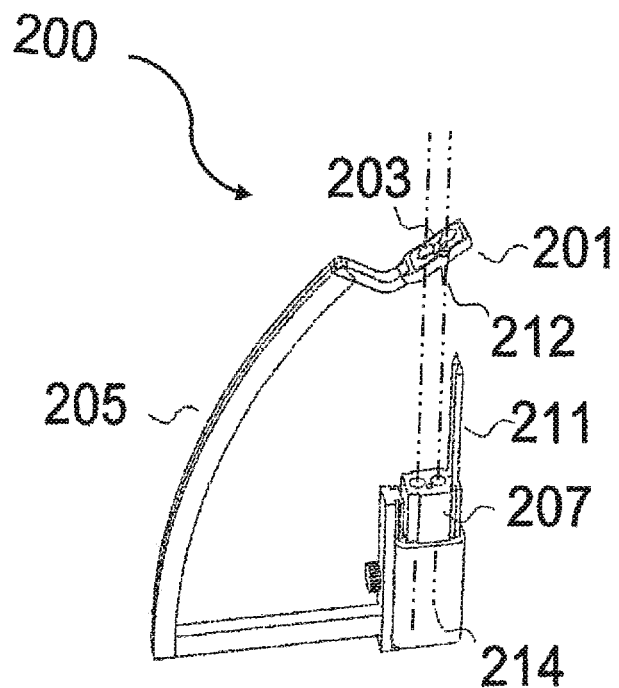
FIG.2A
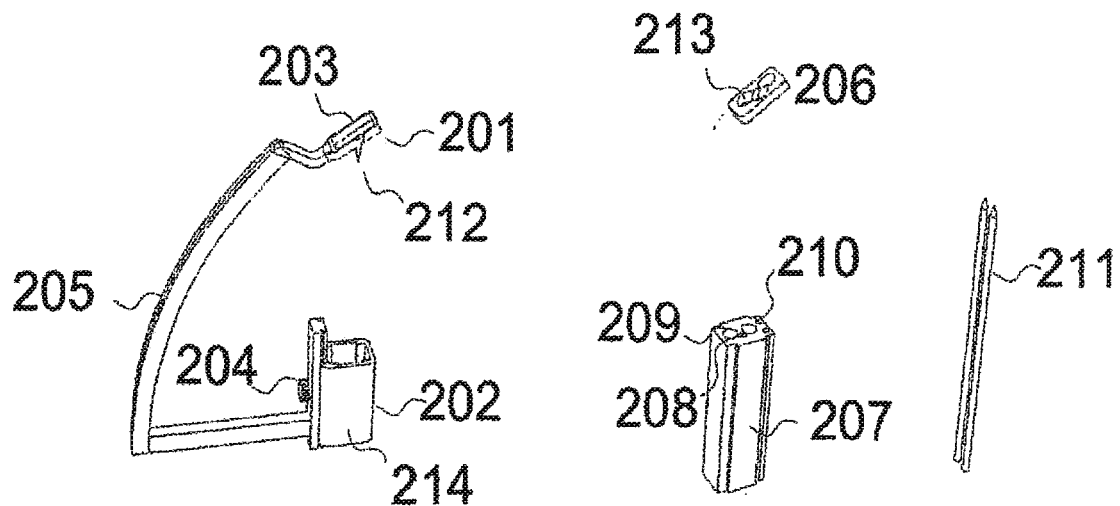
FIG.2B
FIG.2C

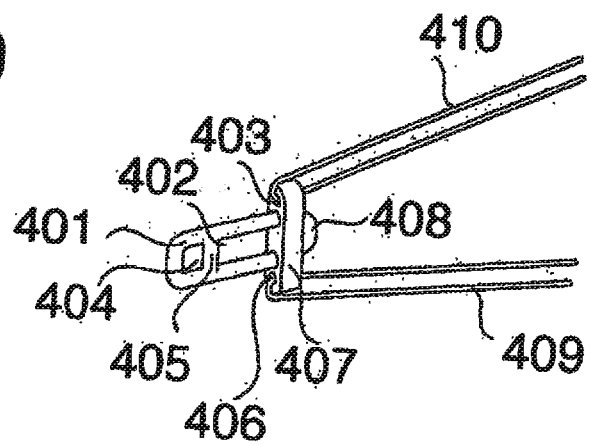
FIG. 7A
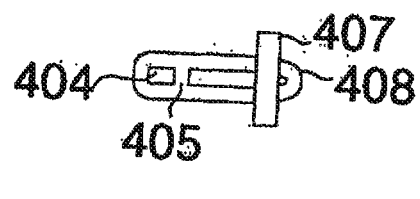 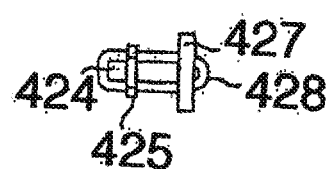
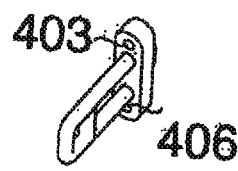 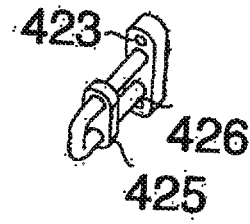
FIG. 7B                FIG. 7C Backside Backside

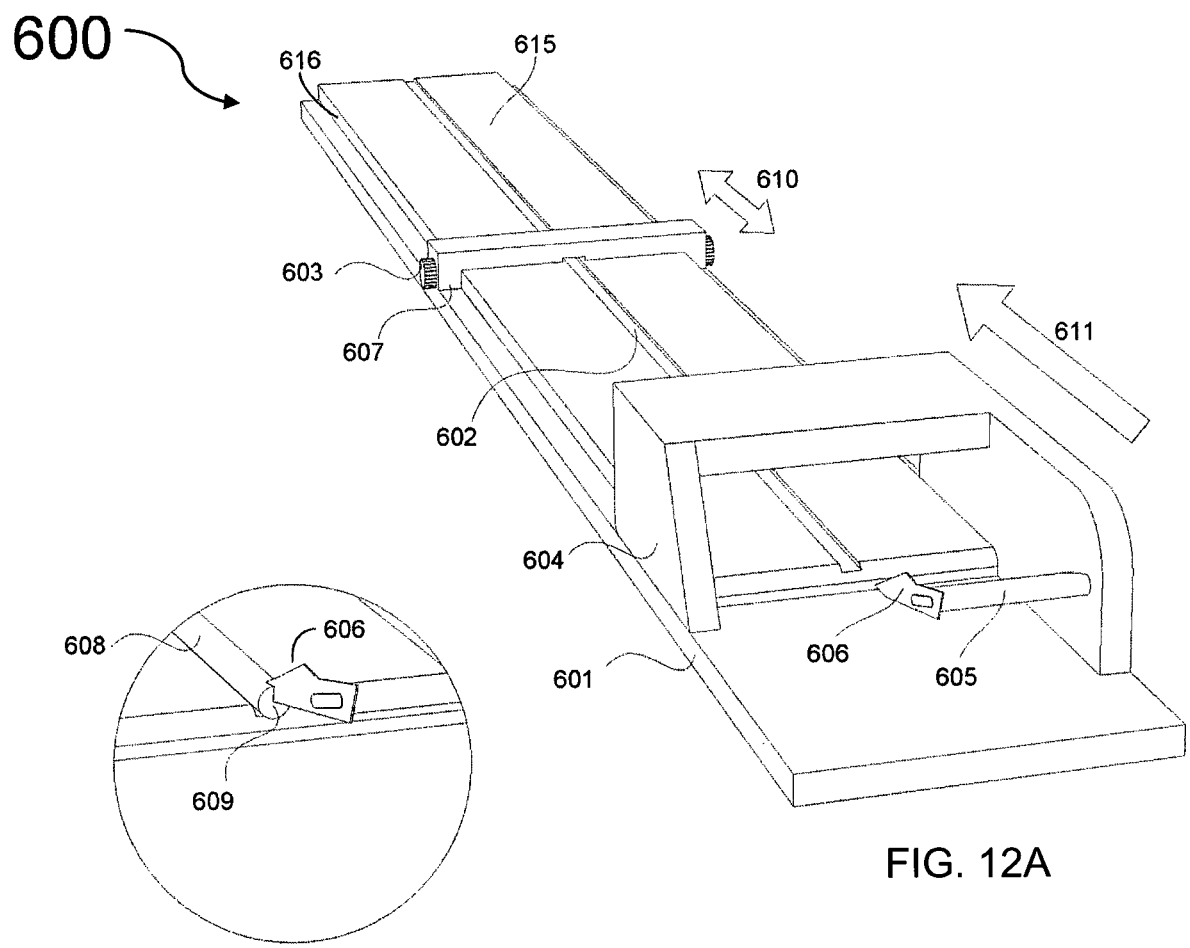
FIG. 12A
FIG. 12B
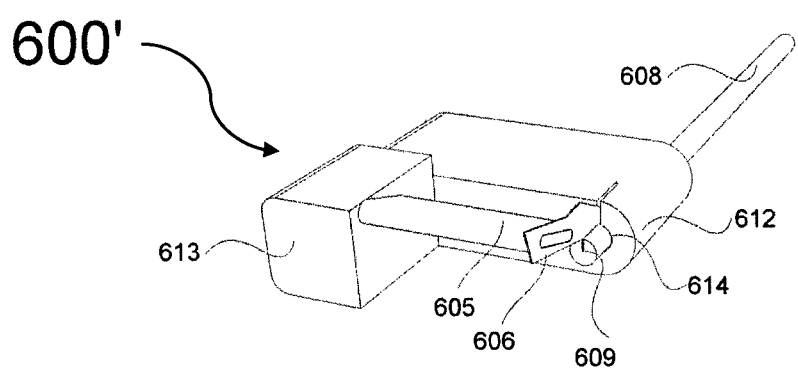
FIG. 12C

Creation of ACL- Insertion site

| 1120 | 1120' |
|---|---|
| Creation of tibial tunnel | Creation of femoral tunnel |
| 1. Clean and identify tibial footprint | 1. Clean and identify femoral footprint |
| 2. Measure tibial footprint with templates | 2. Measure femoral footprint with template |
| 3. Attach intra-articular template to tibial guiding device | 3. Introduce k-wire (with stamping device) to corresponding femoral guiding device |
| 4. Attach corresponding drill sleeves to tibial guiding device | 4. Set k-wire with the aid of the aiming template and the arthroscope |
| 5. Drill guidewire | 5. Drill guidewire |
| 6. Check orientation of tibial guiding device | 6. Check orientation of femoral guiding device |
| 7. Drill adjacent bores | 7. Drill adjacent bores |
| 8. Remove tibial guding device | 8. Remove femoral guding device |
| 9. Drill bore over guidewire | 9. Drill bore over guidewire |
| 10. Eventually clean drilling edges with bur, rasp, knife, etc. | 10. Eventually clean drilling edges with bur, rasp, knife, etc. |

FIG. 18A  FIG. 18B

Creation of ACL- Insertion sites employing preferred embodiment

10120
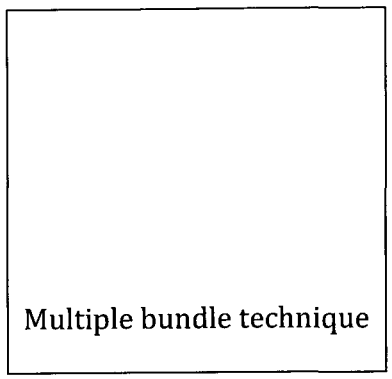
Multiple bundle technique
10120'
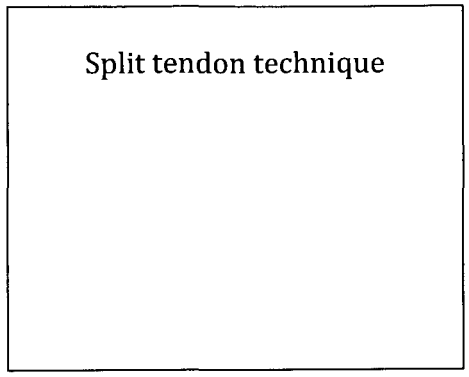
Split tendon technique
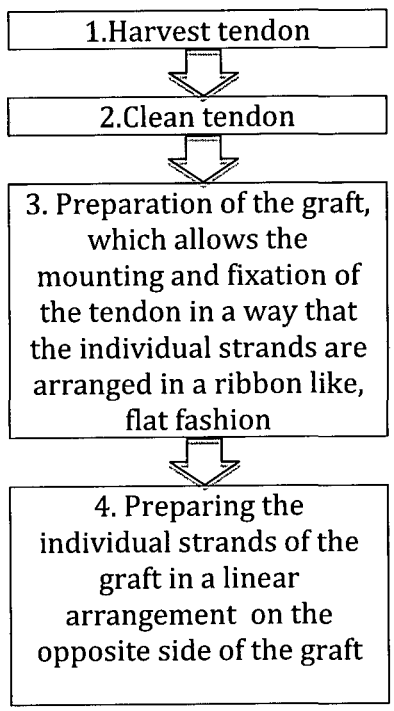
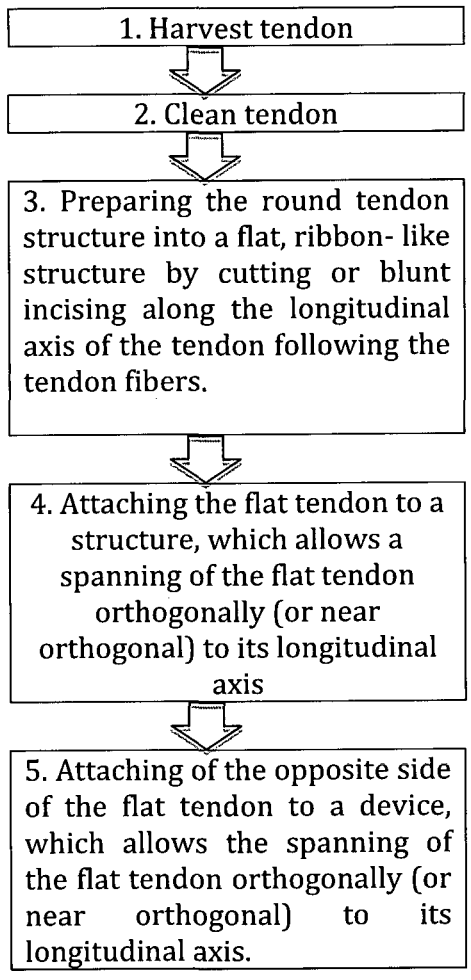
FIG. 19A
FIG. 19B
Preparation of flat, ribbon- like grafts for the reconstruction of ligaments
Alternative preparation techniques Preparation of flat, ribbon- like grafts for the reconstruction of ligaments employing the preferred embodiments / Alternative preparation techniques.

Reconstruction of ligaments employing flat, ribbon- like grafts

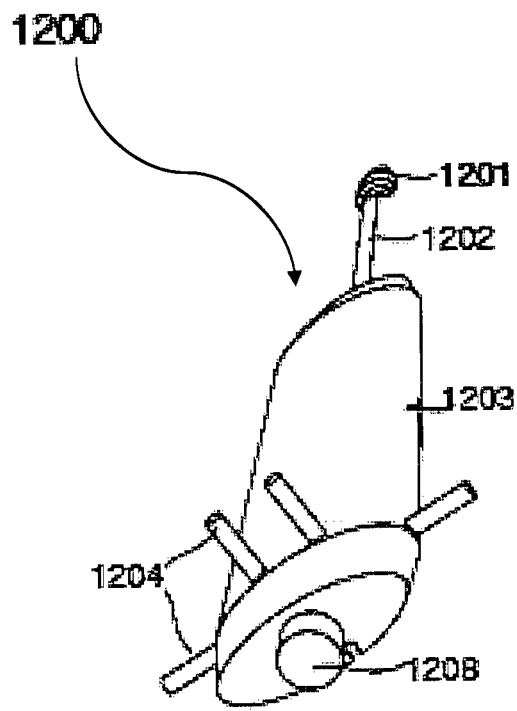# 
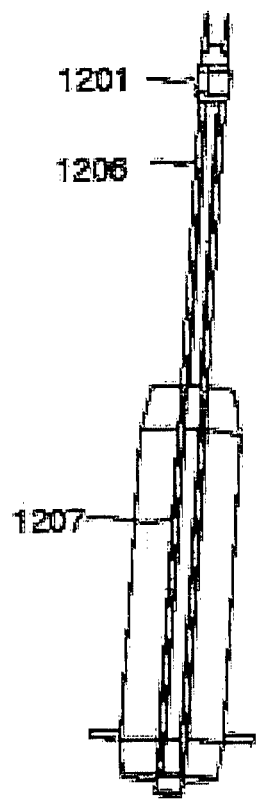
FIG. 22A
FIG. 22B
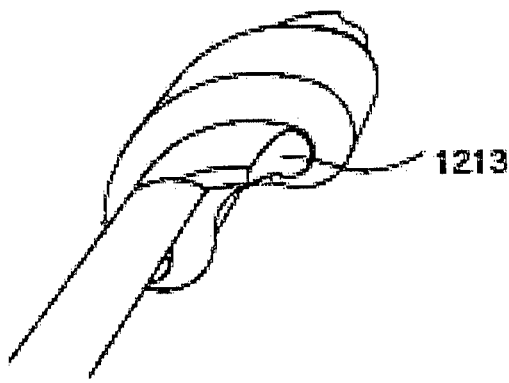
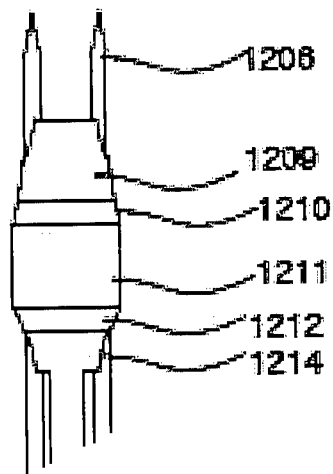
FIG. 22C
FIG. 22D

SYSTEM, DEVICES AND METHODS FOR ANATOMICALLY CORRECT RECONSTRUCTION OF LIGAMENTS

CROSS REFERENCE TO RELATED APPLICATIONS

This application is the National Stage of international Application No. PCT/IB2014/000196, filed Feb. 24, 2014, which claims benefit under 35 USC § 119(a), to U.S. provisional patent application No. 61/767,816, filed Feb. 22, 2013.

FIELD OF THE INVENTION

The current invention relates to reconstruction of ribbon shaped ligaments, in general, and more precisely to new methods, systems and devices for a more naturally occurring anatomical reconstruction of the cruciate ligaments. By way of example, the reconstruction of the anterior cruciate ligament is described.

BACKGROUND OF THE INVENTION

The reconstruction of ligaments is necessary, when a ligament is torn and other measures to stabilize the affected joint do not show sufficient success. Among other joints, the knee is particularly affected. The anterior cruciate ligament ("ACL") suffers the most injuries, predominantly among competitive athletes. ACL reconstruction surgery is one of the most common types of orthopedic surgeries and approximately 60,000-75,000 ACL reconstructions are performed annually in the United States, and many more worldwide.

Movements of the knee joint are determined by the shape of the articulating surfaces of the tibia and femur and the orientation of the four major ligaments of the knee joint: the anterior cruciate ligament (ACL) and posterior cruciate ligament (PCL) and the medial and lateral collateral ligaments function as a four bar linkage biomechanical mechanism. The principal function of the ACL is to resist anterior displacement of the tibia on the femur when the knee is flexed and control the "screw home mechanism" of the tibia in terminal extension of the knee. Knee flexion/extension involves a combination of rolling and sliding which is called "femoral roll back." This allows increased ranges of flexion. Asymmetry between the lateral and medial femoral condyles permits the lateral condyle to roll a greater distance than the medial condyle during 20° of knee flexion. This causes coupled external rotation of the tibia which has been described as the "screw-home mechanism" of the knee that locks the knee into extension. The ACL drives this screw home mechanism, and absence of ACL control is the basis of the pivot shift test of an ACL deficient knee.

A secondary function of the ACL is to resist varus rotation of the tibia, especially in the absence of the collateral ligaments. Additionally, the ACL resists internal rotation of the tibia. An ACL tear is most often sports-related, and results in knee joint instability and impaired biomechanical function. However, ACL tears also occur during rough play, motor vehicle collisions, falls, and work-related injuries. A high percentage of sports-related ACL tears are "non-contact" injuries. The injury occurs without the contact of another athlete, such as a tackle in rugby or football, or physical contact between basketball players. Most often ACL tears occur when an athlete pivots or lands from a jump. The knee "gives-out" from under the athlete when the ACL is torn and can no longer serve to biomechanically stabilize the knee. Furthermore, female athletes are at a higher risk of injuring their ACL while participating in sporting activities than male athletes.

High profile athletes very often have particular difficulty once they have sustained an ACL tear. Competitive sports, such as basketball, hockey, soccer, football and rugby require a fully biomechanically functioning ACL to perform maneuvers such as cutting, pivoting, and sudden turns. Periodic athletes may be able to function in their normal daily activities without a normally biomechanically functioning ACL, but athletes engaging in high-demand sports have difficulty in doing so. Hence, athletes with ACL tears are often faced with the decision to undergo ACL reconstructive surgery in order to return to their previous level of performance.

DESCRIPTION OF THE RELATED ART

Anterior cruciate ligament (ACL) reconstructions are commonly performed by placing one or two bone tunnels at a tibial and femoral location of the torn ACL. By oblique drilling, oval bone tunnels at the tibial and femoral locations are created. (Siebold et al., Restoration of the tibial ACL footprint area and geometry using the Modified Insertion Site Table, Knee Surg Sports Traumatol Arthrosc., 2012 September; 20(9):1845-9, the content of which is incorporated herein by reference) Various methods of ACL reconstruction have been proposed in the art. By way of example, U.S. Pat. No. 6,723,524 describes: "A surgical implant for securing ligament grafts into a joint. The implant is formed entirely of allograft cortical bone, and has a tapered tip with a suture eye. A length of suture is knotted or looped through the eye. The suture is used to draw the implant transversely through a looped graft construct to fix the graft by spanning a bone socket. The implant is used for knee ligament repair by forming a longitudinal socket in a bone. A flexible strand is drawn with the pin through the bone. A looped portion of the flexible strand is diverted so as to protrude out of the entrance to the longitudinal socket. The ends of the flexible strand remain accessible on either side of the bone. The ligament graft is captured within the strand loop protruding from the entrance to the socket. The strand is retracted into the socket, drawing the graft into the socket by pulling on the accessible ends of the flexible strand."

Similarly, U.S. Pat. No. 5,374,269 also provides a method for ACL reconstruction. However, the art has several drawbacks, since it fails to take into consideration the native ACL insertion site to the femur and tibia and the shape of the ACL within the knee joint, and resultant biomechanical functionality within a single joint and in relation to an un-injured native ACL joint. Anatomical dissections show, that the ACL, like other ligaments, resembles more a "ribbon-like structure" rather than an oval structure. The femoral insertion of the ACL has a longitudinal (8-18 mm) but narrow shape (3-5 mm). (Smigielski et al., Ribbon anatomy of anterior cruciate ligament—part 1. Femoral attachment and midsubstance (submitted for review), the content of which is incorporated by reference) Therefore, conventional oval bone tunnel drilling fails to reconstruct the natural anatomical shape of the native ACL insertion site of the ACL attachment points on the femur, because in one direction the reconstruction is too narrow and in the other direction too wide to resemble natural anatomic conditions and two and three dimensional structure, and provide for the naturally intended stability and biomechanical function of the knee joint.

On the tibial side, anatomical dissections have shown, that the insertion site of the ligament is not oval but appears rather "half-moon" or C-shaped. In some patient specific variations, the C-shaped insertion site is elongated on one end of the C, thereby having an appearance of a more "J-shaped" insertion site. Siebold et al, Tibial C-shaped insertion of the Anterior Cruciate Ligament without Posterolateral Bundle, Chapter of ESSKA Book: Anterior Cruciate Ligament Reconstruction, DOI) 10.1007/978-3-642-45349_3, ESSKA 2014, the content of which is hereby incorporated by reference. For the purposes of this application, the meaning of the term "C-shaped" includes variations of a C-shape, but with the insertion site mimicking a native insertion site, in one variant of the invention.

As on the femoral side, the conventional bone tunnel drilling technique does not reflect the native or natural anatomical situation on the tibial side. The natural anatomical reconstruction of the tibial insertion is not possible with an oval bone tunnel. Furthermore, parts of the anterior root of the lateral meniscus may be damaged by the conventional technique.

Current methods aim to reconstruct the ligament by orientating the graft at the general prior location of the ligament while not considering the natural footprint of the ACL at both tibial and femoral natural anchor points, while, in contrast, the method, devices and systems, here focus on the reconstruction of the insertion site of the ligament in the bone in a manner that substantially matches or mimics the natural ACL anchor point footprints on the tibia and the femur to obtain optimal anchor point configurations and biomechanical knee joint movement. This is a fundamental distinction that solves a major problem in the art, since the naturally occurring tibial and femoral ACL anchor footprint does not necessarily reflect the artificially made surgical insertion site, and therefore the optimal and natural biomechanical anchor point of the ligament. The present invention is further directed to solve this problem in the art, and does so. This is due to the fact, that—upon rupture of the ACL—not only the ligament, but also synovial and fat tissue is dislocated from the bone, giving the perceived footprint of the ligament insertion site a broader and more distorted appearance than in nature. For example, as shown by Smigielski et al., the ACL's fibers form a flat ribbon as close as 2 to 3 mm from its naturally occurring femoral attachment point, while the respective footprint at this site falsely appears to be a broader and more cylindrical structure after ACL rupture.

In summary, conventional tibial and femoral bone tunnel drilling tools, systems and methods do not anatomically reconstruct the naturally occurring insertion sites of the ACL graft at points on the tibia and femur that reflect the natural anchor point. The same holds true for ligament reconstruction techniques in other parts of the body. Hence, there exists a need in the art for tools, systems and methods suitable for the anatomical reconstruction of ribbon like ligaments and proper graft dimensioning and shaping in a ribbon like manner in the interior of the knee joint and other joints as well as outside of joints that conform to the natural anchor points of a native ACL on both the femur and the tibia post-reconstruction. The present invention solves these and other problems in the art.

SUMMARY OF THE INVENTION

The invention provides a system for preparing a first and second bone for a graft procedure. The system includes a device for creating on the first bone an entrance point mimicking a first native ligament attachment footprint, the first native ligament insertion site optionally being a substantially half-moon shaped footprint. The device has an appliance for sequential drilling and/or burring of overlapping bores, which are arranged in a c-shaped manner to create or re-create a substantially c-shaped insertion site.

It is also includes a second device for creating on the second bone an entrance point mimicking a second native ligament attachment footprint. The second native ligament attachment footprint optionally has a substantially slit shaped footprint, and the device has an appliance for sequential drilling and/or burring of overlapping bores. The bores are arranged in a substantially or perfectly slit-shaped manner to create a slit-shaped insertion site. The slit-shaped insertion site substantially conforms in size and cross-sectional dimension to a corresponding aperture created with the first device.

In another variant, the system includes and the method includes the use of a third device. The third device is selected from the group consisting of a device for creating a substantially ribbon-like ACL graft (in which the graft has a first end and a second end), a device having an appliance allowing to maintain the ribbon-like appearance of the graft by affixing parallel tendon bundles or affixing tendons which are split and prepared in a way to give a flat, ribbon like appearance, and a device for affixing portions of a tendon which have been prepared to give a substantially flat and ribbon like appearance.

In yet another variant, the system includes and the method includes the use of a fourth device for fixing at least a portion of the first end of the graft at a tibial anchor point. The fourth device has an appliance which allows affixing of a substantially flat graft to a flat or substantially flat structure on the fourth device by attaching the graft to the flat structure, the flat structure being constructed to be flexible enough to pass through a c-shaped bone tunnel.

In another variant, the invention provides a graft for ACL reconstruction. The graft includes a first portion which is shaped and dimensioned to substantially conform to a slit shaped bone entrance point. A second portion is shaped and dimensioned to be substantially ribbon like, and a third portion that is shaped and dimensioned to substantially conform to a C-shaped bone entrance point.

In yet another variant, the system is used for creating a graft for ACL reconstruction and the system includes a device for making the graft.

The system and method is used for reconstructing a portion of a knee joint with a torn anterior cruciate ligament using a graft. The graft has a first end and a second end. It is appreciated that the naturally occurring attachment footprints of a native ACL are mimicked or reconstructed to provide biomechanical stability to the knee joint that matches or substantially matches the biomechanical stability provided by a native ACL. The system includes a first immobilizer that has a button-like device attached to a flat structure. The first immobilizer is designed for positioning and use at a portion of the first end of the graft in, or optionally on a femur, at least a portion of the graft is adapted for passing through a substantially slit shaped aperture on the femur; and a second immobilizer having a flat structure attached to a mechanism. The mechanism allows for and provides for immobilization of the attached graft by wedging and blocking of the attached fixation means, and the second immobilizer is constructed and used for positioning and use at a portion of the second end of the graft in, or optionally on a tibia, such that at least a portion of the graft is adapted to pass through a substantially C-shaped aperture on the tibia.

In another variant, the invention provides a method of reconstructing a knee joint with an anterior cruciate ligament tear using a graft. The graft has a first end and a second end. The method includes the steps of: immobilizing a first end of the graft on a femur, at least a portion of the graft passing through a substantially slit shaped aperture on the femur; immobilizing a second end of the graft on a tibia, at least a portion of the graft passing through a substantially C-shaped aperture on the tibia; and affixing the ends of the graft on their respective insertion sites in a manner mimicking naturally occurring attachment insertion sites of a native ACL, in order to provide biomechanical stability to the knee joint.

In another variant, the invention provides a method of providing substantially equal biomechanical stability for a bipedal mammal. The bipedal mammal has a native ACL in a first knee joint and a torn or damaged ACL in a second knee joint in the clinical setting. The method includes reconstructing the torn ACL in the second knee joint to obtain a reconstructed ACL. The reconstructed ACL includes a first portion of a graft passing through a substantially slit-like aperture in a first bone, and a second portion of the graft passing through a substantially C-shaped aperture in a second bone; affixing the ends of the graft on their respective insertion sites in a manner mimicking naturally occurring attachment insertion sites of a native ACL, in order to provide biomechanical stability to the knee joint; and, allowing for healing with physiotherapy and supervised recovery, whereby thereafter, the biomechanical stability of the first knee joint is substantially similar to the biomechanical stability of the second knee joint.

The invention further includes a method of providing substantially equal biomechanical stability for a bipedal mammal having a native ACL in a first knee joint and torn ACL in a second knee joint, whereby after healing, the biomechanical stability of the knee joints are substantially similar, the method comprising the steps of: forming a graft of an anatomically correct reconstructed ACL; forming an ACL footprint mimicking a native ACL footprint in the second knee joint; passing a first portion of the graft that passes through a substantially slit-like aperture in a first bone; passing a second portion of the graft through a substantially C-shaped aperture in a second bone; affixing the ends of the graft on their respective insertion sites in a manner mimicking naturally occurring attachment insertion sites of a native ACL, in order to provide biomechanical stability to the knee joint; and allowing for healing with physiotherapy and supervised recovery, whereby thereafter, the biomechanical stability of the first knee joint is substantially similar to the biomechanical stability of the second knee joint.

In yet another aspect, the invention includes a method of preparing a tibia for an anatomically correct ACL reconstruction. The method includes cleaning and identifying a tibial native ACL footprint; measuring the tibial native ACL footprint with a template; locating and orienting a tibial insertion site; positioning a tibial aiming device; drilling a bone tunnel, or optionally a pocket, correlated to the native tibial insertion site that has been cleaned and identified and being in a substantially C-shaped configuration; removing the tibial aiming device; and, optionally cleaning drilling edges.

In yet further variant, the invention provides a method of preparing a femur bone for an anatomically correct ACL reconstruction. The method includes the steps of: cleaning and identifying a femoral ACL footprint; measuring the native femoral ACL footprint with a template; locating and orienting a femoral insertion site; positioning a femoral aiming device; drilling a bone tunnel, or optionally a pocket, correlated with the native femoral insertion site in a substantially slit shaped native configuration; removing the femoral aiming device; and optionally cleaning drilling edges.

The invention also provides a method of creating a tibial bone tunnel during a ligament reconstruction surgery, comprising the steps of: cleaning and identifying a native tibial footprint; measuring a native tibial footprint with a template; attaching or adjusting an intra-articular template to a tibial guiding device; attaching or adjusting a corresponding drill sleeve to the tibial guiding device; drilling to provide a guide-wire or a drill which stabilises the tibial guiding device; orienting the tibial guiding device; drilling adjacent bores or adjacent k-wires in case where a drill was set to stabilise the tibial guiding device; removing the tibial guiding device; drilling a bore over the guide-wire or adjacent guide wires; and, optionally cleaning drilling edges.

In yet further variant, the invention provides a method of creating a femoral bone tunnel, comprising the steps of: cleaning and identifying a native femoral footprint; measuring a native femoral footprint with a template; introducing a k-wire with a stamping device with a corresponding femoral guiding device; setting the k-wire using an aiming template and an arthroscope; drilling to provide a guide-wire or a drill which stabilises the femoral guiding device; orienting the femoral guiding device; drilling adjacent bores or adjacent k-wires in case where a drill was set to stabilise the femoral guiding device; removing the femoral guiding device; drilling a bore over the guide-wire; and, optionally cleaning drilling edges.

In yet another variant, the invention provides a method of preparing a graft for a ligament reconstruction procedure, comprising the steps of: harvesting a tendon; cleaning the tendon; arranging individual tendon strands in a substantially ribbon-like, flat manner to mount and fixate the tendon; and, preparing the individual tendon strands in a linear arrangement.

In yet further aspect, the invention provides a method of preparing a graft for a ligament reconstruction procedure, comprising the steps of: harvesting a tendon to obtain a round tendon structure; cleaning the round tendon structure; preparing a substantially flat, ribbon-like structure from the round tendon structure along a longitudinal axis of the round tendon structure following tendon fibers, the substantially flat, ribbon-like structure having a first side and a second side; spanning the first side of the substantially flat, ribbon-like structure substantially orthogonally to the longitudinal axis of the substantially flat, ribbon-like structure by attaching the substantially flat, ribbon-like to an attachment structure; and, spanning the second side of the substantially flat, ribbon-like structure substantially orthogonally to the longitudinal axis by attaching the substantially flat, ribbon-like to an attachment structure.

In yet further variant, the invention provides a method of preparing a graft for a reconstruction procedure, comprising the steps of: harvesting a tendon having a plurality of tendon strands; cleaning the tendon; providing a split-button device having a lower partition and an upper partition; introducing the tendon into the lower partition; introducing the tendon into the upper partition; providing a fiber-pod having separate fields and loops; laying each tendon strand in a separate field; weaving the plurality of tendon strands through the loops with a plurality of pull chords; tightening the tendon strands by pulling the pull chords; and, optionally securing the tendon strands with sutures.

In another embodiment, the invention provides a method of preparing a graft for a procedure, comprising the steps of: harvesting a flat, ribbon-like portion of a tendon (e.g. patella or quadriceps tendon); cleaning the tendon portion; preparing a substantially flat tendon structure; and attaching said structure to fixation means allowing the upholding of a flat appearance of the graft.

In yet further variant of the method, the invention provides a method of reconstructing a ligament using a first bone tunnel and a second bone tunnel, comprising the steps of: creating the first bone tunnel according to and/or or corresponding to a first native ligament insertion site; creating a second bone tunnel according to and/or corresponding to a second native ligament insertion site; preparing a substantially ribbon-like, flat graft, the graft having a first end and a second end; pulling in the graft via the first bone tunnel into the second bone tunnel; fixing a portion of the first end of the graft in the second bone tunnel; tightening and fastening the graft; and, fixing a portion of the second end of the graft in the first bone tunnel. In this variant of the method the first bone tunnel is a tibial bone tunnel, and the second bone tunnel is a femoral bone tunnel.

In another variant, a system, device and method are provided for the reconstruction of ligaments and more specifically for the anatomically correct reconstruction of the anterior cruciate ligament (ACL).

It is an object of the invention to provide preparation, positioning and fixation devices for various grafts to create a ribbon like structure that mimics a native ACL.

It is another object of the invention to provide methods for the anatomical reconstruction of ribbon like ligaments, especially the anterior cruciate ligament, to favour the delay of the onset of arthrosis in the affected joint, which is a common consequence of current reconstruction techniques.

It is another object of the invention to provide tools used in the system and method for the creation of graft insertion sites of natural ACL anchor point sites (at the surface of the tibia and femur), which have a slit-like or substantially slit-like appearance to reconstruct the ACL in a ribbon-like fashion with straight and curved insertion sites at the femur and tibia, respectively, and thus mimic natural biomechanical ACL function and stability.

It is yet another object of the invention to create graft tunnels, which increase and favour bone graft interaction by providing as much bone-graft interface as reasonably possible, which again favours nutrition and in-growth of the graft, thereby reducing the risk of re-rupture of the graft post procedure.

It is another object of the invention to provide means for fixing the graft in the tibial and femoral tunnel, which allow enhanced bone-graft interaction compared to current fixation methods.

It is a further object of the invention to provide tools adjustable to the anatomic conditions of the patient for the accurate and simple location of the insertion sites.

It is another object of the invention to provide a tibial drill guide, which minimizes damage to parts of the anterior root of the lateral meniscus, as opposed to current drilling methods, where these structures may be damaged more severely.

It is another object of the invention to provide a femoral drill guide, which allows direct visualisation of the femoral insertion site and avoids damage to the femoral condyle by supplying a drill-sleeve, which covers the drill as opposed to current drilling methods, where these structures may be damaged by drills touching the femoral condyle.

It is another object of the invention to provide graft preparation means, which allow a ribbon-like attachment of various grafts.

It is yet another object of the invention to split a round tendon-structure into a ribbon-like structure that mimics a natural ACL, which resembles more the ribbon-like anatomy than current graft preparation methods.

It is another object of the invention to provide graft preparation and fixation means, which allow the fixation of split-tendon grafts in the tibial and femoral tunnel.

It is another object of the invention to provide graft preparation and fixation means, which allow the fixation of flat tendon grafts harvested from the patella tendon and the quadriceps tendon.

The present invention is directed to devices, systems and methods that are also further described in the following Brief Description of the Drawings, the Drawings, the Detailed Description of the Invention, and the claims. Other features and advantages of the present invention will become apparent from the following detailed description of the invention made with reference to the accompanying drawings.

BRIEF DESCRIPTION OF THE DRAWINGS

FIG. 2A is a perspective view of an assembled tibial aiming device, in which k-wires are used to stabilize a drill template.

FIG. 2B is a perspective view of the tibial aiming device without tibial drill templates.

FIG. 2C is a perspective view of tibial drill templates and guide-wires.

FIG. 7A is a perspective view of the device for femoral tendon attachment and fixation for a quadruple graft.

FIG. 7B shows perspective views of a sling and button for femoral tendon attachment and fixation with flexible window partitioning.

FIG. 7C shows perspective views of a sling and button for femoral tendon attachment and fixation wherein the partitioning is a bar that can move along the sling or loop.

FIG. 12A is a perspective view of a device for splitting a round tendon into a ribbon-like structure.

FIG. 12B is a detail view of a device FIG. 12A, in which the round tendon is split by a scalpel as shown.

FIG. 12C is a perspective view of an alternate embodiment of a device for splitting a round tendon into a ribbon-like structure.

FIGS. 18A and B are flowcharts depicting a method for anatomically correct reconstruction of a ligament structure employing C-shaped and slit-like bore tunnels.

FIGS. 19A and B are flowcharts depicting generic methods for the preparation of flat, ribbon-like grafts from multiple parallel bundles or from split tendons.

FIG. 22A is a perspective view of the tibial dilator.

FIG. 22B is another perspective view of the backside of the tibial dilator (with inserted k-wires).

FIG. 22C is a detail of the "head" of the tibial dilator.

FIG. 22D is a top view of the "head" of the tibial dilator with inserted k-wires.

Figure 1A:
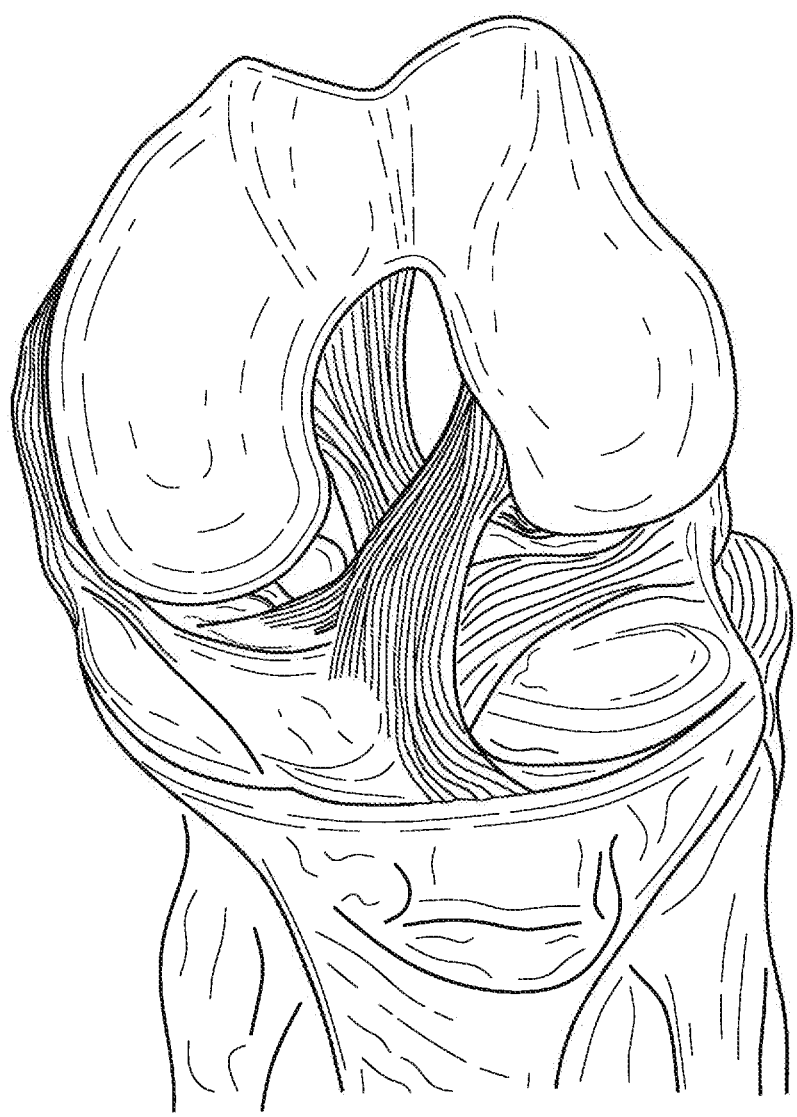
FIG. 1A is an anatomical depiction of the ligament structure of the knee.

Those skilled in the art will appreciate that elements in the figures are illustrated for simplicity and clarity and have not necessarily been drawn to scale. For example, dimensions may be exaggerated relative to other elements to help improve understanding of the invention and its embodiments. Furthermore, when the terms 'first', 'second', and the like are used herein, their use is intended to distinguish between similar elements and not necessarily for describing a sequential or chronological order. Moreover, relative terms like 'front', 'back', 'top' and 'bottom', and the like in the figures, Description and/or in the claims are not necessarily used for describing exclusive relative position. Those skilled in the art will therefore understand that such terms may be interchangeable with other terms, and that the embodiments described herein are capable of operating in other orientations than those explicitly illustrated or otherwise described.

DETAILED DESCRIPTION OF THE PREFERRED EMBODIMENT

The following description is not intended to limit the scope of the invention in any way as it is exemplary in nature, serving to describe the best mode of the invention known to the inventors as of the filing date hereof. Consequently, changes may be made in the arrangement and/or function of any of the elements described in the exemplary embodiments disclosed herein without departing from the spirit and scope of the invention.

In the following description, complete methods, devices and systems for ligament reconstruction, especially of the anterior cruciate ligament and its use are described. The systems comprise aiming devices for creating the tibial and femoral tunnels, devices for graft preparation and fixation, as well as accessories to achieve the reconstruction of ligaments that mimic the natural ACL in biomechanical shape, function and anchoring to the tibia and femur.

The method further includes repairing a knee joint with anterior cruciate ligament damage with a graft. The graft has a first end and a second end. The method includes immobilizing a first end of the graft on a femur such that at least a portion of the graft passes through a substantially slit shaped aperture on the femur; and, immobilizing the second end of the graft on a tibia such that at least a portion of the graft passes through a substantially C-shaped aperture on the tibia. It is appreciated that the naturally occurring attachment insertion sites of a native ACL are mimicked to provide biomechanical stability to the knee joint. It is also appreciated that the method and system provided herein aim at providing substantially similar naturally occurring biomechanical stability between the damaged knee joint as compared to an undamaged knee joint with a native ACL. Moreover, it is appreciated that the biomechanical stability within the repaired knee joint is returned to a substantially pre-injury biomechanical stability, particularly with respect to the ACL interaction between the posterior cruciate ligaments (PCL). Having substantially similar biomechanical stability between an uninjured knee joint and the reconstructed knee joint post ACL reconstruction, and within the reconstructed knee is highly desirable, especially among professional athletes.

As such, a method of preparing for a surgery to provide substantially equal biomechanical stability for a bipedal mammal is also included herein. The bipedal mammal (of course, other quadra-pedal mammals can benefit from the methods and systems of the invention, in other variants) having a native ACL in a first knee joint and a torn ACL in a second knee joint. The method includes providing one or more of the devices described herein to create an anatomically correct reconstructed ACL in the second knee joint. The anatomically correct reconstructed ACL includes a first portion of a graft passing through a substantially slit-like aperture in a first bone, and a second portion of the graft passing through a substantially C-shaped aperture in a second bone such that the biomechanical stability of the first knee joint is substantially similar to the biomechanical stability of the un-injured second knee joint.

With this in mind, a system for preparing a first and second bone for a graft procedure is also described herein. The system includes a device for creating on the first bone an entrance point having a substantially half-moon shaped footprint, and a device for creating on the second bone an entrance point having a substantially slit shaped footprint. While it is appreciated that the method and system herein is described for ACL reconstruction, it can be used on other ligaments in the body.

Where the method, device and system of the invention is applied to damaged ligaments in joints other than the knee joint, the anatomical attachment sites of the native ligaments are substantially matched to the reconstructed ligaments with corresponding apertures and insertion sites created in the respective bones so that biomechanical functionality is mimicked to the native ligament, as well as between joints on corresponding un-damaged limbs.

Anatomy

Figure 1B:
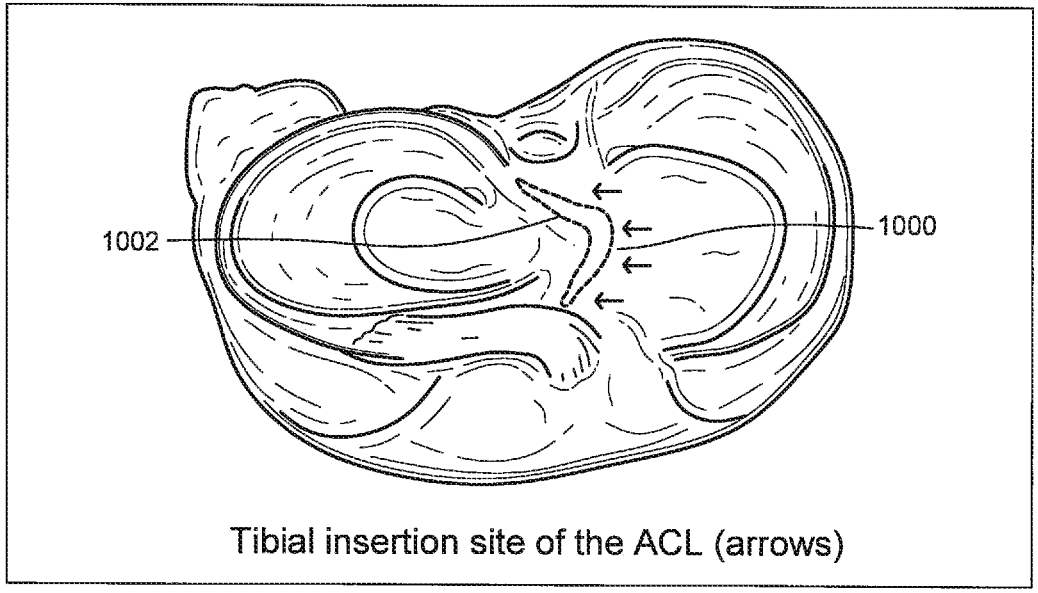
FIG. 1B is a side perspective view of the tibial insertion site of the ACL with the arrows pointing to the insertion site.
Figure 1C:
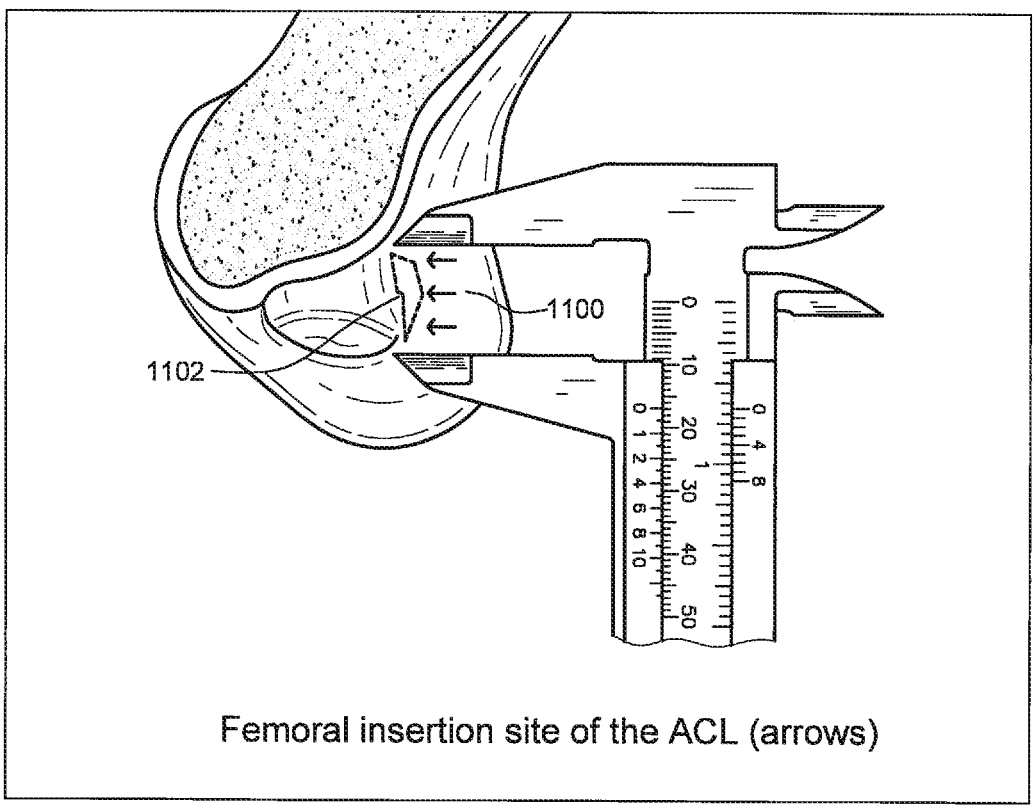
FIG. 1C is a side perspective view of the femoral insertion site of the ACL with the arrows pointing to the insertion site and the caliper illustrating the approximate length of the insertion site.

Referring to FIG. 1A, the native, natural anatomy of the ligament structures within the knee is shown, with special focus on the anterior cruciate ligament (front). In FIG. 1B, the tibial plateau is shown with the tibial insertion site of the anterior cruciate ligament (indicated with arrows). Note the curved (C-shaped) nature of the tibial insertion site 1000 as indicated by the black arrows. The native C-shaped cross section of the tibial insertion site 1000 is identified, and created by the devices, system and method(s) described herein on the tibial plateau or plane. The tibial insertion site 1000, created by the method(s), devices(s) and system, has a substantially planar two dimensional cross section that is substantially C-shaped as in nature. The inner walls created by the device(s), method and system of the tibial insertion site 1000 are substantially smooth so as not to have rough edges that could damage the new, prosthetic ligament that will be resident in the aperture formed by the inner walls and tunnel through the tibia. Referring now to FIG. 1C, the femoral insertion site 1102 of the anterior cruciate ligament (marked with arrows 1100) is shown. Note the flat and ribbon-like nature of the femoral ligament insertion site 1102. Similarly, the inner walls created by the device(s), method and system of the femoral insertion site 1000 are substantially smooth so as not to have rough edges that could damage the new, prosthetic ligament that will be resident in the aperture formed by the inner walls and tunnel through the femur. The femoral insertion site 1102, created by the method(s), devices(s) and system, has a substantially planar two dimensional cross section that is substantially slit-shaped as in nature.

The system, devices and method presented here are intended to allow reconstruction of these ligament structures in a manner that mimics or substantially matches the naturally occurring anatomical ACL in conformation, shape and anchor point attachment design as closely as reasonable possible to the natural or native structures and geometric conformation, e.g. two dimensional geometric conformation and also three dimensional conformation. As opposed to current methods, especially the flat and ribbon shaped nature of the ligament at the insertion sites can be reconstructed with great ease.

The system comprises devices (FIGS. 2A-15D, 16A-16-B, 21A-B, and 22A-22D) and methods (FIGS. 17A-20C) for the creation of the tibial and femoral insertion sites as well as mounting of the prosthetic ligaments, both adapted to the individual, specific anatomy of the patient. It is appreciated that native ligament footprints vary from patient to patient, and that, in one variant of the invention, the one or more bone apertures or tunnels created in the method illustrated (FIG. 20 C) are designed to be customized in size for a respective patient. By way of further example, the bone apertures or tunnels in the damaged knee are created to match or substantially match the ligament attachment footprints 1002, 1102 (FIGS. 1B-1C) that are in an un-damaged knee. The bone apertures or tunnels are created with system 3000 tools 200, 200', 300 (FIGS. 2A-5D), drills (not shown), burrs (not shown), templates, 4003-4005 (FIGS. 4A-4D), 6004-6006 (FIGS. 6A-6D), and other accessories described herein.

The system 3000 (FIG. 24) further includes tools 500 (FIGS. 8A-8I), 550' (FIG. 10A-10E, FIG. 11) 600, 600' (FIGS. 12A-12C) for the preparation of ribbon-like ligaments from multiple tendon bundles or from split tendons that also mimic native ligament structure and function as well as positioning in the damaged joint. The system 3000 comprises tools (FIGS. 2A-15D, 16A-16-B, 21A-B, and 22A-22D) designed for the preparation and simple fixation of both kinds of ribbon-like grafts at the tibial and femoral insertion sites. The use of these devices for the anatomical reconstruction of the ACL is discussed in detail below. Of course, system 3000 includes other tools that are used to enable the system and method described herein that are known to surgeons with expertise in reconstruction procedures.

Device for Creating the Tibial Insertion Site.

Referring to FIGS. 2A-2C, tibial aiming device 200 is presented, which allows precise positioning and creation of a C-shaped tibial tunnel (not shown) by multiple position and anatomical location drilling techniques and procedures at footprints 1002, 1102. The fully assembled device 200 is shown in FIG. 2A, while FIG. 2B depicts the parts, 201-214 which are preferably made from stainless steel, although other metals can also be used that are used for surgical tools. FIG. 2C finally comprises parts 206, 211, 213), which are chosen according to the anatomy of a patient's insertion site. Device 200 consists of an intra-articular 201 and an extra-articular part 202, which are connected via an arc 205 or a similar structure.

The patient specific, custom sized and dimensioned parts of FIG. 2C comprise the intra-articular template 206 which fits into frame 203 of the intra-articular part 201, as well as the corresponding extra-articular drill sleeve 207 fitting into the drill-sleeve mounting 214. The intra-articular template 206 can be chosen according to the anatomy of the insertion site of the patient. Alternatively, the intra-articular template can be fixed (permanently or removable) to arc 205 without the use of frame 203 by using other means of fixation (e.g. slits, etc.). By using the corresponding drill sleeve 207, a drill tunnel is created at insertion sites, which reproduces the tibial insertion site 1002 according to the principles of the invention.

Once the tibial plateau (FIG. 1B) has been cleaned from residuals of the torn ACL (not shown) and the insertion site 1002 has been laid open (FIG. 1B), a tibial intra-articular template 206 can be chosen from a set of different templates according to size and shape of the insertion site to create the desired substantially half-moon or fully half-moon footprint on the tibial plateau. In another variant of the invention, the footprint is a curve or an arch or a linear slit, as required. As a result the corresponding extra-articular drill-sleeve 207 is defined as well. Template and corresponding drill-sleeve are then introduced into frame 203 of the intra-articular template mounting 201 and the extra-articular drill-sleeve mounting 214, respectively. The intra-articular template 206 is positioned over the tibial plateau in such a way, that the opening 213 in the template corresponds to the C-shaped tibial insertion site on the tibial plateau.

Pin 212 on the intra-articular part 201 and guide wires 211 mounted on drill sleeve 207 of the extra-articular part 202 are used to fix the tibial aiming device 200 to the tibia. This can be accomplished by pushing the guide wires towards the tibia, by means of which pin 212 and guide wires 211 will be indented in the intra-articular and the extra-articular parts of the tibia, respectively.

Therefore guide-wires 211 are introduced in the slotted holes 210 of the drill-sleeve 207 and thereby slightly compressed in order to remain fixed unless pushed further in by the surgeon. They can be moved along these holes until they reach the tibia and are anchored within. By fastening screw 204 or similar locking device, the drill-sleeve 207 is compressed and with it the slotted holes 210. Thereby guide-wires 211 and drill-sleeve 207 are simultaneously fixed in drill sleeve mounting 214.

Alternatively, the drill-sleeve itself contains protrusions, spikes or the like which aid in the fixation of the drill sleeve to the tibia (not shown).

Figure 3A:
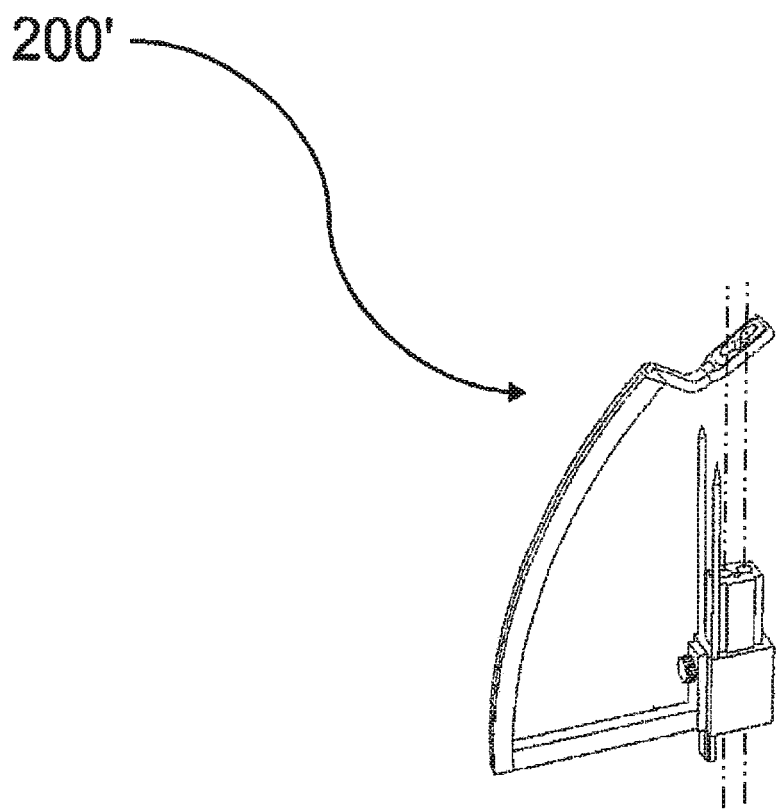
FIG. 3A is a perspective view of a variation of an assembled tibial aiming device.
Figure 3B:
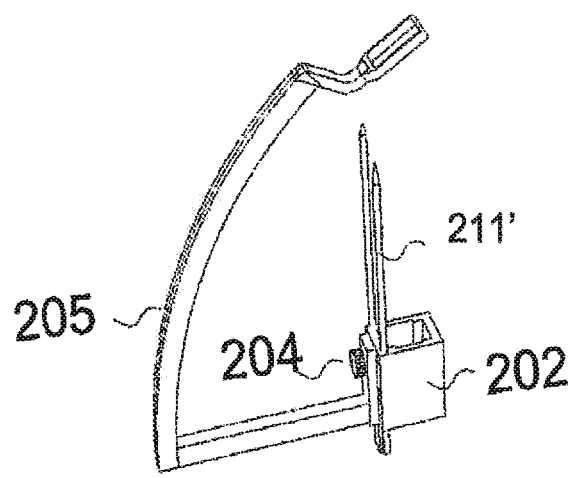
FIG. 3B is a perspective view of a variation of the tibial aiming device without tibial drill templates.
Figure 3C:
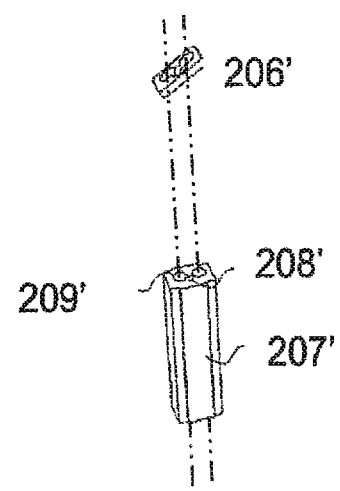
FIG. 3C is a perspective view of a variation of tibial drill templates.

In FIGS. 3A to 3C, variation 200' of tibial aiming device 200 (FIGS. 2A-C) is shown. Here, fixing of the aiming device 200' to the tibia is accomplished by pins 211' (or similar structures), which are attached directly to the drill sleeve mounting 214. These pins 211' can be moved longitudinally together with the drill sleeve mounting, fulfilling the same role as guide-wires 211', except that they cannot be individually adjusted to the patient specific geometry of the tibia. As an alternative to fixed guide wires 211' on drill-sleeve mounting 214, the drill sleeve mounting itself contains protrusions, spikes or the like which aid in the fixation of the drill sleeve to the tibia (not shown).

Guide wire tube 208' (FIG. 3C) allows a guide wire to be driven to the tibial plateau from outside, after the tibial aiming device has been fixed to the tibia. Consecutively, a plurality of bores (in the shown embodiment two) are made by applying drills through drill tunnels 209' of drill sleeve 207'. The tibial aiming device can then be removed while the guide-wire, still being kept in place, is over drilled with a hollow drill. Since the drill bores overlap (overlapping drill bores), a slit is created, which corresponds to the intra-articular template 206' and the tibial insertion site of the ACL, respectively. Cleaning and smoothing of bore edges can be performed optionally by using a drill, bur, rasp, chisel, knife or a similar device.

Alternatively, dilators (not shown), which are of same size and shape like the intended c-shaped tunnel, can be used to compress or dislocate remaining bone structures to achieve the intended smooth surface graft tunnels.

Figure 4A:
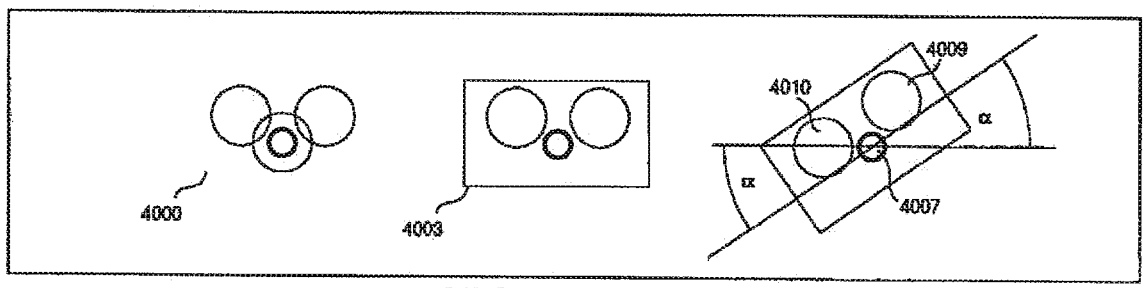
FIGS. 4A to 4C are plan views of exemplary bore configurations with tibial drill-sleeves.
Figure 4B:
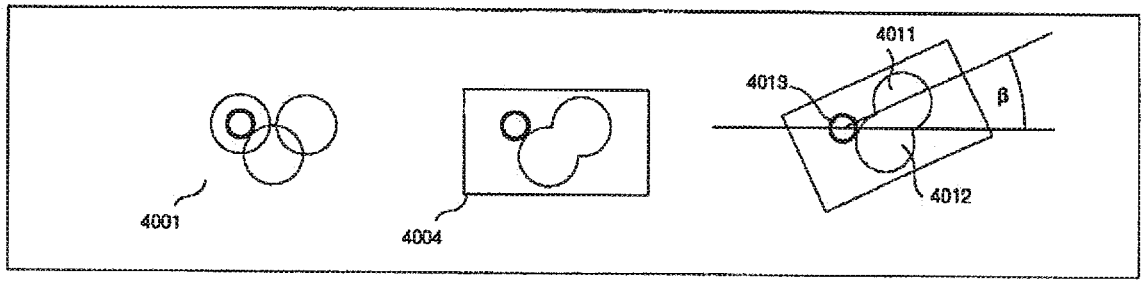
Figure 4C:
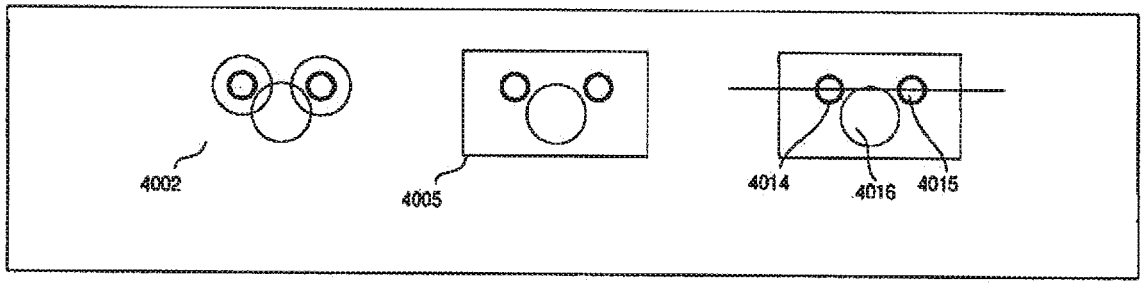

Referring now to FIGS. 4A-4C, different bore-configurations 4000-4002 (first row) with the corresponding tibial drill-sleeves 4003-4005 (second row) are depicted. As shown in FIG. 4A the guide-wire 4007 (indicated as a bold circle) can be in the middle of the two adjacent drill tunnels 4009, 4010. The corresponding drill sleeve has a guide tube for the guide-wire in the center and after setting the guide-wire, the drill sleeve can be adjusted by rotating around the guide wire (depicted in last row, angle α). Another bore configuration is shown in FIG. 4B, where the guiding tube 4013 for the guide-wire (indicated as a bold circle) is placed off-center and the adjacent drill tunnels overlap. With this configuration, where the drill tunnels 4011, 4012 are closer together, smaller and shorter slits can be generated. After setting the guide-wire, adjustment of the final bores can be made by tilting the drill-sleeve around the guide-wire (indicated as angle β). In another configuration (FIG. 4C), the drill sleeve 4005 is fixed by drilling in two guide-wires 4014, 4015 in the lateral guide-wire tubes, followed by drilling the central bore 4016. After drilling, the tibial aiming device is removed The guide-wires, which are still in place, can then be over drilled with a hollow drill. No adjustment of the drill sleeve is possible after setting of the guide-wires here.

Since the guide wire(s) should not be removed before over-drilling, the device is designed in a way, that drill-sleeve 207 and drill sleeve mounting 214 can be detached from frame 203 without dislodging the set k-wire (s). In the shown embodiment, this is accomplished by a design, where drill sleeve mounting 214 and drill sleeve 207 are unlocked from frame 203 and pulled from the guide-wires.

Alternatively, employing the configuration in FIG. 4C, the tibial drill sleeve 4005 can be fixed to the tibia by drilling via the central bore channel 4016 and leaving the drill in the drill hole. The drill stabilizes the drill sleeve 4005 and consecutively (here, by way of example 2) k-wires are drilled through the adjacent k-wire channels. After removing drill sleeve 4005 and drill (not shown), the k-wires are over-drilled, resulting in overlapping bore channels. Of course, it is appreciated that a plurality of k-wire channels and bore channels can be used in various embodiments of the invention, positioned in relation to one another so as to obtain the desired conformation of a respective insertion site.

Device for Creating the Femoral Insertion Site

In FIGS. 5A-5D, femoral aiming device 300 is presented, which aids in precise positioning and creation of the femoral tunnel resembling the femoral insertion site 1100, which is slit shaped or substantially slit shaped. As shown in FIG. 1C, the femoral insertion site 1102 is a straight slit or substantially straight slit with individual patient specific variations in width and length, e.g. two dimensional cross section. It is appreciated that the insertion sites described herein, create a patient specific, naturally occurring insertion site for the reconstructed ACL.

Figure 5A:
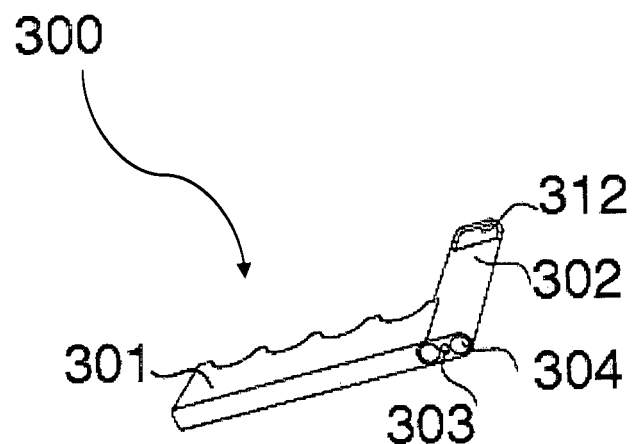
FIG. 5A is a perspective view of a femoral aiming device.
Figure 5B:
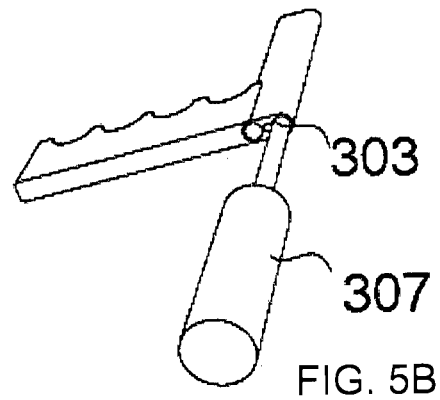
FIG. 5B is a perspective view of a femoral aiming device with mounted arthroscope.

As depicted in FIG. 5A, femoral aiming device 300 consists of handle 301 attached to guiding sleeve 302 with guiding tube 303 for guide wire 305 and adjacent channels 304 for the drill(s). In the present embodiment guiding sleeve 302 contains two drill channels 304. Femoral aiming device 300 may, however, contain just one or more than two drill channels 304, e.g. a plurality of drill tunnels. As shown in FIG. 5B, the femoral aiming device 300 can be equipped with an optional arthrosope 307 to enable direct visualization of the femoral insertion site 1100 and interior of the knee joint. Arthroscope 307 can for example be introduced through a drill channel 304 or any other port (not shown) located nearby. In another embodiment (FIG. 5A and FIG. 5C) guiding tube 302 has openings 312 at the side walls of the tip of the guiding tube, which allow lateral vision of the surgeon to the femoral insertion site 1100.

Figure 5C:
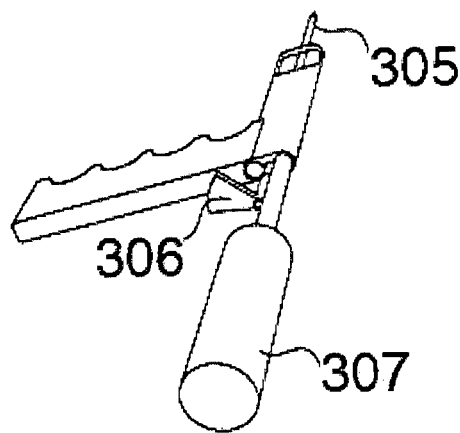
FIG. 5C is a perspective view of a femoral aiming device with mounted arthroscope and aiming aid for placing the guide-wire.
Figure 5D:
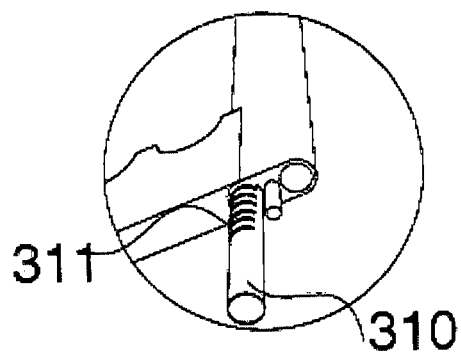
FIG. 5D is a perspective view of depth marks of a drill at the edge of the bore sleeve for measuring the depth of the bores before and during drilling.

As exemplified in FIG. 5C the femoral aiming device 300 can be further equipped with a guide wire 305, holding "stamping" device 306 on its distal end. This stamping device is used to allow a first fixation of the guide wire to the femoral insertion site 1100 by pushing the guide wire into the intra-articular cortex of the femur.

The assembled femoral aiming device (as shown in FIG. 5C) is introduced laterally under direct visualisation employing the arthroscope 307. By using an appropriate arthroscope 307, the guide wire and the femoral insertion site 1100 can both be visualized simultaneously. Positioning of guide wire 305 is furthermore facilitated by guiding device 900 depicted in FIGS. 15A-15D. Once the guide wire is placed in the center of the insertion site, it is fixed by tapping or pushing the "stamping" device 306. Subsequently, stamping device 306 and arthroscope 307 are removed and the guide wire is drilled to the posterior cortex of the femur. Bores (two in the shown embodiment comprising two drill channels or more bores involving a plurality of drill tunnels, although a larger number of bores than two are also contemplated in other variants of the invention) are made by drill 310 guided by drill channels 304 adjacent to the channel holding the guide wire. The depth of the bores can be controlled by reading the depth marks 311 on drill 310 before and during drilling (as detailed in FIG. 5D). As such is it appreciated that the devices, system 3000, and methods described herein provide for variable depth bore holes and limit stops on the devices to control the depth of the drilling. With the help of these depth marks 311, the device 300 can be used to perform drilling through the whole bone to form a uniform tunnel, or it can just be used to create a pocket in the bone or the respective femoral footprints described herein.

After drilling the bores adjacent to the guide wire, the femoral aiming device 300 is removed. The guide-wire, which is still in place, can then be over drilled with a cannulated drill. Since the drill bores overlap, a slit is created, which corresponds to the femoral insertion site 1100 of the ACL (as depicted in FIG. 1C). Cleaning and smoothing of the bore edges can be performed optionally by using a drill, bur, rasp, chisel, knife or a similar device. Alternatively, dilators, which are of same size, dimensional conformation, e.g. 2 dimensional or 3 dimensional, and shape as the intended femoral tunnel, can be used to compress or dislocate remaining bone structures to achieve the intended graft channels (refer to FIG. 23A to 23D).

Figure 6A:
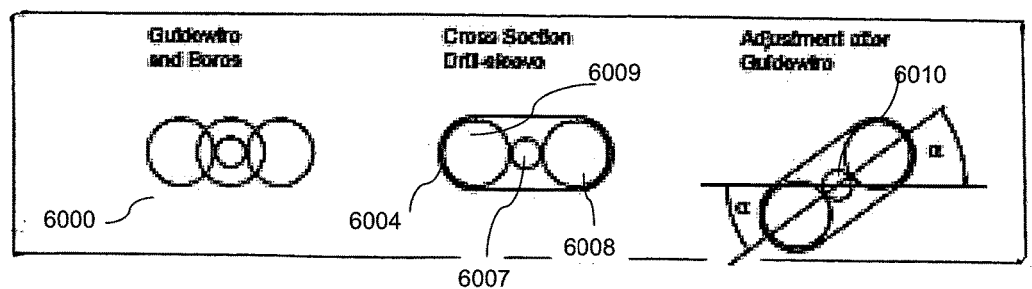
FIGS. 6A to 6C are plan views of different bore-configurations with the femoral drill-sleeves.
Figure 6B:
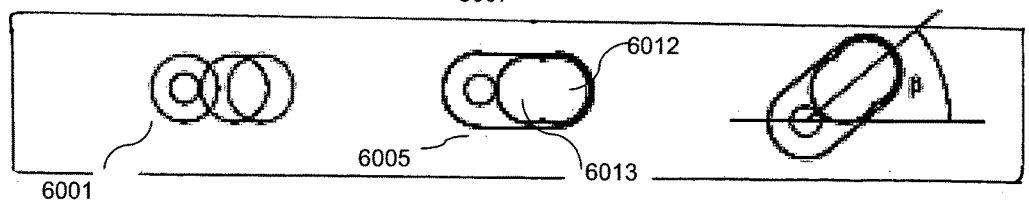
Figure 6C:
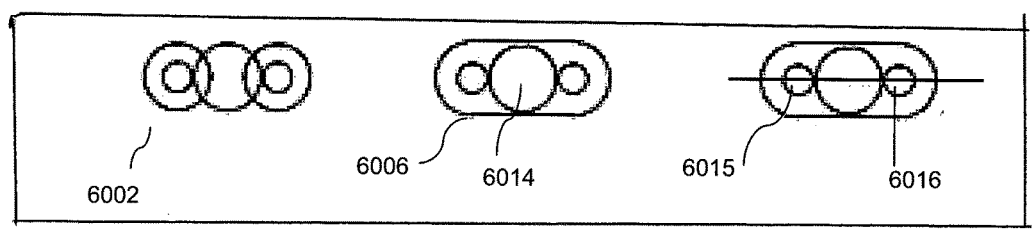

In FIGS. 6A-6C, different bore-configurations 6000-6002 (first row) with the according femoral drill-sleeves 6004-6006 (second row) are depicted. As shown in FIG. 6A, the guide-wire 6007 (indicated as bold circle) can be in the middle of the two adjacent drill tunnels 6008, 6009. The corresponding drill sleeve has a guide tube 6010 for the guide-wire in the center and after setting the guide-wire, the drill sleeve can be adjusted by rotating around the guide-wire (depicted in last row, angle α). Another bore configuration is shown in FIG. 6B, where the guiding tube for the guide-wire (indicated as bold circle) is placed off-center and the adjacent drill tunnels 6012, 6013 overlap. With this configuration, where the drill tunnels 6012, 6013 are closer together, shorter slits can be generated. After setting the guide-wire, adjustment of the final bores can be made by tilting the drill-sleeve around the guide-wire (indicated as angle β).

In another configuration (FIG. 6C), the drill sleeve is fixed by drilling in two guide-wires in the lateral guide-wire tubes, followed by drilling the central bore. After drilling, the femoral aiming device is removed. The guide-wires, which are still in place, can then be over drilled with a hollow drill. No adjustment of the drill sleeve is possible after setting of the guide-wires here. Alternatively, employing configuration 6C, the femoral drill sleeve can be fixed to the tibia by drilling via the central bore channel 6014 and leaving the drill in the drill hole. The drill stabilizes the drill sleeve and consecutively (here 2) k-wires are drilled through the adjacent k-wire channels 6015, 6016. After removing drill sleeve and drill, k-wires are over-drilled, resulting in overlapping bore channels Devices for Graft Preparation and Fixation Using Multiple Tendon Bundles The devices 400, discussed in the following two sections allow for the preparation and fixation of a tendon graft using multiple tendon bundles. These bundles are aligned in a linear manner to resemble the ribbon-like nature of the ligament. As an example, the preparation and fixation of a quadruple graft will be shown.

1) Device for Graft Preparation and Fixation at the Femoral Side of the Multi-Bundle Graft In FIG. 7A, device 400 for femoral tendon attachment and fixation using a quadruple graft is depicted. The device 400 is button-like with elongated body 407, holding sling or loop 401, which is subdivided by at least one partitioning. The fixation of the sling or loop 401 to the elongated body 407 may be accomplished either by passing loop 408, 428 through holes in the elongated body or by fixing the ends of loop- or sling-structure 401 to the elongated body by other means (see detail 411, 421). The partitioning can either be a flexible structure 405 or a bar-like element 425. This partitioning results in at least two "windows" 402, 404, through which the tendon graft is introduced. The partitioning 405 can be either fixed (FIG. 7A, B) or may move along sling or loop 401, as exemplified by bar 425 in FIG. 7C.

The elongated body has furthermore two openings 403, 406 through which pulling cord 409 and a tilting cord 410 can be introduced. Once the tendon (not shown) is attached to the loop or sling structure 401, the elongated body 407 of the button-like device 400 can be pulled through a bone tunnel, until it exits at the extra-osseous side of the bone. By pulling at the tilting cord, the button flips into a position perpendicular to the bore and is thus secured at the extra-osseous side of the bone. A more detailed description of the mode of action may be found in U.S. Pat. No. 5,306,301 to Graf, the entire disclosure of which is hereby incorporated by reference. In contrast to the device presented by Graf et al. in U.S. Pat. No. 5,306,301, device 400 features rigid or flexible partitioning of the loop or sling structure.

Figure 7D:
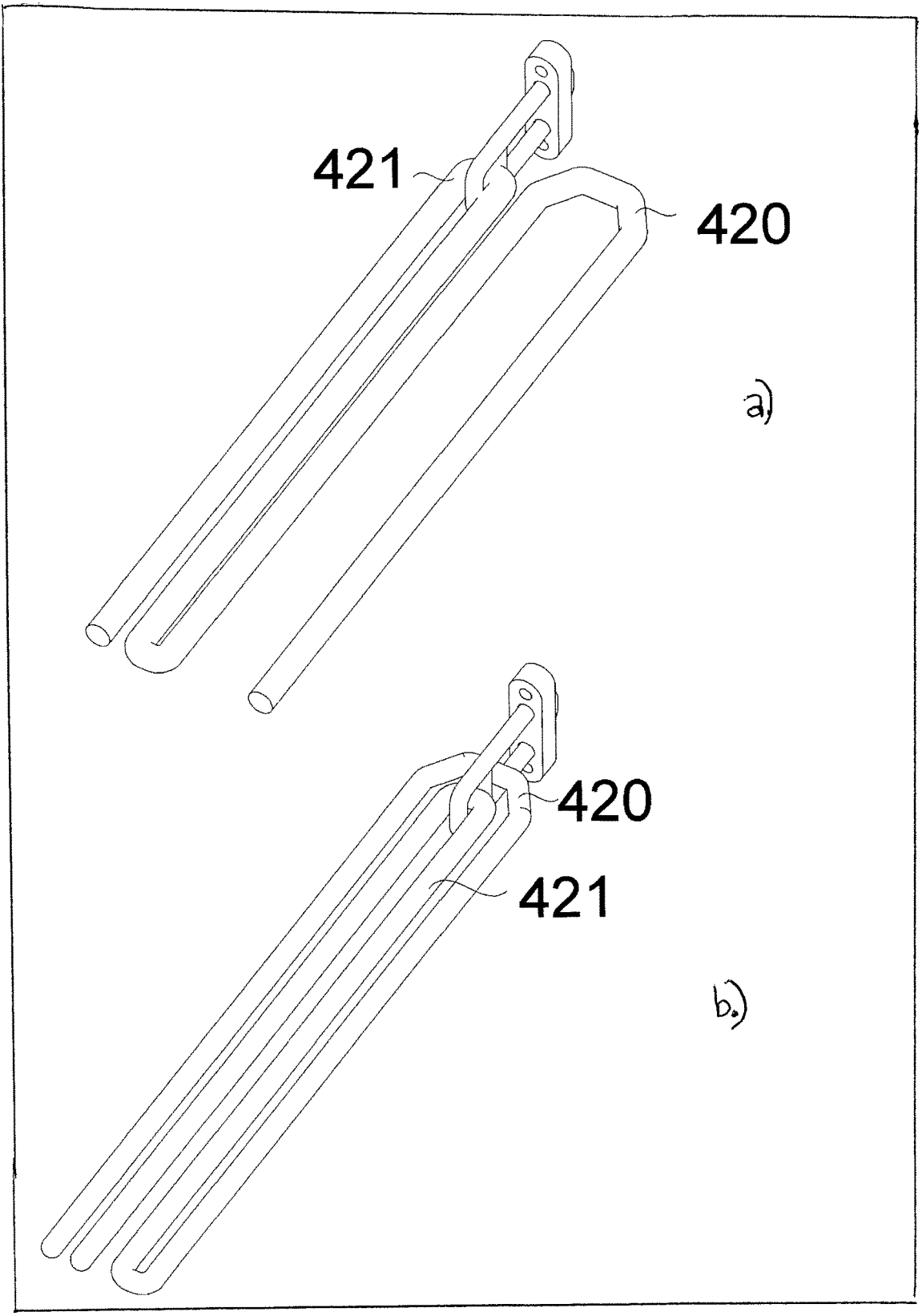
FIG. 7D is a perspective view of a sling and button for femoral tendon attachment and fixation with an inserted quadruple graft.

In FIG. 7D, a first tendon bundle 421 introduced in lower window 404 and a second bundle 420 in higher window 402 remains separated by partitioning 405, 425. Pushing together of the individual tendon strands is thus avoided by the partitioning. Consecutively, the strands of the tendons form a linear alignment, where the lower strand of the tendon holds the upper strand apart. This method allows a ribbon-like arrangement of the individual tendon bundles. They can still be bent in the transverse direction, which is especially important, when the graft has to be passed through a curved (e.g. C-shaped) tunnel.

Furthermore, pushing together of the individual bundles is hindered by the sequential entry of higher 420 and lower 421 tendon strands into the tibial and femoral tunnel. This sequential entry furthermore eases the pulling in of the tendon. This is especially important for cases in which narrow, slit-like tunnels are employed.

2) Device for Graft Preparation at the Tibial Side of the Multi-Bundle Graft

Figure 8A:
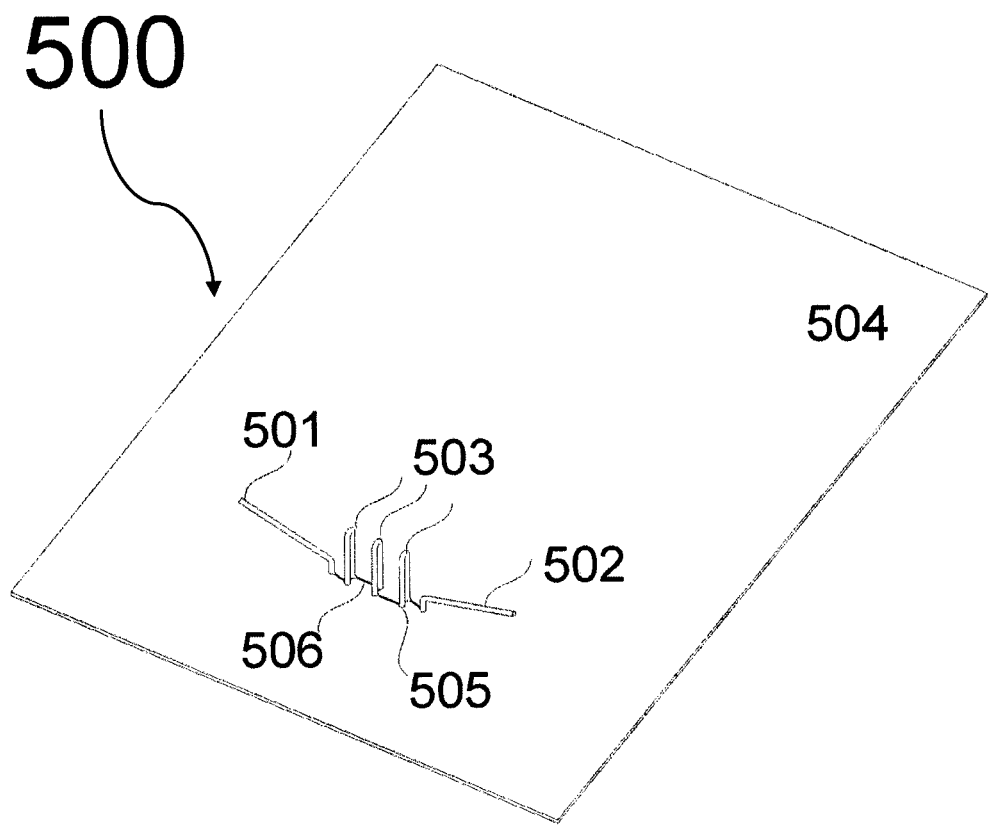
FIG. 8A is a perspective view of a device for tibial tendon attachment and preparation using a quadruple graft.
Figure 8B:
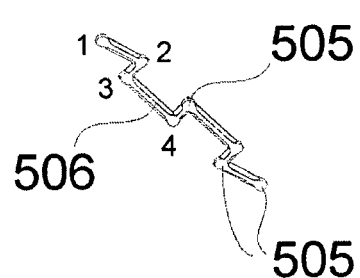
FIG. 8B is a perspective view of the backside of the device with an empty slit.

In FIG. 8A, a device 500 for tibial tendon attachment and preparation using a multi-bundle graft is depicted. Exemplary the attachment and preparation of a quadruple graft is shown. The device 500 consists of base plate 504 with holes 505, which are connected by slits 506. The size of holes 505 is sufficiently large to let cord or suture material 501, 502 pass through. Slits 506 are, however, narrower and allow passing of cord 501, 502 only when it is under a sufficient tensile force, such that the slits are somewhat widened when pulled there through. FIG. 8B details the backside of base plate 504 with holes 505 and slits 506 but without the cord. As depicted, the slit is wider on the backside of base plate 504 which is thin enough to allow the cord to pass when it is subject to a sufficiently high tensile force.

Figure 8C:
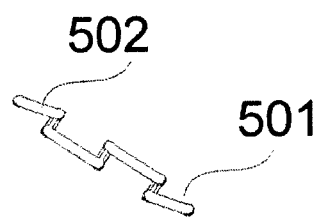
FIG. 8C is a perspective view of the backside of the device with a slit containing a cord.
Figure 8D:
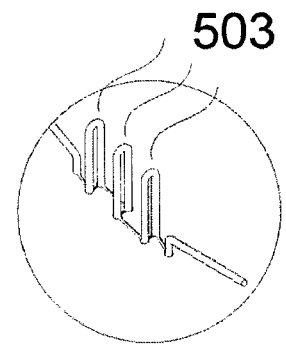
FIG. 8D is a perspective view of the loops of the cord.
Figure 8E:
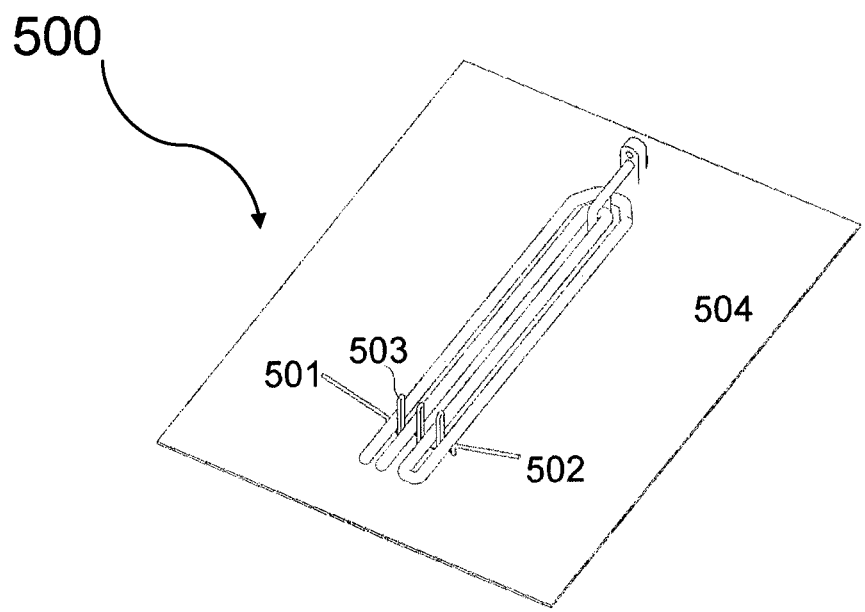
FIG. 8E is a perspective view of the device for tibial tendon attachment using a quadruple graft, with the tendon in place.
Figure 8F:
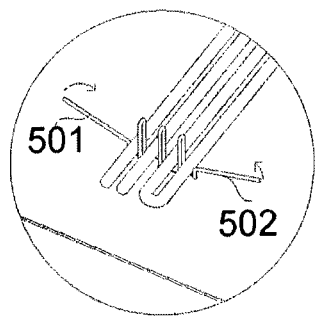
FIGS. 8F-8I are progressive views showing tibial tendon preparation/attachment.

FIG. 8C shows the backside of base plate 504 in the presence of cord 501, 502. On the backside the slit is somewhat wider than on the front, forming channels 507 wide enough to accept the cord. The cord is thus held in channels 507 but cannot pass slits 506 unless subject to a sufficiently high tensile force. Referring now to FIG. 8D, a detailed view of base plate 504 in the presence of the cord is shown. The cord is introduced in the following sequence. Coming from the upper side of the base plate its left pulling end 501 is fed through hole 1. The cord segment between holes 1 and 2 lies in channel 507 on the backside of the base plate. The cord is fed through hole 2 to the front side of the base plate and then back again through hole 3 thus forming loop 503. The segment between holes 3 and 4 lies again in channel 507 on the backside of the base plate, and so on. With this procedure, a structure is created, where pulling ends 501, 502 of the cord as well as loops 503 are on the front side of the base plate, while the connecting sections of the cord are on the backside of the base plate.

Figure 8G:
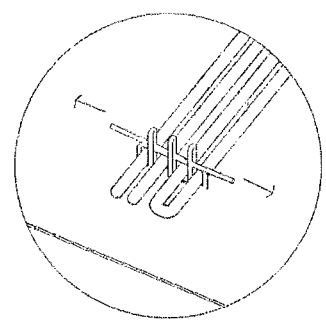
Figure 8H:
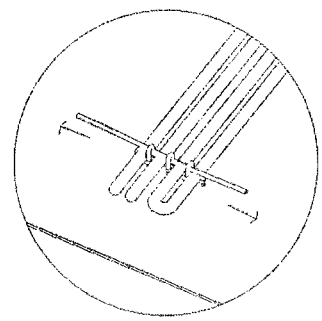
Figure 8I:
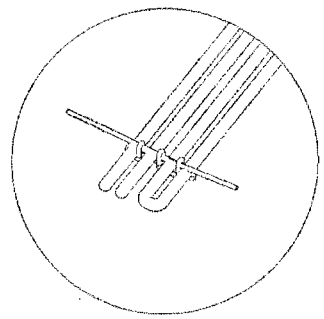

The illustration of FIG. 8A shows an embodiment with 3 loops 503 for the preparation of 4 individual (tendon-) bundles. Other embodiments of the invention comprise a plurality of bundles, e.g. greater or lesser numbers of bundles with a correspondingly varying number of loops 503. Referring now to the sequence of FIGS. 8E to 8I, the formation of a ribbon-like tendon is shown by making use of base plate 504 with cord 501, 502 arranged in loops 503. In a first step, the four strands of the tendon are arranged in the manner shown in FIG. 8E, in which every strand is separated by a loop. In a second step detailed in FIG. 8F, the left pulling end 501 of the cord is to folded over and fed above the tendon through loops 503 to the right side. Meanwhile, the right pulling end 502 is passed in the opposite direction over the tendon through the loops to the left side. By pulling ends 501 and 502 of the cord, the loops are pulled towards the base plate and the tendon (FIG. 8G). By further pulling, the tendon is compressed and thereby fixed (FIG. 8H). Finally, under the application of a sufficiently high tensile force, the cord slips through slits 506 of the base plate and the linear tendon/cord construct is released from the same (FIG. 8I). The resulting structure can be further secured by "weaving" the ends of the pulling cords above and under the individual strands of the tendon or by stitching the pulling cords through the tendon from the left to the right side and vice versa.

With this procedure, a linear mounting for the tibial side of a multi-bundle graft is formed, where the individual strands are pressed together, but cannot slip over each other, thereby avoiding a bulky graft to form. This is especially important in the case where slit-like tunnels with a small width are employed. Another advantage over other graft preparation methods is, that the bone tendon interface is as big as possible and that the prepared graft can be bent, which is especially important, when bone tunnels with bent (e.g. C-Shaped) cross sections are used for graft insertion.

3) Device 1 for Tibial Fixation of the Multi-Bundle Graft

Figure 9A:
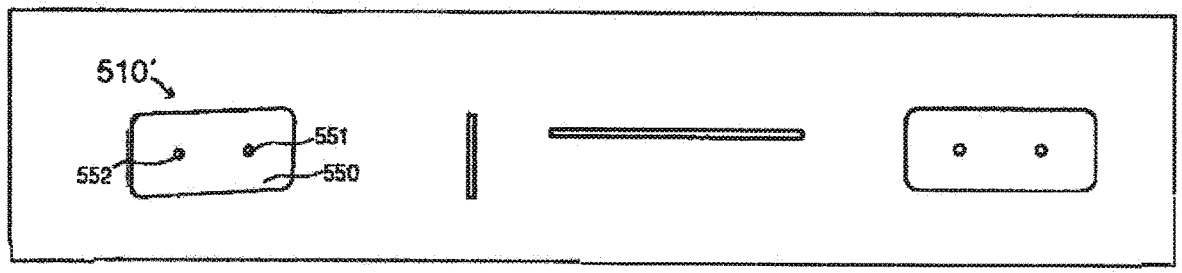
FIG. 9A to FIG. 9D show four different examples of devices for extra-osseous fixation of the tendon graft, which is attached to two cords or sutures; each FIG. 9A to 9D example depicting an alternate embodiment of the device.
Figure 9B:
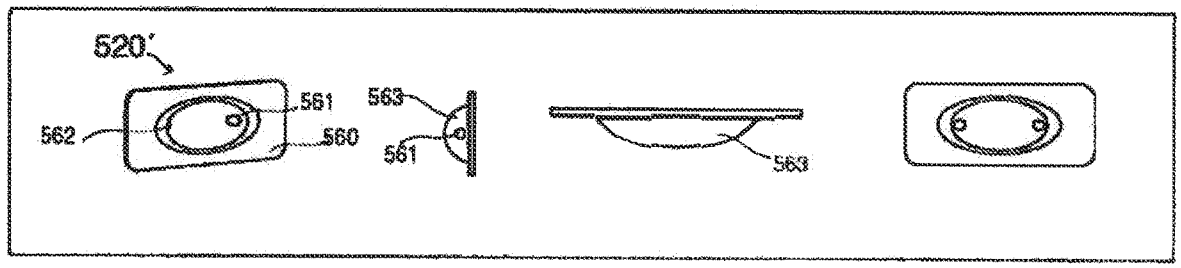
Figure 9C:
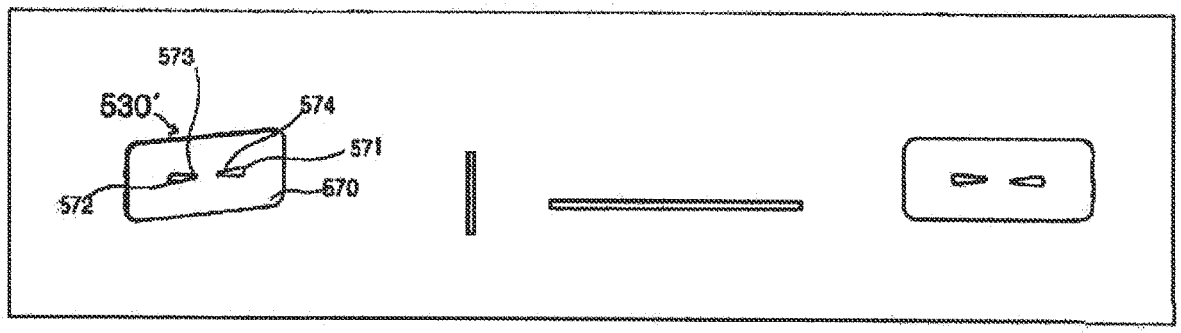

The prepared tendon graft has to be secured at the exit of the tibial tunnel. This can be achieved by an extra-osseous elements 510', 520', 530' and/or 540', which fixes the cords coming from the graft. Usually two cords are used, which can but need not be identical to pulling ends 501, 502, but the devices shown below can also be adapted to usage of more cords. Referring now to FIGS. 9A-9D, a series of embodiments of a device 510', 520', 530' and/or 540' for extra-osseous fixation of the tendon graft is shown. The graft is attached to two (or more) cords or sutures. Referring now to FIG. 9A, device 510' has a flat rigid body 550, which is bigger or larger than the created bone tunnels and has two openings 551, 552 to accept the cords attached to the graft. The cords are passed through openings 551, 552 and the graft can be fixed by tying the cords in a knot. Referring now to FIG. 9B, device 520' has depression 563 in flat rigid body 560. Depression 563 has the purpose of accepting the knot tied between the cords fed through openings 561, 562. The protrusion of the knot into the soft tissue surrounding the bone is therefore minimized. Referring now to FIG. 9C, device 530' has non-circular openings 571, 572 with narrow regions 573, 574 facing the center of the device. This results in wedging of the cords before the knot is tied, preventing loosening of the tension applied to the graft during tying of the knot.

Figure 9D:
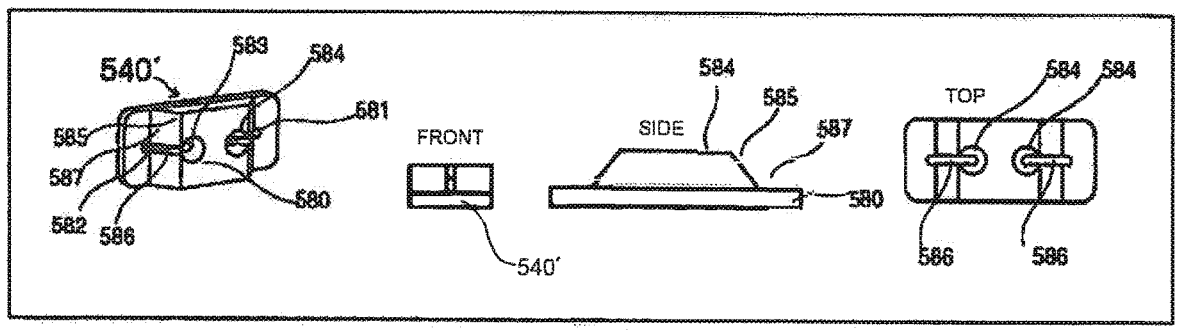

In FIG. 9D, device 540' has flat rigid body 580 featuring sloped extension 585 at the far side of the graft. Furthermore, body 580 with its sloped extension 585 features two slits 586, through which the cords are fed. Then the cords are secured by making knots on each individual cord at position 587 close to the rise of sloped extension 585. The knots are made large enough in order not to pass slits 586. After knotting, the cords can be further tensioned by pulling them over the slope of sloped extension 585 to securing position 584 more distant from the graft.

4) Device 2 for Tibial Fixation of the Multi-Bundle Graft

Referring now to FIGS. 10A-10E, device 550' fixes the two cords coming from the graft by wedging them between an inner turning member and its corresponding casing. Base plate 523 is large enough to bridge the bores of the tunnel. It holds the casing/sleeve 522 for central fastening member 519, which can be rotated around its central axis. Furthermore, the device features two openings 528, 529, shared by sleeve 522 and fastening member 519. Openings 528, 529 allow feeding of the two cords from the intra-osseous side 521 to the extra-osseous side 520 in its open or unlocked position. By turning fastening member 519 the cords can be locked by wedging them between sleeve 522 and the fastening member as will now be explained in greater detail.

Figure 10A:
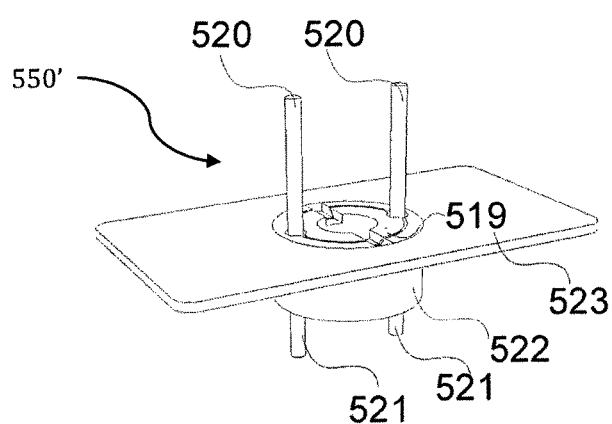
FIG. 10A shows a perspective view for an extra-osseous fixation device in its open state.
Figure 10B:
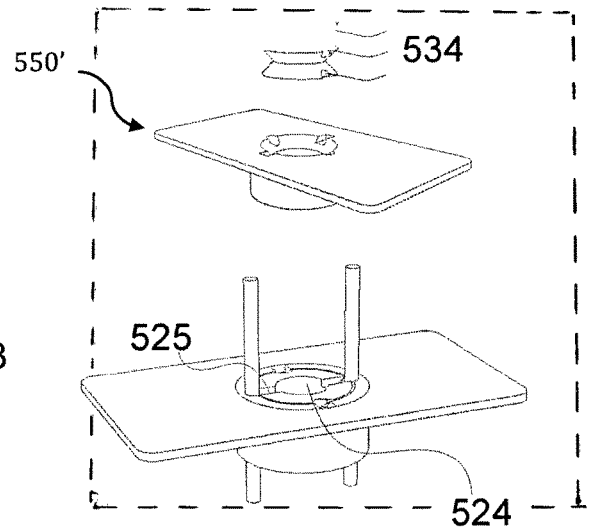
FIG. 10B shows a perspective view for an extra-osseous fixation device in its closed state. Upper drawing depicts an exploded perspective view of the device.

In FIG. 10A, a perspective view of the device is shown in its open state in which the cords can pass through openings 528, 529. In FIG. 10B, a perspective view of the device in its closed state is shown (below). The upper drawing of FIG. 10B depicts an exploded perspective view of the device. The body of fastening member 519 has a jagged appearance 537 resembling the threads of a screw with cut outs 534 of preferably half-cylindrical shape, corresponding to openings 528, 529. The cords are fixed by turning inner fastening member 519 relative to outer sleeve 522. Rotation of the inner fastening member results in displacing its cut outs from the openings in the sleeve, whereby the cords are compressed between the jagged inner fastening member and wall 533 of sleeve 522. Preferably, the angle of rotation is chosen in a way to align the extra-osseous side 520 of the cords with grooves 525 on fastening member 519. As shown below (FIG. 11), this facilitates minimal protrusion of the knotted cords into the surrounding tissue and avoids the unintentional unlocking of the device.

Figure 10C:
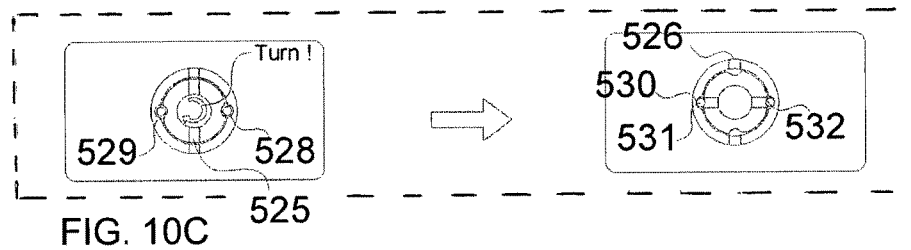
FIG. 10C shows a top view of open (left) versus locked (right) device.

For clarity, a top view of the device is shown in its open (left) and closed state (right) in FIG. 10C. As can be seen, the cut outs of inner turning member 534 are dislocated from openings 528 529 by turning, thereby wedging the cords 520 between turning member and its corresponding casing.

Figure 10D:
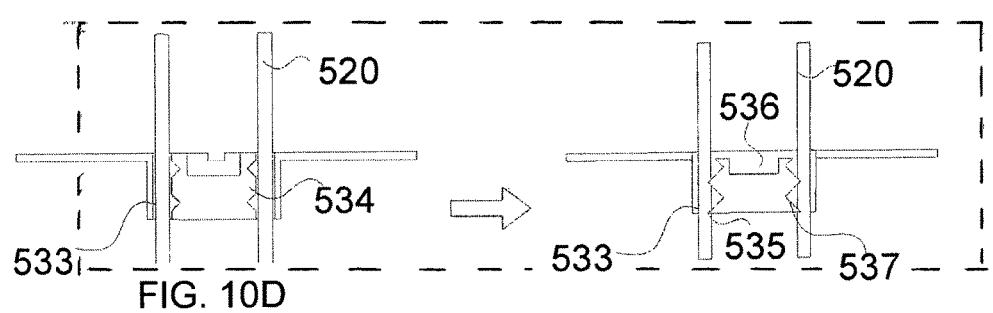
FIG. 10D shows a cross section of open (left) versus locked (right) device.

In FIG. 10D, a cross section of the device in its open (left) and closed (right) state is shown. As evident, cords 520 can pass freely in the open state, while they get blocked by inner turning member 519, (which has a jagged appearance 537 in this variant of the device) upon locking of the device.

Figure 10E:
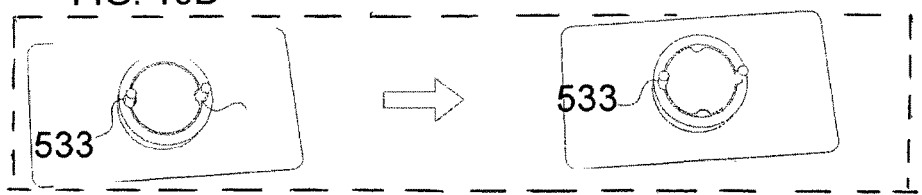
FIG. 10E shows a bottom view of open (left) versus locked (right) device

In one variant, inner fastening member 519 is a screw which facilitates its introduction into sleeve 522 during assembly. Other designs, e.g. cylindrical structures with jagged outer surfaces are possible as well, as long as the cords get locked upon dislocation of the corresponding cut outs. Moreover, the jagged appearance of the surfaces of the inner fastening member and the sleeve are exemplary only. Rounded structures may serve as well in locking the cords by wedging. Cut outs 534 corresponding to the sections of openings 528, 529 on inner fastening member 519 may be of a shape that the initial turning of the inner turning member is facilitated. FIG. 10E is a bottom view of the device, illustrating open (left) and closed state (right).

Figure 11:
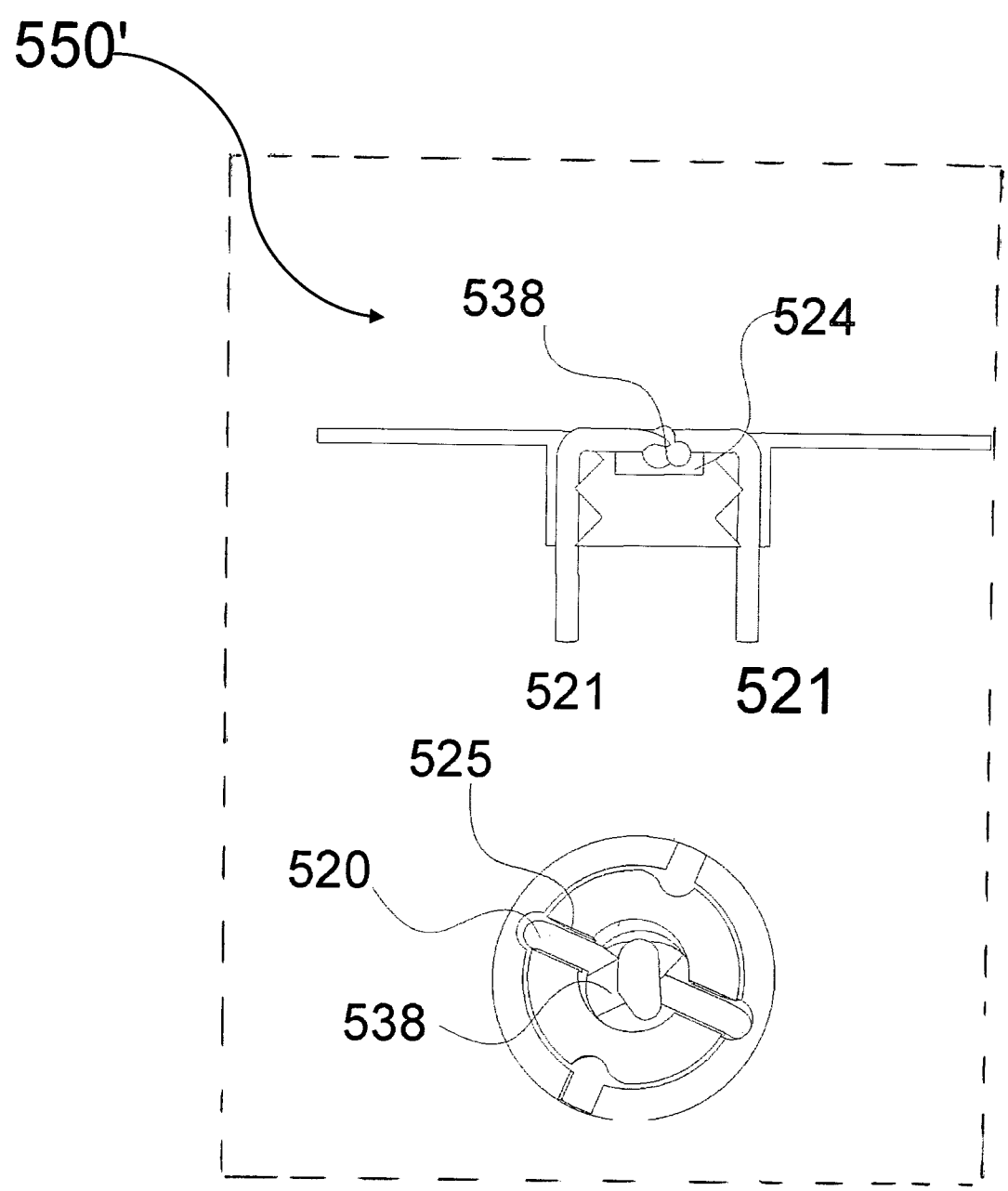
FIG. 11 shows perspective views of a device for extra-osseous fixation of the tendon graft, where the knot of the cords can be hidden in a countersink in the device.

In FIG. 11, device 550' is shown with inserted and knotted cords 520. Grooves 525, along with central depression 524 in fastening member 519 assure minimal protrusion of knot 538 into the surrounding tissue region in a way similar to device 520'.

Devices for Graft Preparation and Fixation Using the Split Tendon Technique

In the following two sections, devices 600, 600' for the preparation and fixation of grafts are described, which reconstruct the ribbon-like nature of the ligament using the split tendon technique. As an example, the application to the anterior cruciate ligament is again shown.

In contrast to the ligament it should replace, the harvested tendon, which is currently used for reconstruction has a round cross section. In order to create a flat, ribbon-like structure, the cylindrical tendon needs to be incised along its length, preferably to a depth on the order of half its diameter. Subsequently, the tendon can be unfolded along the cut, whereby the desired ribbon-like morphology is produced. The incision can be accomplished by a knife, a sharp spoon or any similar tool. Longitudinal cutting of the tendon, with minimal destruction of the parallel tendon fibres, is essential since this could negatively influence the stability of the graft. Furthermore, the device should have means to avoid completely cutting or splitting of the tendon, since this could again negatively influence stability of the graft. The devices presented below exemplify the creation and use of ribbon-like structure from single harvested tendons and are only examples of devices that are used.

1) Device for Tendon Splitting

In FIG. 12A-12C, device 600 is presented, which allows the preparation of a flat graft from a cylindrical graft. As exemplified in FIG. 12A, device 600 has base plate 601 with elevated region 615 over which slider 604 with attached cutting unit 606 can be moved longitudinally in the direction of arrow 611. Cylindrical tendon 608 is placed in groove 602 of elevated region 615 and fixed distally with yoke 607 crossing elevated region 615. Yoke 607 itself may for instance be fixed at the sides 616 of elevated region 615 for example by screws 603. Cutting unit 606 cuts the cylindrical tendon longitudinally when slider 604 is moved along the base plate. The position of yoke 607 can be adjusted to the length of the graft (see arrow 610).

The incision can be accomplished by using a knife, sharp spoon or anything the like. A detail of cylindrical graft 608 and cutting unit 606 is shown in FIG. 12B. Preferably, cutting of the tendon is performed with a single use surgical blade 606, which can be attached via a standardized surgical blade adaptor 605. Longitudinal cutting of the tendon with minimal destruction of the parallel tendon fibres is essential since this could negatively influence the stability of the graft. Furthermore, measuring portions of the device avoid complete cutting of the tendon, by providing a stable offset of the cutting device from the base plate.

In another embodiment, exemplified in FIG. 12C, graft 608 is moved in its longitudinal direction through device 600' with stationary cutting unit 606. As shown, cylindrical graft 608 slides inside bore 614 in structure 612 which is rigidly connected to mounting 605, 613 of cutting unit 606. Cutting unit 606 is positioned in a way to allow longitudinal cutting of cylindrical tendon 608 approximately down to its axis 609. The cutting of the tendon can be performed with a single use surgical blade 606, which can be attached via a standardized surgical blade adaptor 605.

2) Device for Femoral Fixation of Split Tendon Grafts

Figure 13A:
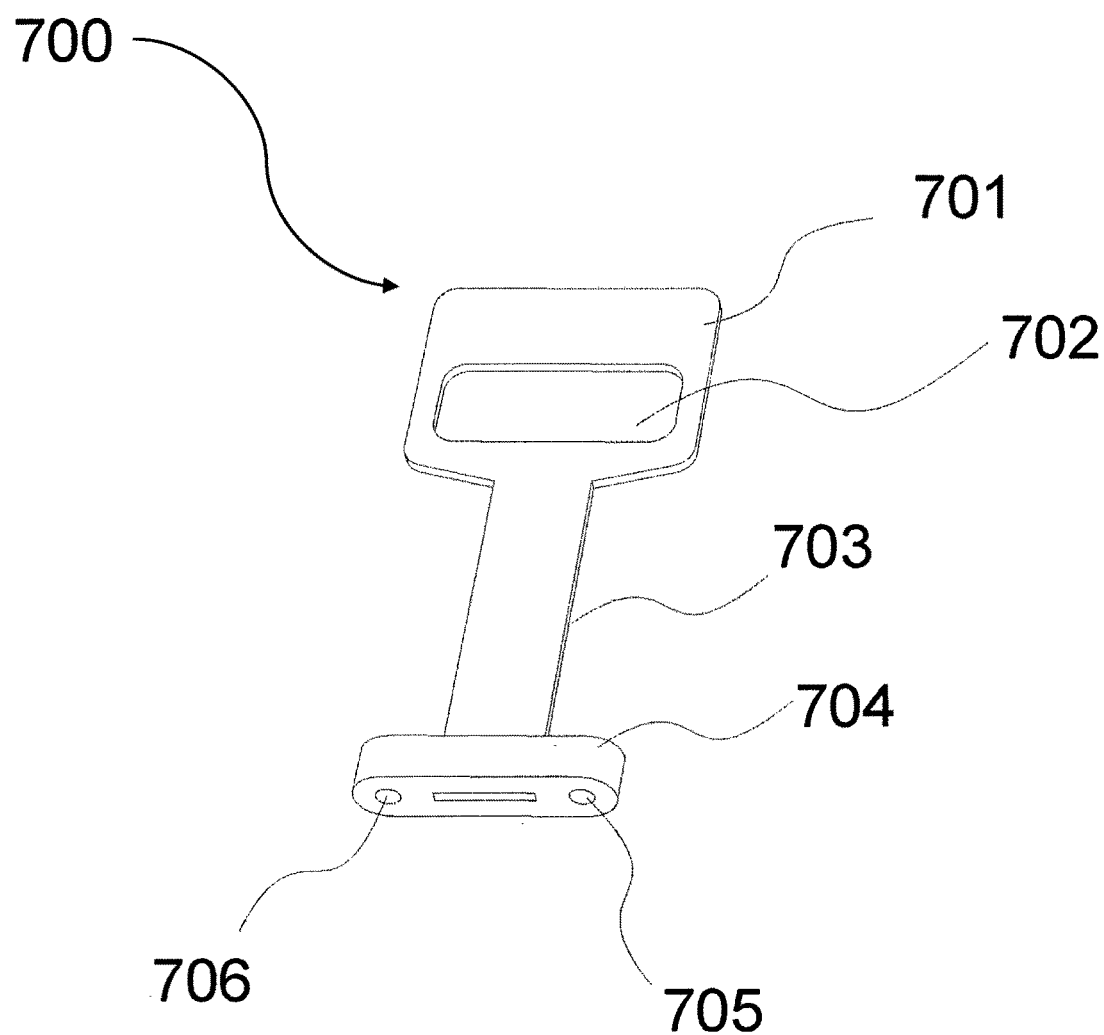
FIG. 13A is a perspective view of the device for femoral tendon attachment and fixation using a ribbon-like tendon graft.
Figure 13B:
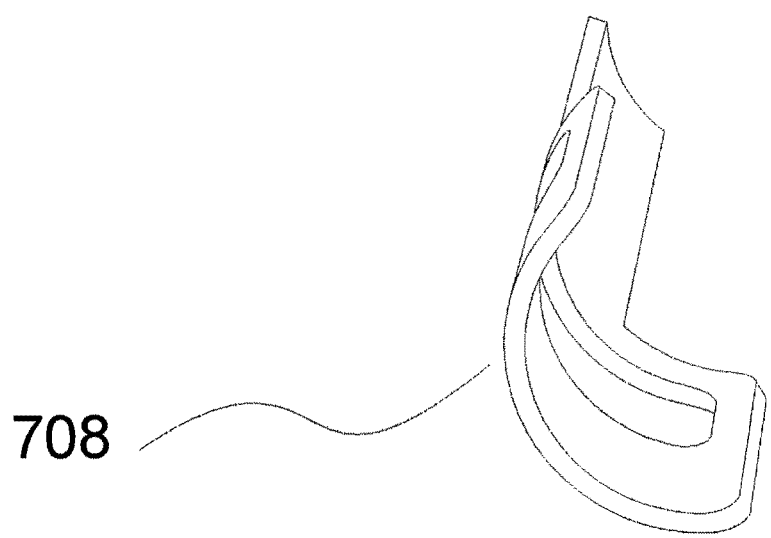
FIG. 13B is a perspective view of bent tape for easier introduction in the tibial and femoral tunnel.

Referring now to FIG. 13A a detailed view of device 700 for femoral tendon attachment and fixation using a ribbon-like tendon graft is presented. The device is a button-like device with elongated body 704 holding tape 703. Tape 703 contains elongated window 702. Adjacent to window 702 is tape area 701, which is utilized for sewing the ribbon-like graft to the tape. Furthermore elongated body 704 has two openings 705, 706, through which a pulling cord and a tilting cord can be introduced, similar to the way described in FIG. 7A. Once the tendon is attached to the tape, elongated body 704 of the button-like device can be pulled through the bone tunnel, until it exits at the extra-osseous side of the bone. By pulling on the tilting cord, the button flips into a direction perpendicular to the bore, thereby being secured at the extra-osseous side of the bone. A more detailed description of the mode of action may be found in U.S. Pat. No. 5,306,301 to Graf, the entire enclosure of which is hereby incorporated by reference. In contrast to the device presented by Graf et al. in U.S. Pat. No. 5,306,301, the device presented here features a slim tape structure to avoid bulking of the tendon, when the construct is pulled through the femoral and tibial tunnel. Furthermore, it features stitching area 701, used for the fixation of the flat tendon in a planar way across its entire width spanning the length of window 702. With this proceeding, a semi-rigid structure is formed, where the tendon graft cannot slip together, while bending in the transverse direction is still possible as shown in FIG. 13B. The possibility of tape area 701 to bend is important, since the tape has first to pass the C-shaped tibial channel before being drawn into the femoral channel.

The tape-structure of device 700 depicted in FIGS. 13A-13B is exemplary only. Other embodiments of the device may employ a stitching area attached to a loop or a sling. Further variations of loop or tape structures, which allow a ribbon like attachment of the tendon to the fixation device, are shown in FIG. 13C.

Figure 13C:
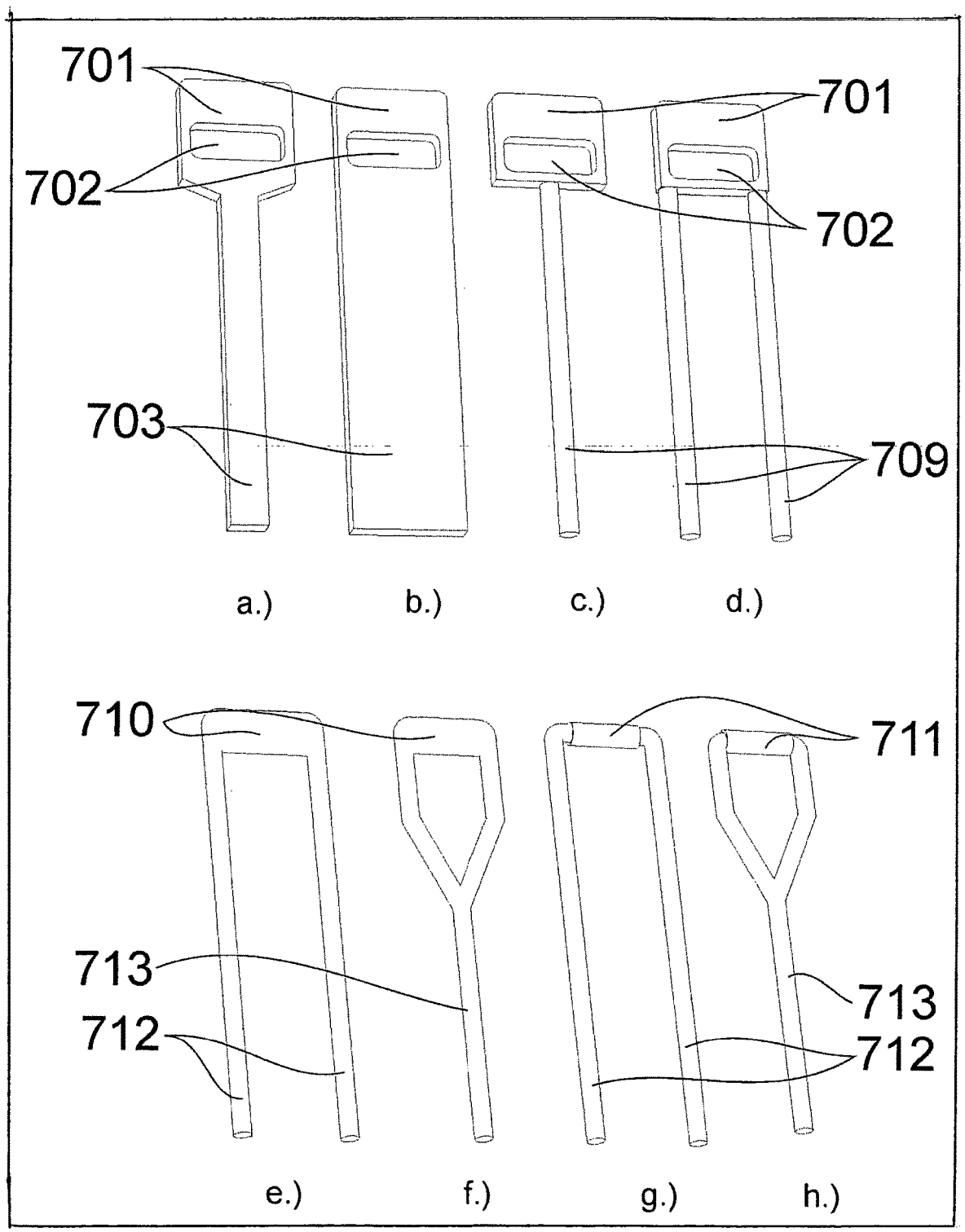
FIG. 13C show perspective views of various alternate embodiments of the element which holds the tendon.

In FIG. 13C (embodiments a.) to d.)), the element holding the tendon is a tape-like structure with window 702 and adjacent stitching area 701 as described above. Appliances linking this structure to elongated body 704 may be tape-like 703 or round structures 709, for example cords. Referring now to FIG. 13C, embodiment e.) and f.), the element holding the tendon is a structure, where the area 710 over which the tendon is placed is thickened by additional strands of material to stiffen said area and/or provide a stitching area as described above. Appliances linking structure 710 to elongated body 704 may be round structures, for example cords, with one 713 or two legs 712.

In FIG. 13C, embodiments g.) and h.), the area over which the tendon is placed is stiffened by tube 711, which is preferably semi-rigid to allow an easy pulling-in of the structure through the tibial and femoral tunnel. Appliances linking this area to elongated body 704 may be round structures, for example cords, with one 713 or two legs 712.

Alternatively, the stitching area is a flag-like structure 755, which is attached to and can move on a cord 750. Preferably, this structure is made of a textile or a mesh, which has openings at the side or in its corners, that allows the passing of a suture/cord (FIG. 13C, i.).

Figure 13D:
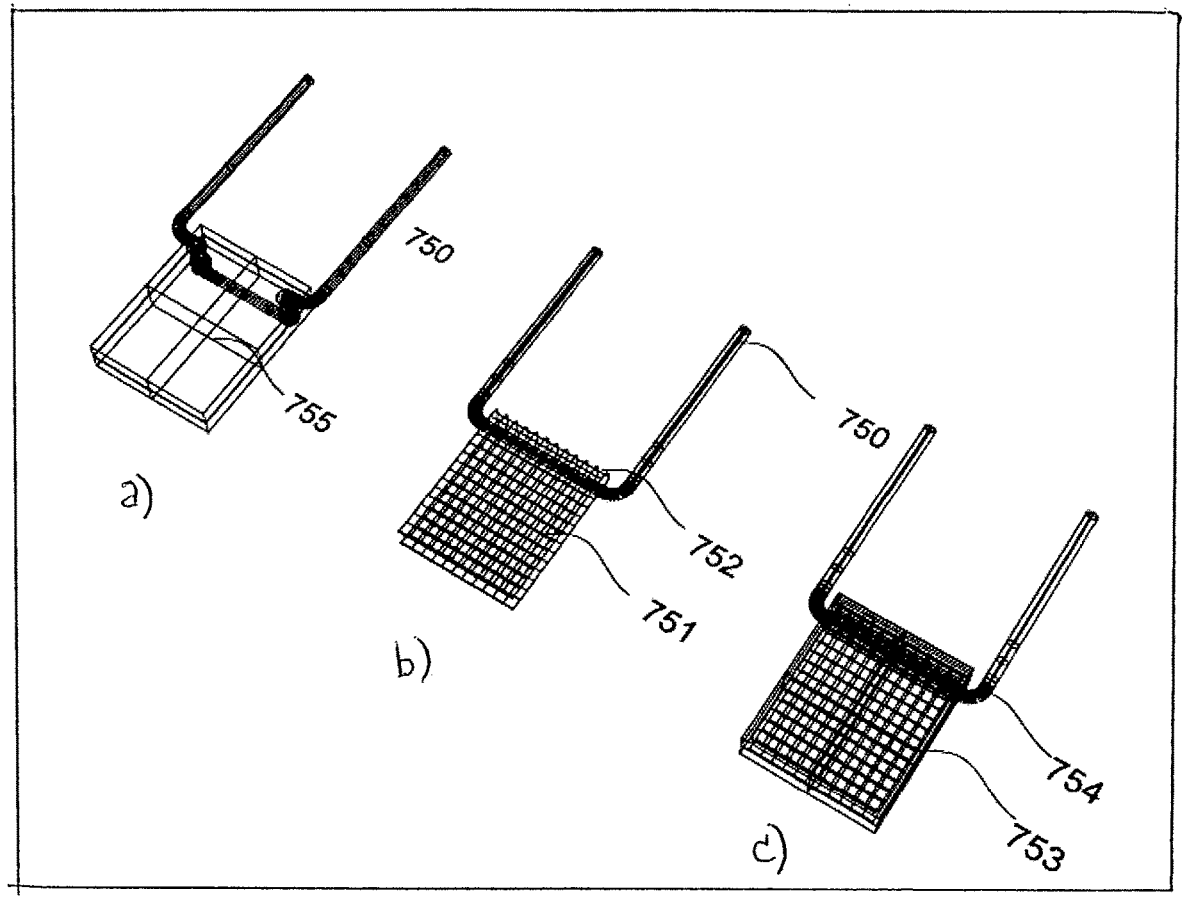
FIG. 13D shows perspective views of a mesh bent over a suture and fixed by stitching or molding the bent mesh in a matrix.

Also, a mesh can be bent over the suture and fixed by stitching or molding the bent mesh in a matrix (e.g. silicone, FIG. 13D, embodiments b.), c.)), whereby the cord protrudes at each side of the flag (at position 754). In FIG. 13D, embodiment b.), a mesh 751, which is bent over the cord 750 is shown. In FIG. 13D, embodiment c.), the mesh is moulded in a matrix 753, which allows a precise modulation of the stiffness of the flag structure by employing different matrices.

3) Device for Tibial Fixation of Split Tendon Grafts

Figures 14A, 14B, 14C:
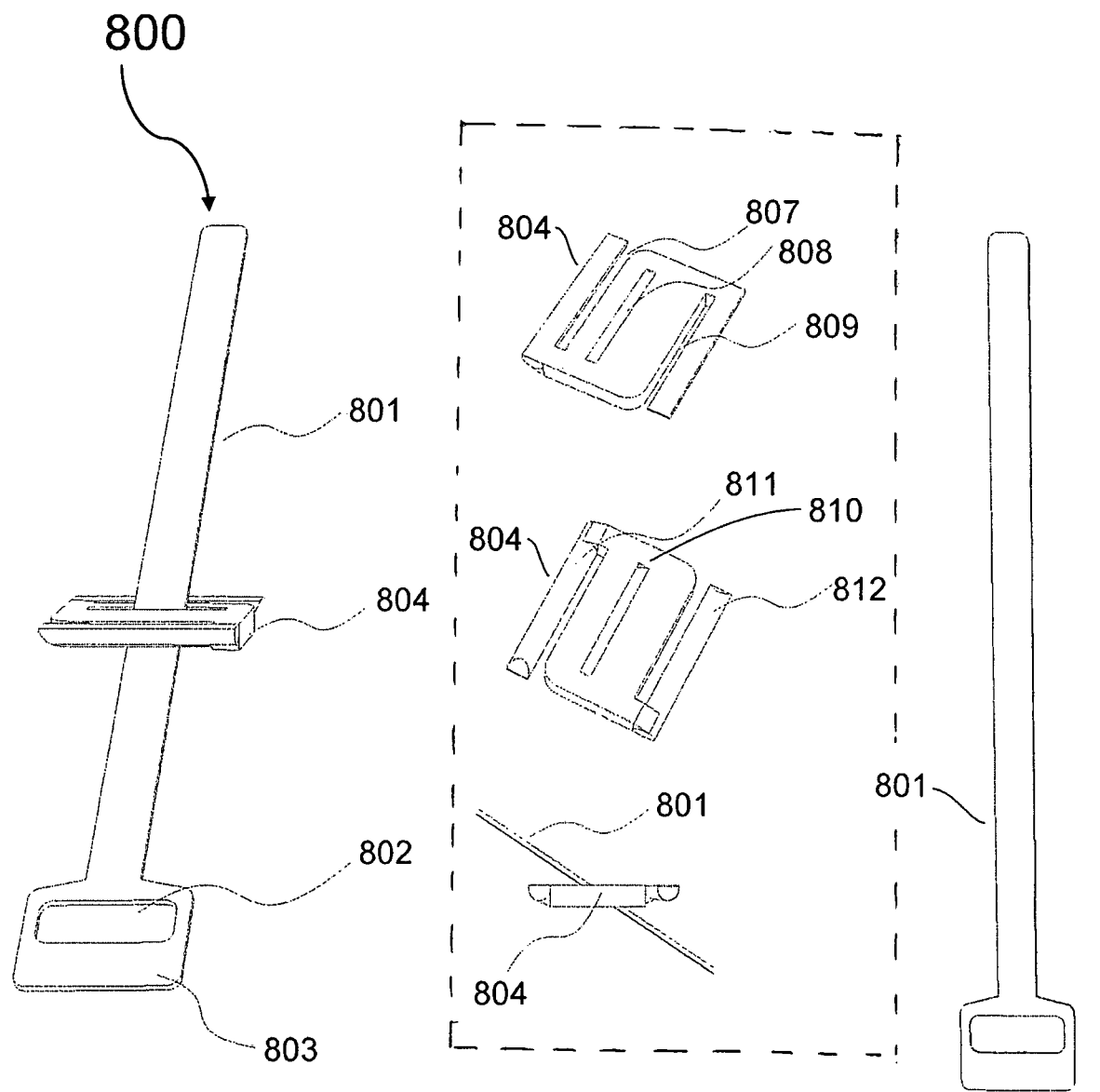
FIG. 14A is a perspective view of an assembled device for tibial tendon attachment and fixation using a ribbon-like tendon graft.
FIG. 14B are perspective views of the fixing device for tibial tendon fixation using a ribbon-like tendon graft (extra-osseous element).
FIG. 14C is a plan view of the element for tendon attachment.

Referring now to FIG. 14A, assembled device 800 for tibial tendon attachment and fixation using a ribbon-like tendon graft is presented. Analogous to the femoral attachment device, the device 800 features tape 801 with window 802 and stitching area 803. Fixing device 804 has the purpose of fixing the tape at the exit of the tibial tunnel. It comprises slit 808 designed to let tape 801 pass through. This fixing device has an upper and a lower surface and slit 808 is inclined to these surfaces (see last drawing of FIG. 14B). The tape 801 therefore passes through fixing device 804 at an angle. Referring now to FIG. 14B the extra-osseous element of fixing device 804 for tibial tendon fixation using a ribbon-like tendon graft is depicted in more detail. The first drawing shows the device from above, with inclined slit 808 and two adjacent slits 807, 809 which are open on one side. The openings can be on the same or on opposing sides (as depicted) of device 804. The second drawing shows the device 800 from below. Note that opening 810 of slit 808 is shifted with respect to that on the upper side. This is due to the inclination of the slit, visible in greater detail in the last drawing of FIG. 14B, where tape and fixing device are both shown. FIG. 14C shows a preferred embodiment of tape structure 801. Other variations, such as a tape with constant width, can be used as well. FIG. 14C shows the preferred embodiment of said tape structure (801), but also variations as described under FIG. 13C can be used with this system.

Figure 14D:
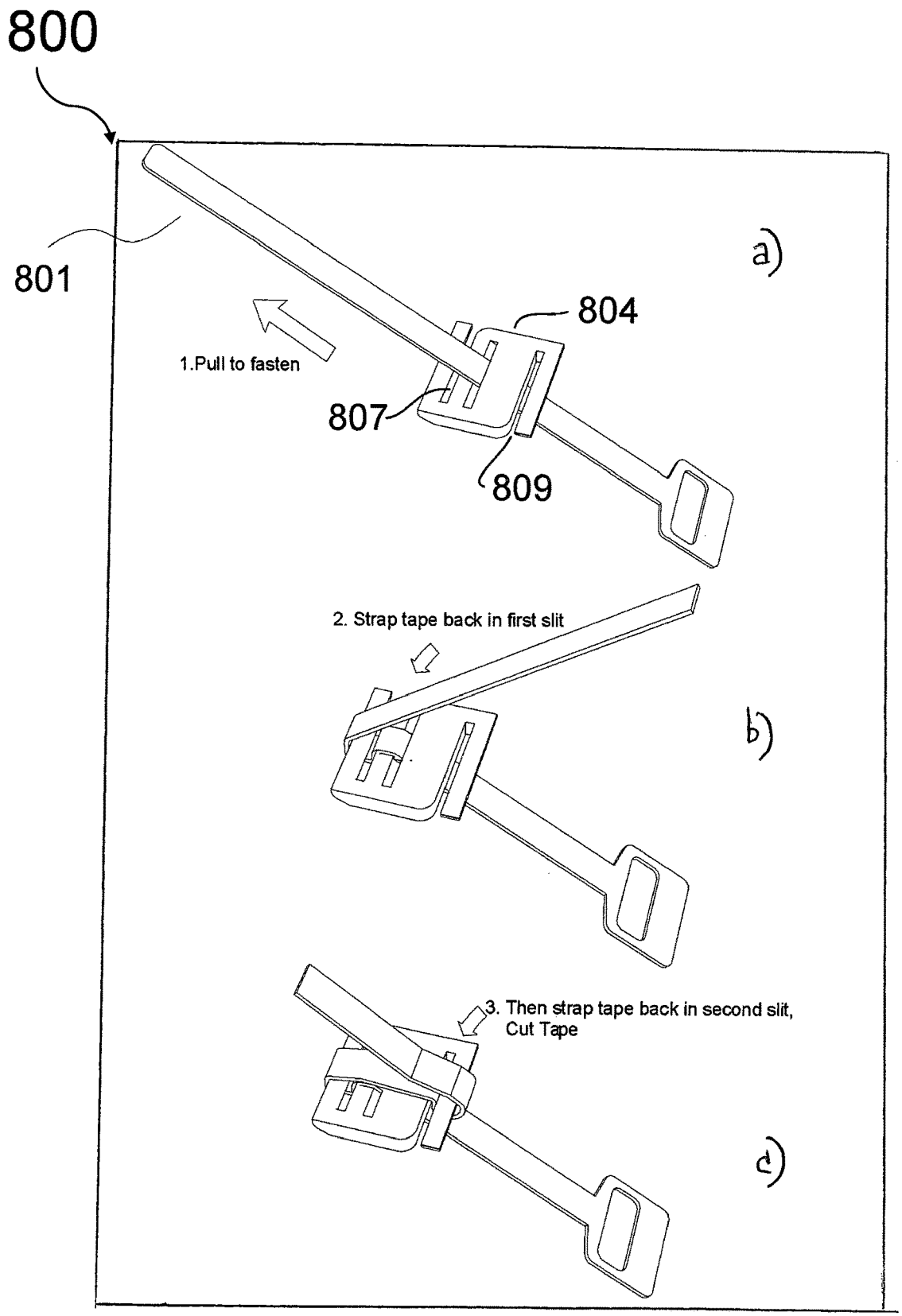
FIG. 14D shows progressive views depicting the process for fastening the element for tendon attachment to the fixation device.

Referring now to FIG. 14D, a series of images depict the process of fastening tendon attachment 801 to fixing device 804. In a first step, the tape is pulled to straighten the graft. By pushing down the extra-osseous element (fixing device 804) to the bone adjacent to the tibial tunnel, tape and the extra-osseous element become wedged (due to the inclination of the slit). This leads to a first fastening of the tape, which can be further enhanced by pulling on the tape. In order to secure the tape further, the tape is strapped through first adjacent slit 807 and then through second slit 809, Step 2. With this procedure, the tape can be easily adjusted and secured without the use of a knot. Application of knots on cords or tapes (or similar structures) under tension is difficult and in general leads to a loosening of the tension, which is avoided with this procedure.

In general, the flat prepared tendon structure can also secured on the tibial side to device (s) exemplified in FIG. 13C (embodiments c-h) or FIG. 13D, where cords protrude from the various graft fixation means. In this case, fixation can be achieved by extra-osseous elements 510', 520', 530', 540' and/or 550', which fixes the cords coming from the graft and have been described in more detail in the section describing the tibial fixation of a multi bundle graft. In a preferred embodiment, the tibial side of a graft prepared from a split tendon is secured by device shown in FIG. 13D, embodiment c) and fixed to the tibia by employing device 550'.

Accessories

In the following description, accessories aiding in the correct placement of the femoral tunnel and a device intended to allow standard tensioning of the graft during reconstruction surgery are presented.

1) Femoral Aiming Aid

Figures 15A, 15B, 15C, 15D:
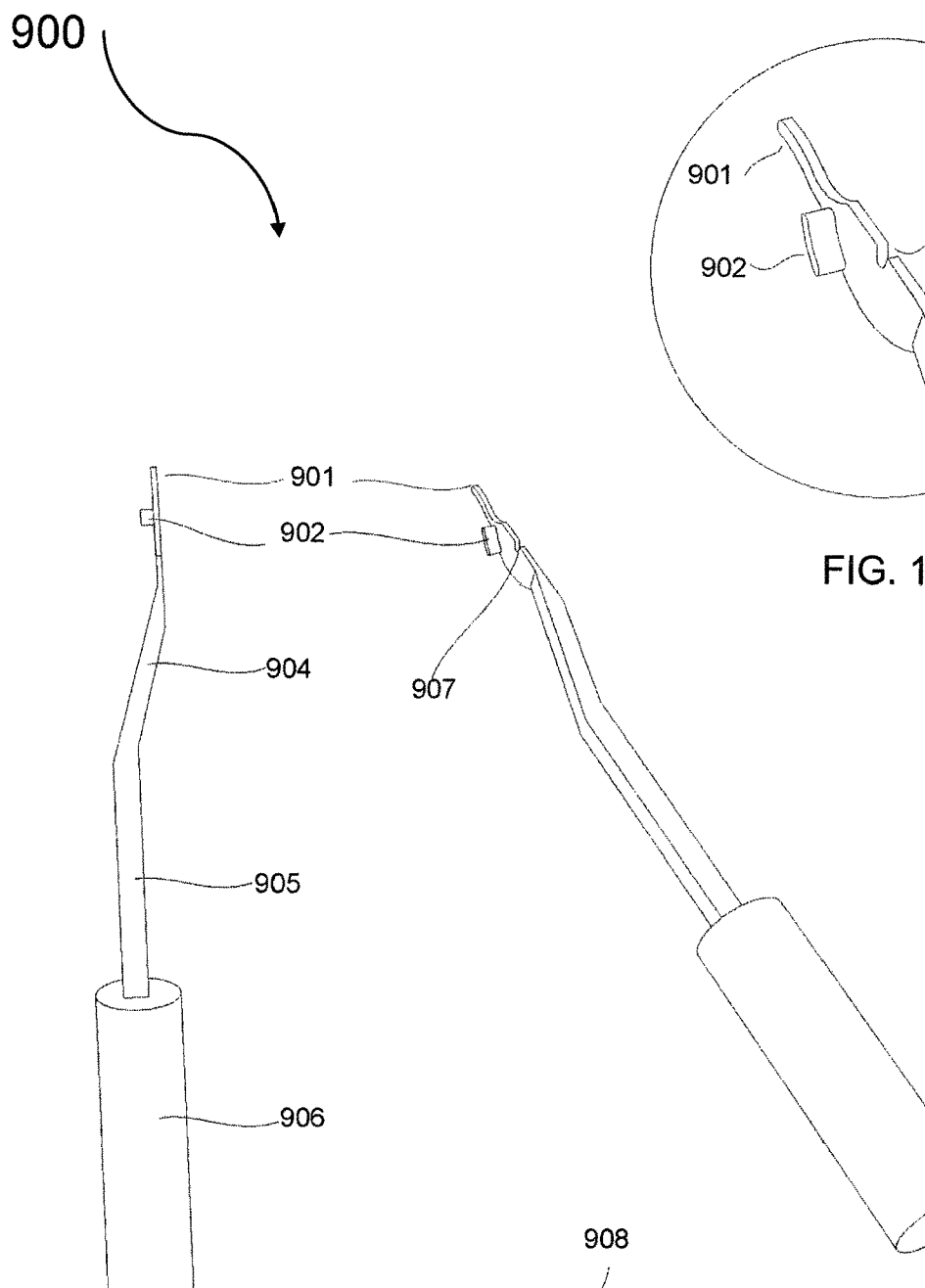
FIG. 15A is a top view of the femoral aiming aid.
FIG. 15B is a perspective view of the femoral aiming aid.
FIG. 15C is a perspective view of the tip of the femoral aiming aid.
FIG. 15D is a perspective view of the femoral aiming aid aligned with a longitudinal cut of the femur.

Referring now to FIG. 15A-15D, femoral aiming aid device 900 helps in setting the femoral guide-wire. FIG. 15A is a top view, while FIG. 15B is a perspective view. The device 900 is positioned at the lateral intercondylar notch wall at the femoral insertion site of the ACL with the help of two "noses" 901, 902 at its end. The device consists of a handle 906 with a curved connecting piece 904, 905 and a tip portion detailed in FIG. 15C. The curvature of connecting piece 904, 905 allows an easier introduction through an anterolateral arthroscopy portal. At its tip device 900 has opening 907 for setting a guide wire. Additionally, two noses 901, 902 aid in placing the device at the right position of the femur, as depicted in FIG. 15D, where a longitudinal cut through the femur 908 with device 900 in place is shown. One "nose" 902 is aligned with the posterior aspect of the femoral condyle (see arrow 910, FIG. 15D) and the second one 901 with the posterior lateral cortex of the femur (see arrow 911, FIG. 15D). These two "noses" are designed to position the drill guide at the femoral insertion site. There is one drill guide for the right and left knee. There are also different sizes of drill guides to take into account the different sizes of the individual insertion sites.

2) Graft Tensioning Device

Figure 16A:
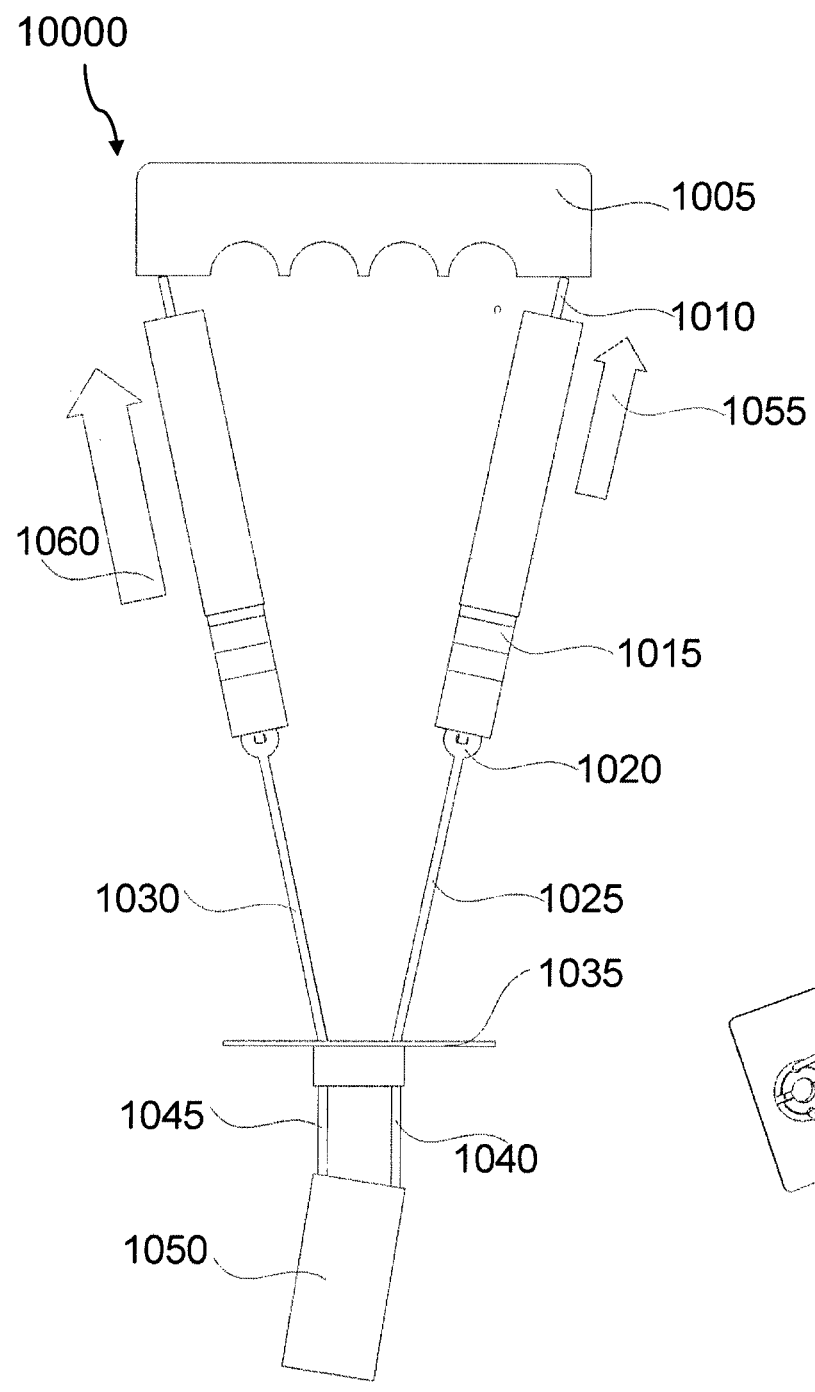
FIG. 16A is a top view of a device for calibrated tensioning of a graft attached to two cords (device not drawn to scale).
Figure 16B:
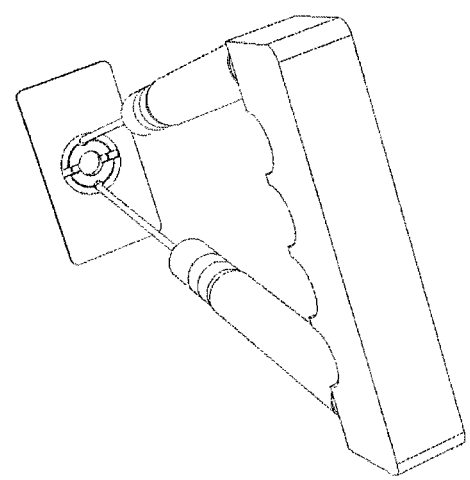
FIG. 16B is a perspective view (surgeon's view) of a device for calibrated tensioning of a graft attached to two cords.

Referring now to FIGS. 16A-16B, device 10000 allows calibrated tensioning of a graft attached to two cords. Currently, the tension applied to grafts used for ACL reconstruction is not standardized and hence subject to high surgeon-specific variation. Furthermore, studies (Biomechanics and anterior cruciate ligament reconstruction, Woo S L et al., *J Orthop Surg Res*, 2006 Sep. 25; 1:2., the content of which is incorporated herein by reference) have shown, that the tension within the ACL varies in the various fiber bundles. A standardized procedure, where the graft can be tensioned taking into account the necessary tension and the distribution of the tension within the graft overcomes these problems.

FIG. 16A shows a front view of device 10000 with attached graft 1050 and graft fixation device 1035. FIG. 16A refers exemplarily to the graft fixation device of FIGS. 10A and 11. Graft tensioning device 10000 is, however, applicable to any graft fixation device in which two cords are employed. As depicted, cords 1040, 1045, coming from the two edges of graft 1050, are fed through graft fixation device 1035 and attached to suspension 1020 on force sensing device 1015 measuring the force applied to the cords and transmitted to the graft. Here force sensing device 1015 is depicted as a spring balance, but every appliance serving the same function can be used. A force sensing device 1015 is attached to each one of the two cords coming from the graft. Different tensions can be applied to each cord by tilting handle 1005 to which the force sensing devices are attached. When a stronger force is applied to the cord on the left (shown as longer arrow 1060) and a weaker force (shown as shorter arrow 1055) on that on the right by tilting the handle, the left and right part of graft 1050 are subject to a differential force. It should be noted that the use of a handle facilitates one-handed operation of the device. By securing the individual cords by the mechanism described in FIGS. 10A to 10E and 11, the tension applied to the graft is locked. Naturally, devices adapted to the use of a different number of cords or tapes and corresponding force sensing devices are variations of device 10000.

Referring now to FIG. 16B, a perspective view (surgeon's view) of the device 10000 is shown. As described above, the differential and calibrated tensioning of the graft can be applied in a one-handed manner, leaving the other hand free for the actuation of the locking mechanism of the graft fixation device.

3) Tibial Dilator

Referring now to FIGS. 22A-22D, a perspective view of the tibial dilator 1200 is shown. The dilators 1200, which are of same size and shape as the intended c-shaped tunnel, can be used to compress or dislocate remaining bone structures to achieve the intended graft channels. Therefore, the head 1201 is introduced in the tibial bores with the help of k-wires 1206. The k-wires 1206 are introduced via holes 1213 (FIG. 22C) in the head and in handle 1203 of the dilator. The k-wires can move freely in head and grooves 1207 on the backside of handle 1203 (FIG. 22B) In a first position, the k wires protrude approximately 3-6 cm over the head of the dilator and the k-wires guide the head through the tibial bores upon introduction of the device until k-wires reach the end of the tibial bores. Upon tapping on the back of the dilator 1208, the dilator moves along k-wires 1206, which hinder a tilting of the head of the dilator and guide the head through the bores. This is facilitated by slopings 1209 and 1210, which allow a gradual compression of the bores until the desired profile 1211 (tibial channel) at its full extent is reached (FIG. 22D).

Consecutively, the dilator is removed from the tibial channel by pulling and tapping on protrusions 1204. This procedure is facilitated by slopings 1212 and 1214, which hinder that the head of the dilator gets stuck upon removal.

4) Femoral Dilator

Figure 23A:
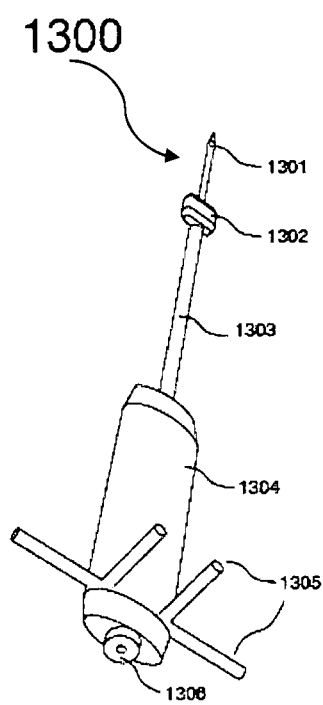
FIG. 23A is a perspective view of the femoral dilator.
Figure 23B:
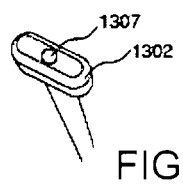
FIG. 23B is a detail of the "head" of the femoral dilator.
Figure 23C:
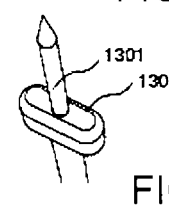
FIG. 23C is a detail of the "head" of the femoral dilator with inserted k-wire.
Figure 23D:
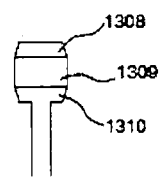
FIG. 23D is a top view of the "head" of the femoral dilator.

Referring now to FIGS. 23A-23D, a perspective view of the femoral dilator 1300 (with inserted k-wire) is shown. The dilators 1300, which are of same size, dimension and shape like the intended slit like tunnel, can be used to compress or dislocate remaining bone structures to achieve the intended graft channels. Therefore, the head 1302 is introduced in the femoral bores with the help of a guiding k-wire 1301. The k-wire is set in an earlier procedure during establishment of the femoral bores and is still in place before the dilation procedure starts. The back of the k-wire, which is placed in the central bore of the femoral bores, is introduced in opening 1307 of head 1302 and the dilator is moved along the axis of the k-wire to the femoral bores. Upon tapping on the back 1306 of handle 1304, the dilator moves along k-wire 1301, which guides the head through the bores. This is facilitated by sloping 1308, which allows a gradual compression of the bores until the desired profile 1309 (femoral channel) at its full extend is reached (FIG. 23D).

Consecutively, the dilator is removed from the tibial channel by pulling and tapping on protrusions 1305. This procedure is facilitated by sloping 1310, which hinders that the head of the dilator gets stuck upon removal.

Methods

In the following description, methods for the anatomically correct reconstruction of ligaments employing flat, ribbon-like grafts will be described. Exemplary, ligament structures within the knee, with special focus on the anterior cruciate ligament are addressed. The methods make use of the devices for ligament preparation, introduction and fixation discussed above. It is appreciated that in one variant of the invention, portions of the graft are positioned to completely span or substantially span the distance "slit like" femoral bone apertures in the femur in the knee joint, while other portions of the graft span the "C-shaped" or half-moon shaped apertures in the tibia in the knee joint.

Creation of ACL Insertion Sites

1) Creating the Tibial Insertion Site of the ACL

Figures 17A, 17B:
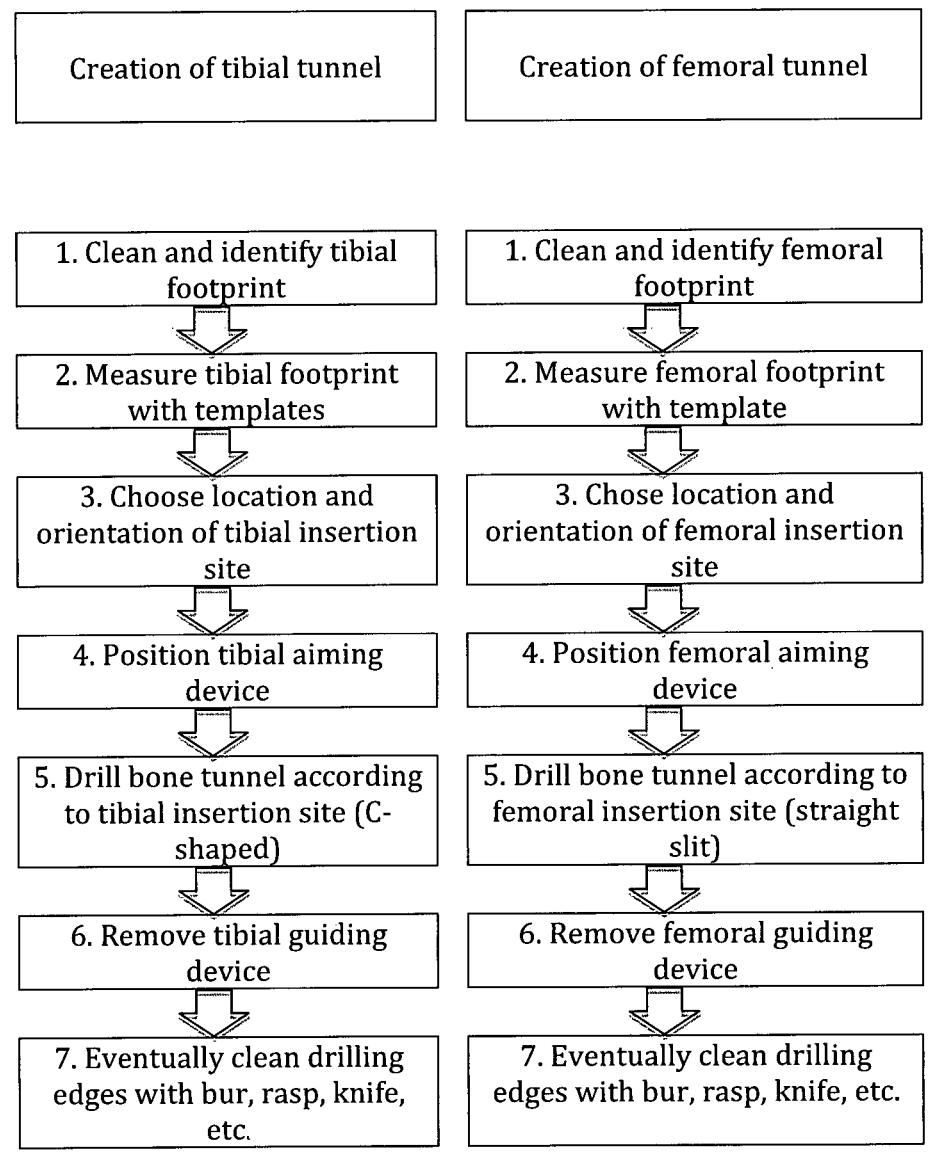
FIGS. 17A and B are flowcharts depicting a generic method for anatomically correct reconstruction of a ligament structure employing C-shaped and slit-like bore tunnels.

Referring now to FIG. 17A, flowchart 1100 describes a generic method for creating the tibial insertion site of the ACL in seven steps. In order to measure and analyse the length and shape of the insertion site, the torn ligament is first removed and the insertion site is cleaned from residual ligament. As shown in FIG. 1B, the insertion site is a C-shaped or half-moon like structure, with patient specific variations in size and curvature. The method addresses the naturally occurring and anatomically correct reconstruction of this structure. Upon having identified location, size and orientation of the insertion site, an aiming device is installed. Creation of the C-shaped or bent tunnel can be accomplished by a bur, chisel or preferably, by multiple drilling techniques.

By way of example, flowchart 1110 in FIG. 17A describes a method for achieving this structure. With the help of device 200 multiple drill holes are arranged in a manner reflecting the ribbon-like and C-shaped nature of the ligament insertion site. Since these bores overlap, a curved to slit is created. By using appropriate drill sleeves 207 the tibial tunnel and respectively insertion site can be adjusted to patient specific anatomy.

2) Creating the Femoral Insertion Site of the ACL

Referring now to FIGS. 17A-17B, flowcharts 1100 and 1100' describe generic methods for creating the tibial and femoral insertion sites respectively in seven steps. In order to measure and analyse the length and shape of the insertion site, the torn ligament is removed and the insertion site is cleaned from residual ligament.

As shown in FIG. 1C, the insertion site is a straight, ribbon-like structure, with patient specific variations in length and width. The method addresses the anatomically correct reconstruction of this structure. Drilling of the slit-like tunnel can be accomplished by using a bur, chisel or preferably, by creating said structure by multiple drilling with drills representing the width of the insertion site or the torn ligament, respectively. Exemplary, flowchart 1110' in FIG. 17B and flowchart 1120' in FIG. 18B describes a method for achieving this structure. With the help of device 300 multiple drill holes are arranged in a manner that reflects the straight and ribbon-like nature of the ligament insertion site. Since these bores overlap, a slit is created. By using appropriate femoral aiming aid 300 the femoral tunnel and respective insertion site can be adjusted to patient specific anatomy. FIGS. 18A-18B illustrate the creation of tibial tunnel and femoral tunnels in 10 steps in one variant of the invention.

Graft Selection, Preparation and Fixation

Referring now to FIGS. 19A-19B, flowcharts 10120, 10120' depict generic methods using components of system 3000 for creating a ribbon-like ACL graft from either multiple parallel bundles or from split tendons. In order to resemble the natural anatomy of the ligament as closely as possible, multiple ways are possible to create a ribbon-like structure preferably from a tendon graft.

By way of example, but not exclusively, possible graft donor sites for the reconstruction of the ACL, and the way in which autografts and allografts can be prepared, are as follows:

1. Hamstrings

Figure 21A:
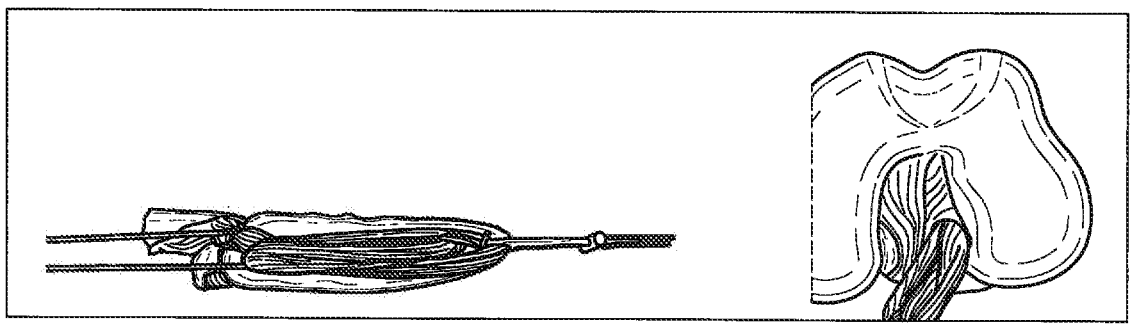
FIG. 21A is a photograph depicting a ribbon-like graft made from a multiple tendon bundle.
Figure 21B:
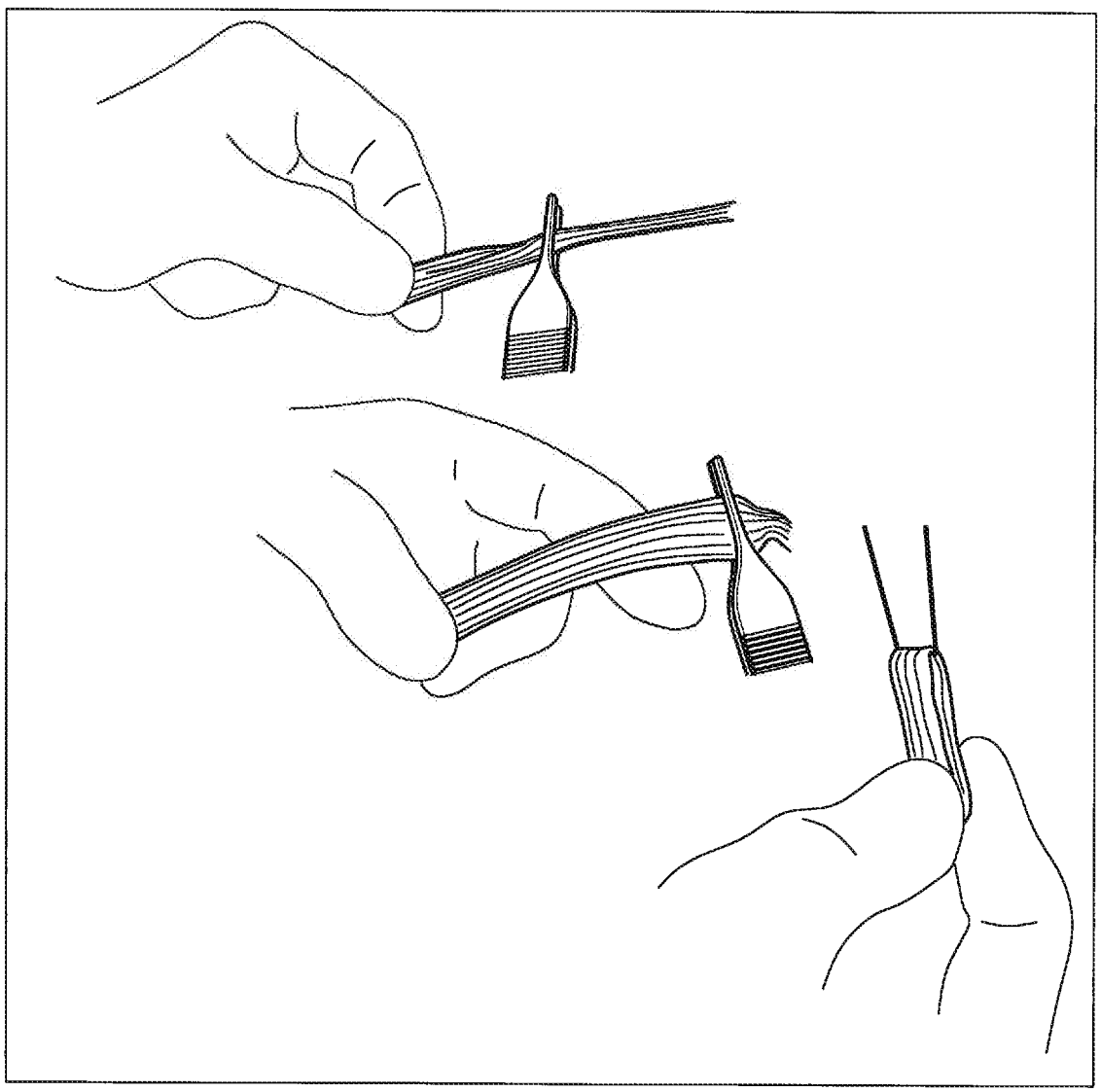
FIG. 21B is a photograph depicting a ribbon-like graft made from a split tendon.

To create a flat rectangular shape with hamstring tendons two options are possible. (1) A graft made from four strained hamstrings, which, in contrast to common round techniques, is folded in a way in which the tendon strands lay parallel to each other. (FIG. 21A). (2) The second possibility is to partially split the round hamstring tendon longitudinally to create a flat tendon (FIG. 21B). This novel way of hamstring use allows the creation of tendon shapes, which closely resemble the "ribbon-shape" ACL.

2. Patellar Tendon

Alternatively to aligning multiple tendon strands or splitting the tendons, the graft can be carved out of the patellar tendon in a flat and ribbon shaped fashion. Commonly it is harvested with two bone blocks, which are prepared to fit a round bone tunnel. The proposed technique employs a small, rectangular bone block, but also uses without a bone block are possible.

3. Quadriceps Tendon

In the same way, a ribbon shaped part of the quadriceps tendon (QT) can be carved out of the quadriceps tendon with or without a bone block from the patella. Commonly, the QT has been prepared in a round shape with a diameter up to 10 mm. With the proposed technique a 6-8 cm long strip (depending on the use of a bone block) of the central third of the QT is utilized. The strip which is carved out of the quadriceps tendon is 10 to 15 mm wide and 4 to 5 mm thick depending on the size of the ACL to be replaced.

If no bone block is used, a 5-12 mm long portion of the insertion zone of the quadriceps tendon to the patella can be lifted from the patella and harvested together with the quadriceps tendon-graft. This (thinner) portion of the graft can be flipped back over the femoral graft fixation means to provide a round and smooth edge for pulling in of the graft. With this proceeding a splicing of the graft at the tunnel openings can be minimized during pulling in of the graft.

4. Synthetic Ligaments

In the same way, the proposed reconstruction method can be performed employing synthetic ligaments with a flat ribbon-like appearance.

Graft Preparation Using Multiple Parallel Bundles.

Figure 20A:
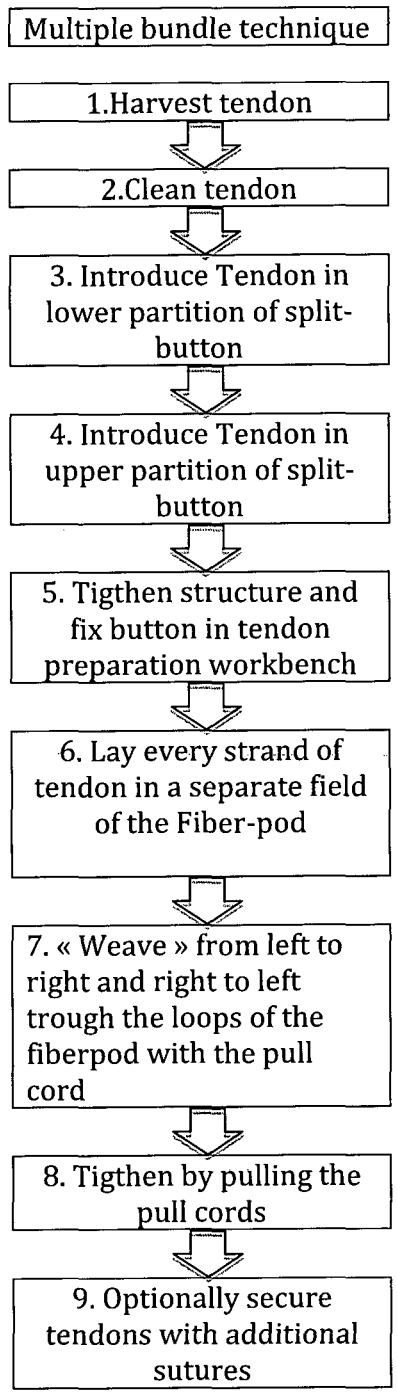
FIGS. 20A and B are flowcharts depicting the methods for creating a ribbon-like ACL graft from either multiple parallel bundles or from a tendon, which is split to form a ribbon-like structure.
Figure 20B:
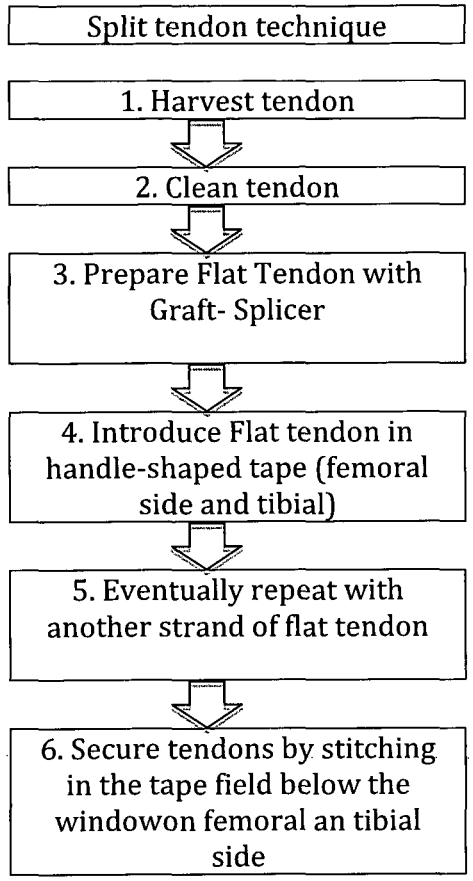
FIG. 20C is a flowchart depicting the method for inserting, tensioning and fixing a ribbon-like graft for anatomical ACL reconstruction

Referring now to FIGS. 20A-20B, flowcharts 1130, 1130' describes a method of preparing ribbon-like grafts from tendon bundles. Currently, tendon grafts are harvested and multiple bundles of the tendon are sewed together in different ways, employing multiple suture techniques. All of these suture techniques have in common, that a more or less cylindrical structure with a round cross section is created, since these grafts are intended to fill the cylindrical bores created with the conventional reconstruction techniques.

By contrast, the method presented here allows reconstruction of the torn ligament with a ribbon-like structure, which is anchored in slit-like bore tunnels. The ribbon-like grafts from tendon-bundles are made by means of devices 400 and 500.

Graft Preparation Using the Split-Tendon Technique

Referring now to FIG. 20B, flowchart 1130' describes a method of preparing ribbon-like grafts by using the split-tendon technique. In contrast to the ligament it should replace, the harvested tendon, which is currently used for reconstruction has cylindrical shape with a round cross section. In order to create a flat, ribbon-like structure, the tendon is split by an incision reaching the cylinder axis, and subsequently unfolded into two connected halves. This incision can be accomplished by using a knife, sharp spoon or anything the like. In a preferred embodiment device 600 is used to incise the tendon. It allows longitudinal cutting of the tendon, with minimal damage to the parallel tendon fibres, which could negatively influence the stability of the graft. The flat tendons are secured by stitching to femoral and tibial fixation means, which allow the upholding of the ribbon shaped nature of the graft.

In a variation, the flat and ribbon shaped graft is carved out of a tendon (e.g. patella tendon, quadriceps tendon) as a rectangular strip and secured by stitching to femoral and tibial fixation means, which allow the upholding of the ribbon shaped nature of the graft.

Insertion and Fixation of Ribbon-Like Grafts

Figure 20C:
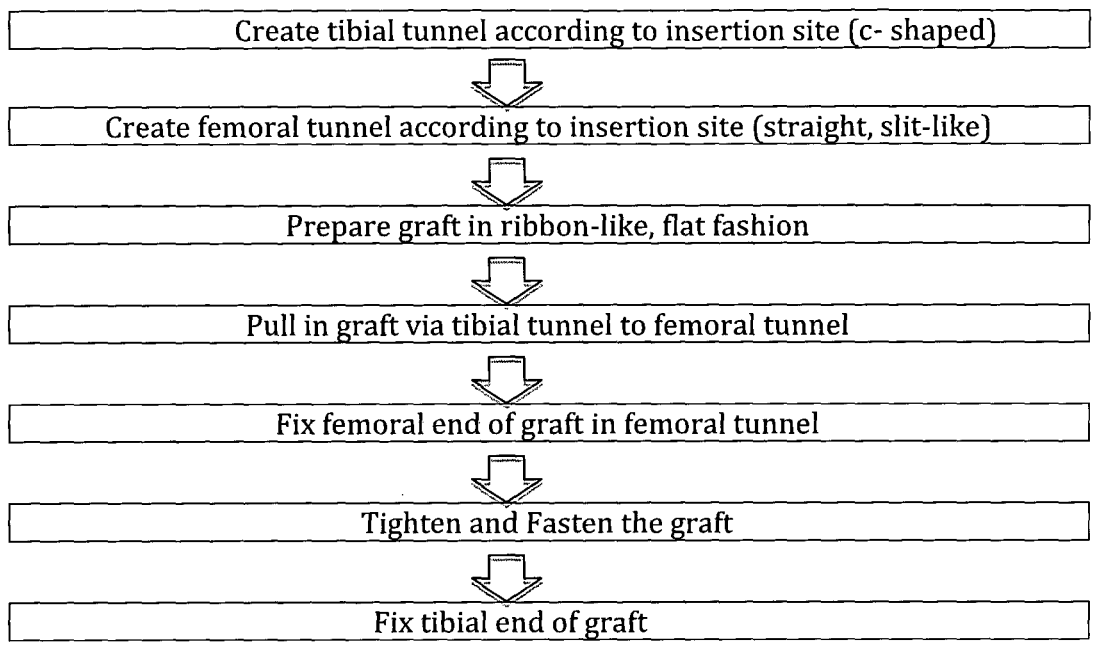

Referring now to FIG. 20C, flowchart 1140 describes a method for inserting and fixing a ribbon-like graft in the tibial and femoral tunnel or pocket. In further variants of the invention, a system for the anatomical reconstruction of the anterior cruciate ligament to mimic a naturally occurring ACL in biomechanical function and stability includes devices selected from a list of devices that include one or more of: aiming device 200 for the creation of the tibial bone tunnel; aiming device 300 for the creation of the femoral bone tunnel or pocket; guiding device 900 for positioning a guide wire at the femoral insertion site; a device for the attachment of ribbon-like grafts to the femoral insertion site; a device for the attachment of ribbon-like grafts to the tibial insertion site; an optional device 1000 for tensioning the graft; and, devices 500, 600 for preparing flat, ribbon-like grafts.

Aiming device 200 for the creation of the tibial bone tunnel with a bent or C-shaped appearance includes at least one or more portions thereof selected from: an intra-articular portion 203 configured to position and hold a template 206 at an intra-articular insertion site; and, an extra-articular portion 202, holding an extra-articular drill sleeve 207, wherein intra- and extra-articular portions are rigidly connected. Aiming device 300 for the creation of a femoral bone tunnel or pocket with straight, slit-like appearance, includes at least one of the following portions and features thereof: a guiding tube 303 for the aiming of a guide wire; drill channel(s) 304 adjacent to said guiding tube; and, viewport for an arthroscope 307 configured to allow simultaneous observation of a guide wire and insertion site.

The device for the attachment of ribbon-like grafts to the femoral insertion site includes a device which includes: device 400 for the attachment of ribbon-like grafts from multiple tendon bundles; and/or device 700 for the attachment of ribbon-like grafts from split tendons. The device for the attachment of ribbon-like grafts to the tibial insertion site includes a device selected from a list of devices, and/or one or more features of the devices described below: a device for the attachment of grafts made from multiple tendon bundles, chosen from a list including: device 510' comprising a rigid flat body with holes 551, 552 for cord insertion and knotting; device 520' comprising a rigid flat body with a depression 563 accepting the knot; device 530' comprising a rigid flat body with holes adapted for fastening the inserted cords by wedging before tying a knot device 540' comprising a rigid flat body 580 with a sloped extension 585 with slits 586 permitting knotting and tensioning single cords; and, device 800 for the attachment of ribbon-like grafts made from split tendons. Device 500 is adapted for the preparation of flat, ribbon-like grafts from multiple tendon bundles in one variant. In another variant, device 600 is adapted for the preparation of flat, ribbon-like grafts from split tendons.

Device for the creation of a first bone tunnel has an adaptor for an intra-articular template, whose inner opening represents the bore, which will be formed by drilling when the corresponding extra-articular drill-sleeve will be employed. The adaptor of the intra-articular template features a spike (or similar appliance) for fixing the intra-articular portion of the device to a surface within the joint (e.g. the tibial plateau).

The intra-articular template represents the shape and length of the patient specific insertion site of the ligament. (e.g. bent, arched or c-shaped for the tibial insertion site of the anterior cruciate ligament). The extra-articular drill sleeve corresponds to the intra-articular template in one variant of the invention. The extra-articular drill sleeve features at least one drill sleeve for the guidance of a driller/bur and at least one guidance tube for a guide-wire. Drill tunnels for guidance of the drills can not only be formed as cylindrical holes, but also segments of cylindrical holes big enough to guide a drill/bur. The bore(s) created by using the guidance tube for the driller(s)/bur(s) overlap(s) with the bore created after over drilling of the guide wire. Alternatively, guidance tubes for the drill/bur can be of an elongated and bent cross-section, along which a bur or drill can be moved to form a slit-like opening in the bone.

The extra-articular portion of the aiming device features a holder for the drill-sleeve, which can be moved along the drill-axis and be locked with a screw or similar device. The holder of the drill sleeve can fix the drill-sleeve by slight compression of the drill sleeve or a similar action. The extra-articular drill sleeve may feature at least one tube (preferably slotted), through which a spike/guide-wire can be moved along the drill axis, which is used to stabilize the extra-articular portion of the device to bone. The spike(s)/guide-wire(s) (which is/are intended to stabilize the extra-articular portion of the device to bone) in the drill sleeve can be fixed by slight compression of the drill sleeve or a similar action. The spike(s)/guide-wire (s) (which is/are intended to stabilize the extra-articular portion of the device to bone) is/are part of the extra-articular drill sleeve holder.

The device for the creation of a second bone tunnel has at least one drill sleeve for the guidance of a driller/bur and at least one guidance tube for a guide-wire. The bores created with the device represent the shape and length of the patient specific insertion site of the ligament. (e.g. straight and ribbon like at the femoral insertion site of the anterior cruciate ligament). Drill tunnels for guidance of the drills can be formed not only as cylindrical holes, but also segments of cylindrical holes big enough to guide a drill/bur. The depth of the bores can be controlled by reading the depth marks of the driller at the edge of the bore sleeve before and during drilling. The device can be used to perform drilling through the whole bone to form a uniform tunnel OR can be used to create a pocket in the bone. The device can be used to create a pocket in the bone with a (central) tunnel, which reaches the other cortex of the bone, thereby minimizing the damage to the bone. The bore(s) created by using the guidance tube for the driller(s)/bur(s) overlap(s) with the bore created after over drilling of the guide wire. Alternatively, guidance tubes for the drill/bur can be of elongated cross-section, along which a bur or drill can be moved to form a slit-like opening in the bone.

The device features a view-port for an arthroscope, which allows direct visualization of the tip of the guide-wire and the graft insertion site.

The guide-wire is equipped with a removable stamping adaptor, which can be used to transiently fix the guide-wire by tapping or pushing on the stamping adaptor in the longitudinal direction of the guide-wire. The guiding device for the right allocation of the femoral bone tunnel features a bent handle to ease the access to the femoral insertion site in an arthroscopic setting. Furthermore, it features two "noses" for alignment of the device with the posterior aspect of the femoral condyle and with the posterior lateral cortex of the femur.

A system for the ribbon-like attachment of multiple tendon bundles includes one or more of the following devices and/or features thereof: a button like device for the mounting and fixation of multiple bundle tendon grafts; a device for the alignment of individual bundles using a "weaving-technique"; and, a device for fixing a ribbon-like tendon graft with at least two cords.

The button-like device has an elongated body 607, which holds a sling or loop, which is subdivided by at least one partitioning 605. The partitioning can be either fixed 605 or can move along the sling or loop, as exemplified in FIG. 12C. The strands of the tendons form a linear alignment, where the upper strand is held apart by the lower strand of the tendon. Alternately, the strands of the tendons form a linear, semi-rigid structure of the individual tendon bundles, which still can be bent transversally. The strands of the tendons form a linear, semi rigid structure of the individual tendon bundles, which still can be passed through a non-linear (e.g. C-shaped) bone tunnel.

The pushing together of the individual tendon bundles is hindered by a sequential pulling in, which favours a smooth pulling in of the graft, especially in slit-like bone tunnels with a small width. The device for the alignment of individual bundles using a "weaving-technique" features a baseplate with holes 505, which are connected with slits 506. The pulling ends of a cord (or the like, 501 and 502) as well as the loops 503 are on the front side of the base plate, while the connecting sections of the cord are on the backside of the base plate. The size of the holes is large enough to allow passing of a cord or suture-material 501,502, while the slits are more narrow and allow the passing of the cord only when force is applied to the cord and the walls of the slits are dilated.

A linear mounting for the opposing side of a multi-bundle graft is formed, where the individual strands are pressed together, but cannot slip over each other, thereby eliminating the formation of a bulky graft. This is especially important in the case where slit-like tunnels with a small width are employed. The cord slips through the slits of the base plate if enough force is applied, and the linear tendon/cord construct is released from the base plate.

The device for fixing a graft with two cords has a flat rigid body, which is larger than the created bone tunnels and has two openings to accept the two cords, which are attached to the graft. The flat rigid body has a deepening or grooves with two openings, which accepts the knot after knotting of the two cords, which are attached to the graft. The openings are narrower to the center of the device to allow a wedging together of the cords before knotting. The cords can be tensioned after knotting by pulling them over a slope to a securing position more distant from the graft. The cords can be tensioned optionally. Alternatively, the cords can be tensioned and fixed by graft fixation means exemplified in FIG. 10A. The device for fixing a graft with two cords has a flat rigid body with sleeve and rotation of an inner fastening member results in displacing cut outs from the openings in the sleeve, whereby the cords are compressed between the jagged inner fastening member and wall of the sleeve.

A system for the ribbon-like attachment of a flat split-tendon includes one or more of the following devices and features thereof: a button-like device for the mounting and fixation of a flat split-tendon graft; a buckle-like device for the mounting and fixation of a flat split-tendon graft; and/or a device for preparing a flat tendon graft out of a cylindrical tendon graft.

The button-like device has an elongated body (607), which holds a tape sling or loop, which has an opening with an adjacent stitching area. The stitching area is used for the fixation of the flat tendon in a planar way by securing the edges and the mid of the tendon over the distance of the opening. A semi-rigid structure is formed, where the tendon graft cannot slip together, but a transversal bending is still possible as shown in FIG. 13B.

The buckle like device for the mounting and fixation of a flat split-tendon graft features a tape-like structure (801) with an opening and stitching area. The tape-like structure is fastened and fixed with an extra-osseous element at the exit of the bone tunnel by passing the tape through a slit in the buckle-like device. The buckle-like device features at least one adjacent slit, which can be open on one side (807 and 809) or closed. The buckle-like device features preferably two adjacent slits (807 and 809) which are open on one side or on opposite sides. The buckle-like device features an angulated slit, preferably in an angulation that the tape and the extra-osseous element become wedged together, when tension is applied to the tape and the extra-osseous element is locked at the exit of the bone tunnel.

The tension of the tape (and consequently the graft) can be further adjusted by pulling of the tape and a first fastening of the tape is accomplished by the mechanism described herein. The tape can be further secured by strapping back in a first adjacent slit (807) and then to a second slit. The application of knots for the fixation of graft structures under tension is avoided and therefore a loosening of the tension of the cord/tape is omitted with this proceeding. The tape without the buckle-like device can be secured by introduction of a screw, which presses the tape towards the bone-tunnel wall.

In general, the flat prepared tendon structure can also be secured on the tibial side to device (s) exemplified in FIG. 13C (embodiments c-h) or FIG. 13D, where cords protrude from the various graft fixation means. In this case, fixation can be achieved by an extra-osseous element 510', 520', 530', 540' and/or 550', which fixes the cords coming from the graft and have been described in more detail in the section describing the tibial fixation of a multi bundle graft. In a preferred embodiment, the tibial side of a graft prepared from a split tendon is secured by device shown in FIG. 13D (embodiment c) and fixed to the tibia by employing device 550'.

A flat tendon graft is prepared from a cylindrical graft by longitudinal splitting. A cylindrical graft is placed in a device, such as that shown in FIGS. 12A-12C, which cuts the cylindrical graft to its approximated middle portion, thereby allowing an unfolding of the cylindrical graft to a flat structure. The device may include precautionary measures or measurement points, which avoid total cutting or splitting of the graft, such as a set maximum penetration into the cutting canal 602.

The device features standardized adaptors for conventional surgical blades. A cylindrical graft is placed in a device, which fixes the graft on its distant side and has a slide with an attached cutting device, which moves longitudinal to the inserted graft, thereby cutting the graft in its longitudinal direction. The cylindrical graft is placed in a device with a fixed cutting device and the graft is pulled through the device and is cut in its longitudinal direction.

A method for creation of bone tunnels representing the insertion site of a ligament structure (e.g. the anterior cruciate ligament) includes the following steps: performing the measurement of the insertion sites (e.g. tibial and femoral); choosing the location and orientation of the insertion sites (e.g. tibial and femoral); positioning of an aiming device(s) over the chosen location(s); creating tunnels OR incomplete drilling/burring of said bores to create a pocket-like structure in the bone, which resembles the insertion site or naturally occurring footprint of the ligament attachment point. (Half-moon or C-shaped at the tibial insertion site and straight and ribbon shaped at the femoral attachment site); removing the aiming device(s); and, optionally cleaning of the edges by using a drill, bur, rasp, chisel, knife or similar device.

A method of multi-bundle tendon preparation, which results in a ribbon-like structure to reconstruct a ligament is also included in the invention. The method including the steps of: harvesting the tendon to be used for the tendon preparation; preparing the graft, which allows the mounting and fixation of the tendon in a way that the individual strands are arranged in a ribbon-like, flat fashion; and, preparing the individual strands of the graft in a linear arrangement on the opposite side of the graft.

The invention includes another variant in which a method of a flat tendon preparation and attachment, which results in a ribbon-like structure to reconstruct a ligament. The method including the steps of: harvesting the tendon to be used for tendon preparation; preparing the round tendon structure into a flat, ribbon-like structure by cutting or blunt incising along the longitudinal axis of the tendon following the tendon fibres; attaching the flat tendon to a structure, which allows a spanning of the flat tendon orthogonally (or near orthogonal) to its longitudinal axis; attaching of the opposite side of the flat tendon to a device, which allows the spanning of the flat tendon orthogonally (or near orthogonal) to its longitudinal axis; and, fixing the flat tendon in both slit-like straight or bent bone tunnels. Alternatively, flat, ribbon-like grafts can be made by carving portions (strips) out of a bigger tendon (e.g. patella tendon, quadriceps tendon).

Graft Fixation Using the Split Tendon Technique

In yet another variant, a method of multi-bundle tendon preparation, which results in a ribbon-like structure to reconstruct a ligament is described in the invention. The method including the steps of: harvesting the tendon to be used for the tendon preparation; preparing the graft, which allows the mounting and fixation of the tendon in a way that the individual strands are arranged in a ribbon like, flat fashion; and, preparing the individual strands of the graft in a linear arrangement on the opposite side of the graft.

In yet another variant, a method of a flat tendon preparation and attachment, which results in a ribbon-like structure to reconstruct a ligament, is described herein. The method includes the steps of: harvesting the tendon to be used for tendon preparation; preparing the round tendon structure into a flat, ribbon-like structure by cutting or blunt incising along the longitudinal axis of the tendon following the tendon fibres; attaching the flat tendon to a structure, which allows a spanning of the flat tendon orthogonally (or near orthogonal) to its longitudinal axis; attaching of the opposite side of the flat tendon to a device, which allows the spanning of the flat tendon orthogonally (or near orthogonal) to its longitudinal axis; and, fixing the flat tendon in both slit-like straight or bent bone tunnels.

Figure 24:
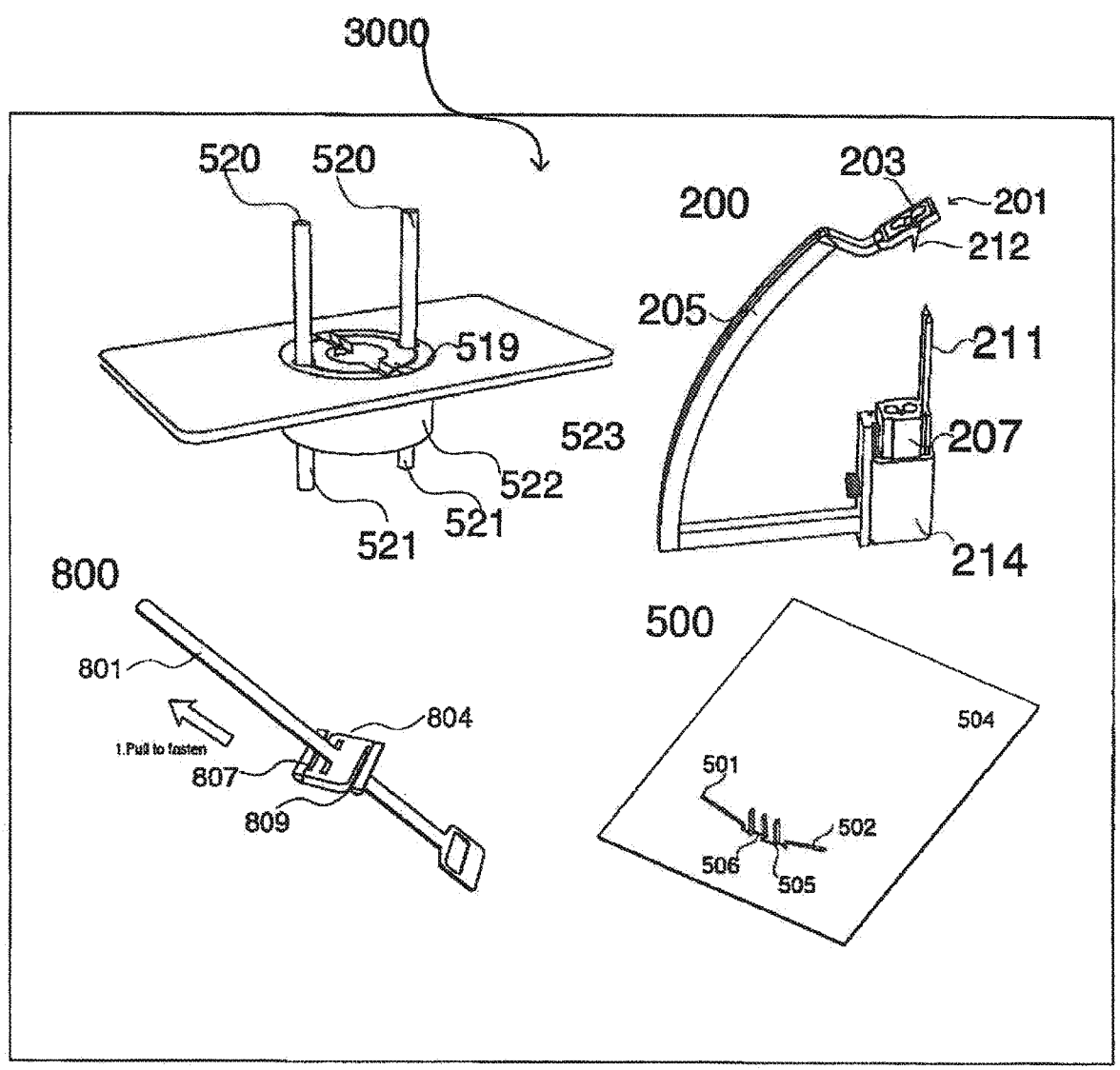
FIG. 24 illustrates an overall system view with exemplary system devices described herein, and in which a plurality of the system devices described herein are used in various combinations.

FIG. 24 illustrates an overall system 3000 architecture view and components of system with exemplary system devices 200, 400, 500, 550 described herein (of course, additional devices described herein are also used in variants of the invention and incorporated into system 3000 where desired), and in which a plurality of the system 3000 devices described herein are used in various combinations. It is appreciated that all of the system 3000 devices described herein are used in various combinations to enable the system and methods described herein. It is appreciated that one or a plurality of the devices are used in system 3000 to achieve the stated purposes of reconstructing a portion of a knee joint with a torn anterior cruciate ligament using a graft, wherein the graft having a first end and a second end, and whereby naturally occurring attachment footprints of a native ACL are mimicked to provide biomechanical stability to the knee joint.

As illustrated in FIGS. 2A-20C, 22A-23D, the invention provides a system and methods for preparing a first and second bone for a graft procedure. The system includes a device for creating on the first bone an entrance point mimicking a first native ligament attachment footprint (1002 FIG. 1B), the first native ligament insertion site 1000 optionally being a substantially half-moon shaped footprint 1002, the device (200, 200', FIGS. 2A and 4C) having an appliance for sequential drilling or burring of overlapping bores, which are Ran arranged in a c-shaped manner to create said c-shaped insertion site; and a device (300, FIGS. 5A-6C) for creating on the second bone an entrance point mimicking a second native ligament attachment footprint 1102, the second native ligament attachment footprint 1102 optionally being a substantially slit shaped footprint, the device (300) having an appliance for sequential drilling or burring of overlapping bores, the bores being arranged in a slit-shaped manner to create a slit-shaped insertion site, the slit-shaped insertion site substantially conforming in size to a corresponding aperture created with the first device.

As shown in FIGS. 20A-20B, the system and method further includes a third device for creating a substantially ribbon-like ACL graft, said graft having a first end and a second end, the device selected from a group consisting of a device for creating a substantially ribbon-like ACL graft, said graft having a first end and a second end, a device having an appliance allowing to maintain the ribbon-like appearance of the graft by affixing parallel tendon bundles or affixing tendons which are split and prepared in a way to give a flat, ribbon like appearance, and a device for affixing portions of a tendon which have been prepared to give a substantially flat and ribbon like appearance, and optionally, includes a device for fixing at least a portion of the first end of the graft at a tibial anchor point, the device having a flat structure attached to a mechanism, the mechanism allowing immobilization of the attached graft by wedging and blocking of the attached fixation means.

As shown in FIGS. 9A-9D, the system and method also include devices 510' to 540' for fixing at least a portion of the second end of the graft in a femoral anchor point, the device having a button-like device for the extra-osseous fixation of the graft, the graft being connected to an appliance, the appliance allowing the affixing of a substantially flat graft to a flat structure on the fifth device by attaching the graft to said flat structure, the flat structure being flexible enough to first pass through a c-shaped bone tunnel and second through said slit-shaped bone tunnel.

In another variant and as shown in FIGS. 8A-8I, the invention provides a graft and a method for creating a graft for ACL reconstruction. The graft includes a first portion which is shaped and dimensioned to substantially conform to a slit shaped bone entrance point. A second portion is shaped and dimensioned to be substantially ribbon like, and a third portion which is shaped and dimensioned to substantially conform to a C-shaped bone entrance point. The system is used in a method for creating a graft for ACL reconstruction and the system includes a device for making the graft as described herein.

As shown in FIGS. 24, 17A-18B and the other figures herein, the system 3000 and method is used for reconstructing a portion of a knee joint with a torn anterior cruciate ligament using a graft. The graft has a first end and a second end. It is appreciated that the naturally occurring attachment footprints of a native ACL are mimicked to provide biomechanical stability to the knee joint. The system includes a first immobilizer having a flat structure attached to a button-like device for the extra-osseous fixation of the graft, the first immobilizer for positioning and use at a portion of the first end of the graft in, or optionally on a femur, at least a portion of the graft adapted for passing through a substantially slit shaped aperture on the femur. Also provided is a second immobilizer having a flat structure attached to a mechanism, the mechanism allowing immobilization of the attached graft by wedging and blocking of the attached fixation means.

The second immobilizer is used for positioning and use at a portion of the second end of the graft in, or optionally on a tibia, wherein at least a portion of the graft is adapted to pass through a substantially C-shaped aperture on the tibia.

In another variant, the invention provides a method of reconstructing a knee joint with an anterior cruciate ligament tear using a graft. The graft has a first end and a second end. The method includes the steps of: immobilizing a first end of the graft on a femur, at least a portion of the graft passing through a substantially slit shaped aperture on the femur; immobilizing a second end of the graft on a tibia, at least a portion of the graft passing through a substantially C-shaped aperture on the tibia; and affixing the ends of the graft on their respective insertion sites in a manner mimicking naturally occurring attachment insertion sites of a native ACL, in order to provide biomechanical stability to the knee joint.

In another variant, the invention provides a system 3000 and method (FIGS. 17A-18B) of providing substantially equal biomechanical stability for a bipedal mammal. The bipedal mammal has a native ACL in a first knee joint and a torn ACL in a second knee joint in the clinical setting. The method includes reconstructing the torn ACL in the second knee joint to obtain a reconstructed ACL, the reconstructed ACL including a first portion of a graft passing through a substantially slit-like aperture in a first bone, and a second portion of the graft passing through a substantially C-shaped aperture in a second bone; affixing the ends of the graft on their respective insertion sites in a manner mimicking naturally occurring attachment insertion sites of a native ACL, in order to provide biomechanical stability to the knee joint; and, allowing for healing with physiotherapy and supervised recovery, whereby thereafter, the biomechanical stability of the first knee joint is substantially similar to the biomechanical stability of the second knee joint.

In yet a further variant and as illustrated in FIGS. 24, 17A-17B, the invention includes a system 300 and method of providing substantially equal biomechanical stability for a bipedal mammal having a native ACL in a first knee joint and torn ACL in a second knee joint, whereby after healing, the biomechanical stability of the knee joints are substantially similar, the method comprising the steps of: forming a graft of an anatomically correct reconstructed ACL; forming an ACL footprint mimicking a native ACL footprint in the second knee joint; passing a first portion of the graft that passes through a substantially slit-like aperture in a first bone; passing a second portion of the graft through a substantially C-shaped aperture in a second bone; affixing the ends of the graft on their respective insertion sites in a manner mimicking naturally occurring attachment insertion sites of a native ACL, in order to provide biomechanical stability to the knee joint; and allowing for healing with physiotherapy and supervised recovery, whereby thereafter, the biomechanical stability of the first knee joint is substantially similar to the biomechanical stability of the second knee joint.

In yet another variant and as illustrated in FIGS. 2A-2C, the invention includes a system 300 method of preparing a tibia for an anatomically correct ACL reconstruction using various devices forming a part of system 3000, including devices 200 and 200'. The method includes cleaning and identifying a tibial ACL footprint; measuring the tibial ACL footprint with a template; locating and orienting a tibial insertion site; positioning a tibial aiming device; drilling a bone tunnel, or optionally a pocket, correlated to the tibial insertion site in a substantially C-shaped configuration; removing the tibial aiming device; and, optionally cleaning drilling edges.

In yet further variant and as illustrated in FIGS. 5A-5D, the invention provides a system 3000 and method of preparing a femur bone for an anatomically correct ACL reconstruction. The method includes the steps of: cleaning and identifying a femoral ACL footprint; measuring the femoral ACL footprint with a template; locating and orienting a femoral insertion site; positioning a femoral aiming device; drilling a bone tunnel, or optionally a pocket, correlated with the femoral insertion site in a substantially slit shaped configuration; removing the femoral aiming device; and optionally cleaning drilling edges. Device 300 is used in the system 3000 and method in this variant of the invention.

The invention provides a system 3000, devices forming the system, and a method of creating a tibial bone tunnel during a ligament reconstruction surgery, comprising the steps of: cleaning and identifying a tibial footprint; measuring a tibial footprint with a template; attaching or adjusting an intra-articular template to a tibial guiding device; attaching or adjusting a corresponding drill sleeve to the tibial guiding device; drilling to provide a guide-wire or a drill which stabilises the tibial guiding device; orienting the tibial guiding device; drilling adjacent bores or adjacent k-wires in case where a drill was set to stabilise the tibial guiding device; removing the tibial guiding device; drilling a bore over the guide-wire or adjacent guide wires; and, optionally cleaning drilling edges.

In yet further variant, the invention provides a system 3000, devices which are included in system 3000 and a method of creating a femoral bone tunnel, comprising the steps of: cleaning and identifying a femoral footprint; measuring a femoral footprint with a template; introducing a k-wire with a stamping device with a corresponding femoral guiding device; setting the k-wire using an aiming template and an arthroscope; drilling to provide a guide-wire or a drill which stabilises the femoral guiding device; orienting the femoral guiding device; drilling adjacent bores or adjacent k-wires in case where a drill was set to stabilise the femoral guiding device; removing the femoral guiding device; drilling a bore over the guide-wire; and, optionally cleaning drilling edges.

In yet another variant, the invention provides a method of preparing a graft for a ligament reconstruction procedure, comprising the steps of: harvesting a tendon; cleaning the tendon; arranging individual tendon strands in a substantially ribbon-like, flat manner to mount and fixate the tendon; and, preparing the individual tendon strands in a linear arrangement.

In yet further variant, the invention provides a system 3000, and devices used in the system and forming the system 3000, and a method of preparing a graft for a ligament reconstruction procedure, comprising the steps of: harvesting a tendon to obtain a round tendon structure; cleaning the round tendon structure; preparing a substantially flat, ribbon-like structure from the round tendon structure along a longitudinal axis of the round tendon structure following tendon fibers, the substantially flat, ribbon-like structure having a first side and a second side; spanning the first side of the substantially flat, ribbon-like structure substantially orthogonally to the longitudinal axis of the substantially flat, ribbon-like structure by attaching the substantially flat, ribbon-like to an attachment structure; and, spanning the second side of the substantially flat, ribbon-like structure substantially orthogonally to the longitudinal axis by attaching the substantially flat, ribbon-like to an attachment structure.

In yet further variant, the invention provides a method of preparing a graft for a reconstruction procedure, comprising the steps of: harvesting a tendon having a plurality of tendon strands; cleaning the tendon; providing a split-button device having a lower partition and an upper partition; introducing the tendon into the lower partition; introducing the tendon into the upper partition; providing a fiber-pod having separate fields and loops; laying each tendon strand in a separate field; weaving the plurality of tendon strands through the loops with a plurality of pull chords; tightening the tendon strands by pulling the pull chords; and, optionally securing the tendon strands with sutures.

The invention provides a system 3000, devices within system 3000, and a method of preparing a graft for a procedure, comprising the steps of: harvesting a flat, ribbon-like portion of a tendon (e.g. patella or quadriceps tendon); cleaning the tendon portion, preparing a substantially flat tendon structure; and attaching said structure to fixation means allowing the upholding of a flat appearance of the graft.

In yet further variant of the invention, it provides a system 3000 (FIG. 24) in which the system is used to execute a method of reconstructing a ligament using a first bone tunnel and a second bone tunnel, comprising the steps of: creating the first bone tunnel according to a first native ligament insertion site; creating a second bone tunnel according to a second native ligament insertion site; preparing a substantially ribbon-like, flat graft, the graft having a first end and a second end; pulling in the graft via the first bone tunnel into the second bone tunnel; fixing a portion of the first end of the graft in the second bone tunnel; tightening and fastening the graft; and, fixing a portion of the second end of the graft in the first bone tunnel. In this variant of the method the first bone tunnel is a tibial bone tunnel, and the second bone tunnel is a femoral bone.

It should be appreciated that the particular implementations shown and herein described are representative of the invention and its best mode and are not intended to limit the scope of the present invention in any way. Moreover, the system contemplates the use, sale and/or distribution of any goods, services or information having similar functionality described herein.

The specification and figures should be considered in an illustrative manner, rather than a restrictive one, and all modifications described herein are intended to be included within the scope of the invention claimed. Accordingly, the scope of the invention should be determined by the appended claims (as they currently exist or as later amended or added, and their legal equivalents) rather than by merely the examples described above. Steps recited in any method or process claims, unless otherwise expressly stated, may be executed in any order and are not limited to the specific order presented in any claim. Further, the elements and/or components recited in apparatus claims may be assembled or otherwise functionally configured in a variety of permutations to produce substantially the same result as the present invention. Consequently, the invention should not be interpreted as being limited to the specific configuration recited in the claims. Benefits, other advantages and solutions mentioned herein are not to be construed as critical, required or essential features or components of any or all the claims.

As used herein, the terms "comprises", "comprising", or variations thereof, are intended to refer to a non-exclusive listing of elements, such that any apparatus, process, method, article, or composition of the invention that comprises a list of elements that does not include only those elements recited, but may also include other elements described in the instant specification. Unless otherwise explicitly stated, the use of the term "consisting" or "consisting of" or "consisting essentially of" is not intended to limit the scope of the invention to the enumerated elements named thereafter, unless otherwise indicated. Other combinations and/or modifications of the above-described elements, materials or structures used in the practice of the present invention may be varied or adapted by the skilled artisan to other designs without departing from the general principles of the invention.

The patents and articles mentioned above are hereby incorporated by reference herein, unless otherwise noted, to the extent that the same are not inconsistent with this disclosure.

Other characteristics and modes of execution of the invention are described in the appended claims. Further, the invention should be considered as comprising all possible combinations of every feature described in the instant specification, appended claims, and/or drawing figures, which may be considered new, inventive and industrially applicable.

Additional features and functionality of the invention are described in the claims appended hereto. Such claims are hereby incorporated in their entirety by reference thereto in this specification and should be considered as part of the application as filed.

Multiple variations and modifications are possible in the embodiments of the invention described here. Although certain illustrative embodiments of the invention have been shown and described here, a wide range of changes, modifications, and substitutions is contemplated in the foregoing disclosure. While the above description contains many specific details, these should not be construed as limitations on the scope of the invention, but rather exemplify one or another preferred embodiment thereof. In some instances, some features of the present invention may be employed without a corresponding use of the other features. Accordingly, it is appropriate that the foregoing description be construed broadly and understood as being illustrative only, the spirit and scope of the invention being limited only by the claims which ultimately issue in this application.

What is claimed is:

1. A system for preparing a first and second bone for a graft procedure, the system comprising:
   a) a first device comprising an intra-articular portion and an extra-articular portion connected in a fixed relationship, each portion with a plurality of bore guides coaxial with at least two bore guides of the other portion for creating on the first bone a half-moon shaped aperture substantially mimicking a first native ligament attachment footprint, the aperture having a substantially half-moon shaped two dimensional footprint, the first device adapted for sequential drilling and/or burring of overlapping bores, the overlapping bores being arranged to create the half-moon shaped aperture; and,
   b) a second device for creating on the second bone an entrance aperture point substantially mimicking a second native ligament attachment footprint, the aperture optionally having a substantially slit shaped two dimensional footprint, the second device adapted for sequential drilling and/or burring of second bone overlapping bores, the second bone overlapping bores being arranged in a slit-shaped manner to create a slit-shaped insertion site, the slit-shaped insertion site substantially conforming in size, cross-sectional dimension and shape to the second native ligament attachment footprint.

2. The system of claim 1 further comprising a third device, the third device selected from the group of third devices consisting of a first third device for creating a substantially ribbon-like ACL graft, said graft having a first end and a second end, a second third device adapted for retaining the ribbon-like appearance of the graft by affixing parallel tendon bundles or affixing tendons which are split and prepared in a way to give a flat, ribbon like appearance, and a third third device for affixing portions of a tendon which have been prepared to give a substantially flat and ribbon like appearance.

3. The system of claim 2 further comprising a fourth device for fixing at least a portion of the first end of the graft at a tibial anchor point, the fourth device adapted for affixing a substantially flat graft to a substantially flat structure on the fourth device by attaching the graft to the substantially flat structure, the substantially flat structure being constructed to be flexible so as to pass through a c-shaped bone tunnel.

4. The system of claim 3 further comprising a fifth device for fixing at least a portion of the second end of the graft in a femoral anchor point, the fifth device having a button-like feature for the extra-osseous fixation of the graft, the graft being connected to an appliance, the appliance allowing the affixing of a substantially flat graft to a flat structure on the fifth device by attaching the graft to said flat structure, the flat structure being flexible enough to first pass through a half-moon shaped bone tunnel and second through said slit-shaped bone tunnel.

5. A method of preparing a tibia for a graft for ACL reconstruction, the graft comprising a first portion which is shaped and dimensioned to substantially conform to a slit shaped bone entrance point, a second portion that is shaped and dimensioned to be substantially ribbon like, and a third portion which is shaped and dimensioned to substantially conform to a half-moon shaped aperture, comprising the steps of:
cleaning and identifying a tibial ACL footprint;
measuring the tibial ACL footprint with a template;
locating and orienting a tibial insertion site;
positioning a tibial aiming device;
drilling a bone tunnel, or optionally a pocket, correlated to the tibial insertion site in a substantially half-moon shaped configuration;
removing the tibial aiming device; and,
optionally cleaning drilling edges.

6. A method of preparing a femur bone for an anatomically correct ACL reconstruction graft comprising a first portion which is shaped and dimensioned to substantially conform to a slit shaped bone entrance point, a second portion that is shaped and dimensioned to be substantially ribbon like, and a third portion which is shaped and dimensioned to substantially conform to a half-moon shaped aperture comprising the steps of:
cleaning and identifying a femoral ACL footprint;
measuring the femoral ACL footprint with a template;
locating and orienting a femoral insertion site;
positioning a device of claim 1;
drilling a bone tunnel, or optionally a pocket, correlated with the femoral insertion site in a substantially slit shaped configuration;
removing the device of claim 1; and
optionally cleaning drilling edges.

7. A method of creating a tibial bone tunnel during a ligament reconstruction surgery suitable for a graft for ACL reconstruction, the graft comprising a first portion which is shaped and dimensioned to substantially conform to a slit shaped bone entrance point, a second portion that is shaped and dimensioned to be substantially ribbon like, and a third portion which is shaped and dimensioned to substantially conform to a half-moon shaped aperture, comprising the steps of:
cleaning and identifying a tibial footprint;
measuring a tibial footprint with a template;
attaching or adjusting an intra-articular template to a tibial guiding device;
attaching or adjusting a corresponding drill sleeve to the tibial guiding device;
drilling to provide a guide-wire or a drill which stabilises the tibial guiding device;
orienting the tibial guiding device;
drilling adjacent bores or adjacent k-wires in case where a drill was set to stabilise the tibial guiding device;
removing the tibial guiding device;
drilling a bore over the guide-wire or adjacent guide wires; and,
optionally cleaning drilling edges.

8. A method of creating a femoral bone tunnel during a ligament reconstruction surgery suitable for a graft for ACL reconstruction, the graft comprising a first portion which is shaped and dimensioned to substantially conform to a slit shaped bone entrance point, a second portion that is shaped and dimensioned to be substantially ribbon like, and a third portion which is shaped and dimensioned to substantially conform to a half-moon shaped aperture, comprising the steps of:
cleaning and identifying a femoral footprint;
measuring a femoral footprint with a template;
introducing a k-wire with a stamping device with a corresponding femoral guiding device;
setting the k-wire using an aiming template and an arthroscope;
drilling to provide a guide-wire or a drill which stabilises the femoral guiding device;
orienting the femoral guiding device;
drilling adjacent bores or adjacent k-wires in case where a drill was set to stabilise the femoral guiding device;
removing the femoral guiding device;
drilling a bore over the guide-wire; and,
optionally cleaning drilling edges.

* * * * *